(12) United States Patent
Araldi et al.

(10) Patent No.: US 7,863,312 B2
(45) Date of Patent: Jan. 4, 2011

(54) PYRAZOLIDINONE COMPOUNDS AS LIGANDS OF THE PROSTAGLANDIN EP2 AND/OR EP4 RECEPTORS

(75) Inventors: Gian Luca Araldi, Plymouth, MA (US); Yihua Liao, Westwood, MA (US); Adulla P. Reddy, Walpole, MA (US); Zhong Zhao, Wayland, MA (US)

(73) Assignee: Merck Serono SA, Coinsins (CH)

( * ) Notice: Subject to any disclaimer, the term of this patent is extended or adjusted under 35 U.S.C. 154(b) by 0 days.

(21) Appl. No.: 12/120,408

(22) Filed: May 14, 2008

(65) Prior Publication Data

US 2008/0234346 A1    Sep. 25, 2008

Related U.S. Application Data

(62) Division of application No. 10/492,910, filed as application No. PCT/US02/33964 on Oct. 23, 2002, now Pat. No. 7,410,991.

(60) Provisional application No. 60/336,048, filed on Oct. 23, 2001.

(51) Int. Cl.
*A61K 31/4152* (2006.01)
*A61P 15/00* (2006.01)
*A61P 11/00* (2006.01)

(52) U.S. Cl. .................... 514/404; 548/370.4
(58) Field of Classification Search ............. 514/404; 548/370.4
See application file for complete search history.

(56) References Cited

U.S. PATENT DOCUMENTS

| | | | |
|---|---|---|---|
| 3,873,566 A | 3/1975 | Scribner | |
| 4,211,876 A | 7/1980 | Scribner | |
| 5,605,814 A | 2/1997 | Abramovitz et al. | |
| 5,759,789 A | 6/1998 | Abramovitz et al. | |
| 6,211,197 B1 | 4/2001 | Belley et al. | |

FOREIGN PATENT DOCUMENTS

| | | |
|---|---|---|
| EP | 0 752 421 | 1/1997 |
| EP | 1 114 816 | 7/2001 |
| EP | 1 121 939 | 8/2001 |
| EP | 1 132 086 | 9/2001 |
| GB | 1 428 431 | 3/1976 |
| WO | 96/03380 | 2/1996 |
| WO | 96/06822 | 3/1996 |
| WO | 97/00863 | 1/1997 |
| WO | 97/00864 | 1/1997 |

OTHER PUBLICATIONS

Database Crossfire Beilstein 'Online! Beilstein Institut zur Foerderung der Chemischen Wissenschaften, Frankfurt am Main, DE; Database accession No. BRN:5033580 XP002234450 abstract & Chantrapromma, K.; et al.: Chem. Soc. Perkin. Trans. 1, vol. 5, 1983, pp. 1029-1039.
Database Crossfire Beilstein 'Online! Beilstein Institut zur Foerderung der Chemischen Wissenschaften, Frankfurt am Main, DE; Database accession No. BRN: 911732 XP002234451 abstract & J. Pharm: Sci., vol. 58, 1969, pp. 724-727.
Database Crossfire Beilstein 'Online! Beilstein Institut zur Foerderung der Chemischen Wissenschaften, Frankfurt am Main, DE; Database accession No. BRN 1562407 XP002234452 abstract & J. Heterocycl. Chem., vol. 5, 1968, pp. 397-403.
Gregory B. Bennett, et al. Journal of Medicinal Chemistry, vol. 19, No. 5 pp. 709-714 1976.
Stephen L. Tilley, et al. The Journal of Clinical Investigation, vol. 103, No. 11, pp. 1539-1545 1999.
Toshiaki Minami, et al. Br. J. Pharmacol. vol. 112, pp. 735-740 1994.

*Primary Examiner*—Kamal A Saeed
(74) *Attorney, Agent, or Firm*—Oblon, Spivak, McClelland, Maier & Neustadt, L.L.P.

(57) ABSTRACT

The invention provides substituted pyrazolidinone compounds, and methods of treatment and pharmaceutical compositions that utilize or comprise one or more such compounds. Compounds of the invention are useful for a variety of therapies, including treating or preventing preterm labor, dysmenorrhea, asthma, hypertension, infertility or fertility disorder, undesired blood clotting, preeclampsia or eclampsia, an eosinophil disorder, sexual dysfunction, osteoporosis and other destructive bone disease or disorder, and other diseases and disorders associated with the prostaglandin EP2 and/or EP4 receptors.

17 Claims, No Drawings

PYRAZOLIDINONE COMPOUNDS AS LIGANDS OF THE PROSTAGLANDIN EP2 AND/OR EP4 RECEPTORS

BACKGROUND OF THE INVENTION

1. Field of the Invention

The present invention relates to substituted pyrazolidinone compounds, and methods of treatment and pharmaceutical compositions that utilize or comprise one or more such compounds. Compounds of the invention are useful for a variety of therapies, including treatment of preterm labor, dysmenorrhea, asthma, hypertension, infertility or fertility disorder, undesired blood clotting, preeclampsia or eclampsia, an eosinophil disorder, sexual dysfunction, osteoporosis and other destructive bone disease or disorders, and other diseases and disorders associated with the prostaglandin EP2 and/or EP4 receptors.

2. Background

Certain prostanoid receptors and modulators of those receptors have been reported. See generally *Eicosanoids: From Biotechnology to Therapeutic Applications* (Plenum Press, New York); *Journal of Lipid Mediators and Cell Signalling* 14: 83-87 (1996); *The British Journal of Pharmacology*, 112: 735-740 (1994); PCT applications WO 96/06822, WO 97/00863, WO 97/00864, and WO 96/03380; EP 752421; U.S. Pat. Nos. 6,211,197 4,211,876 and 3,873,566; and Bennett et al. *J. Med. Chem.*, 19(5): 715-717 (1976).

Physiological action of prostaglandin E2 (PGE2) is reported to be mediated through interaction with the prostaglandin E receptor(s). Four subtypes of the prostaglandin EP receptor have been identified: EP1, EP2, EP3, and EP4. The prostaglandin EP2 receptor including the cloning thereof has been reported. See U.S. Pat. Nos. 5,605,814 and 5,759,789. Binding of PGE2 to the EP2 receptor protein has been reported to result in an increase in cAMP levels, which can cause smooth muscle relaxation. See U.S. Pat. No. 5,605,814. Binding of PGE2 to the EP4 receptor also causes increases in cAMP levels leading to smooth muscle relaxation.

It also has been reported that genetic deletion of the EP2 receptor indicates a key role in normal female fertility and control of blood pressure. See *Journal of Clinical Investigation*, 103(ii):1539-1545 (1999).

It would be desirable to have new compounds and methods for treatment of diseases and disorders associated with the prostaglandin EP2 and/or EP4 receptors. It also would be desirable to have new compounds for treatment of diseases and disorders associated with inappropriate activation of the EP2 and/or EP4 receptors.

SUMMARY OF THE INVENTION

We have now found substituted pyrazolidinone-type compounds that are useful for a variety of therapies, including alleviating, preventing and/or treating preterm labor, dysmenorrhea, asthma, hypertension, sexual dysfunction, osteoporosis and other destructive bone disease or disorder, inflammation, and other diseases and disorders associated with the prostaglandin EP2 and/or EP4 receptors.

Preferred compounds of the invention have fully substituted pyrazolidinone ring nitrogens, with one or two optional non-hydrogen substituents at other ring positions (i.e. nuclear carbon positions).

Generally preferred for use in the therapeutic methods of the invention are substituted pyrazolidinone compounds of the following Formula I:

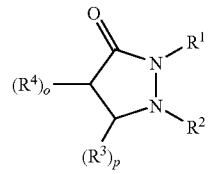

wherein $R^1$ and $R^2$ are each independently hydrogen or a non-hydrogen substituent, preferably where one or both of $R^1$ and $R^2$ are non-hydrogen substituents such as optionally substituted alkyl preferably having 1 to about 20 carbons; optionally substituted alkenyl preferably having from 2 to about 20 carbons; optionally substituted alkynyl preferably having from 2 to about 20 carbons; optionally substituted heteroalkyl preferably having from 1 to about 20 carbons; optionally substituted heteroalkenyl preferably having from 2 to about 20 carbons; optionally substituted heteroalkynyl preferably having from 2 to about 20 carbons; optionally substituted aralkyl; optionally substituted heteroarylalkyl; and optionally substituted heteroalicyclicalkyl; Preferably, at least one of $R^1$ and $R^2$ is not H.

$R^3$ and $R^4$ independently each may be hydrogen or a non-hydrogen substituent such as defined above for $R^1$ and $R^2$, or optionally substituted carbocyclic aryl, optionally substituted heteroalicyclic, or optionally substituted heteroaryl; and pharmaceutically acceptable salts thereof.

Preferred compounds of the invention include those that have substitution only at one or both of the nitrogen ring atoms (i.e. the nuclear carbons are unsubstituted), such as compounds of the following Formula II:

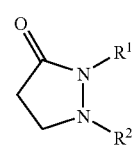

wherein $R^1$ and $R^2$ are the same as defined in Formula I above, and preferably one or both of $R^1$ and $R^2$ are other than hydrogen; and pharmaceutically acceptable salts thereof.

Preferred nitrogen ring substituents include a saturated or unsaturated carbon chain, e.g. a $C_{1-20}$ alkyl, $C_{2-20}$ alkenyl, or $C_{2-20}$ alkynyl chain, preferably a chain having 2, 3 or 4 to about 5, 6, 7, 8, 9, 10, 11 or 12 carbons; zero, one, two or more carbon-carbon multiple bonds; and one or more additional substitutents on the carbon chain, such as hydroxy, $C_{1-12}$alkoxy, optionally substituted carbocyclic aryl, optionally substituted heteroalicyclic, or optionally substituted heteroaryl. Particularly preferred substituents of such alkyl, alkenyl and alkynyl chains are optionally substituted carbocyclic groups, particularly optionally substituted phenyl groups such as phenyl groups having one or more phenyl ring substituents, preferably one or two phenyl ring substituents.

More particularly, preferred compounds include those of the following Formula III:

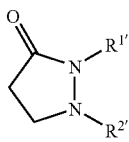

wherein $R^{1'}$ and $R^{2'}$ are each independently optionally substituted $C_{1-20}$alkyl, optionally substituted $C_{2-20}$alkenyl, or optionally substituted $C_{2-20}$alkynyl; and pharmaceutically acceptable salts thereof.

Suitable compounds also may be substituted at other pyrazolidinone ring positions, such as compounds of the following Formula IV:

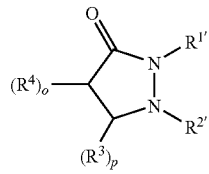

wherein $R^{1'}$ and $R^{2'}$ are the same as defined in Formula III above, and $R^3$ and $R^4$ are the same as defined in Formula I above; and pharmaceutically acceptable salts thereof.

Preferred $R^{1'}$ groups of Formulae III and IV have one or more acidic substituents on the carbon chain, such as carboxy, sulfono, and the like. Preferred $R^{2'}$ groups have one or more hydroxy substituents on the carbon chain. Specifically preferred $R^{1'}$ groups include $C_{1-8}$ alkyl, $C_{2-8}$ alkenyl, or $C_{2-8}$ alkynyl, more preferably $C_{1-6}$ alkyl, $C_{2-6}$ alkenyl or $C_{2-6}$ alkynyl, substituted by one or more acidic groups such as carboxy, or carbocyclic aryl having one or more acidic ring substituents such as a benzoic acid moiety. Preferably, such substituents of an $R^{1'}$ group are substituted at the terminal carbon of a chain, e.g. —$CH_2CH_2C_6H_4COOH$ and —$CH_2CH$=$CH(CH_2)_3COOH$. With respect to $R^{2'}$ groups, preferred hydroxy substitution is at a non-terminal chain position (i.e. to provide a secondary or tertiary carbon), e.g. —$(CH_2)_{1-4}(CHOH)(CH_2)_{1-6}CH_3$ such as —$(CH_2)_2(CHOH)(CH_2)_4CH_3$, —$CH_2CH$=$CH(CHOH)(CH_2)_3CH_3$ and —$CH$=$CHCH_2(CHOH)(CH_2)_2CH_3$.

Particularly preferred compounds of the invention include those of the following Formula V:

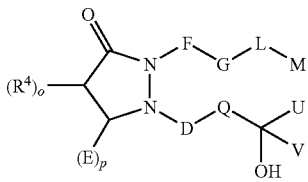

wherein each $R^4$ is independently hydrogen, optionally substituted alkyl preferably having from 1 to about 20 carbon atoms, optionally substituted carbocyclic aryl or optionally substituted heteroaromatic, and preferably one or both R groups are hydrogen;

each E is independently hydrogen, hydroxy, optionally substituted alkoxy preferably having 1 to about 20 carbon atoms, optionally substituted alkylthio preferably having 1 to about 20 carbon atoms, optionally substituted alkylsulfinyl preferably having 1 to about 20 carbon atoms, optionally substituted alkylsulfonyl preferably having 1 to about 20 carbon atoms, and preferably E is hydrogen;

o and p are each independently zero, 1 or 2, and preferably o and p are each independently 2;

F is —$(CH_2)_n$— with n being an integer of 1-6;

G is a —C≡C—, —CH=CH—, —$CH_2$—, optionally substituted carbocyclic aryl or optionally substituted heteroaromatic;

L is $(CH_2)_{n'}$ with n' being an integer of from 0-3;

M is COX, $SO_2X$ with X being OR' or NHR" and R' being H or optionally substituted alkyl preferably having 1 to about 12 carbon atoms; optionally substituted tetrazole; $NO_2$; $NHSO_2R$; or NHC(O)R, where R is H or optionally substituted alkyl preferably having 1 to about 12 carbon atoms;

D is $(CH_2)_{n''}$ with n" being an integer of from 0-2;

Q is $(CH2)_{n'''}$ with n''' being 0 or 1, —CH=CH—, or an optionally substituted carbocyclic aryl preferably optionally substituted phenyl;

U and V are each independently optionally substituted alkyl preferably having from 1 to about 20 carbon atoms, optionally substituted alkenyl preferably having 2 to about 20 carbon atoms, optionally substituted alkynyl preferably having 2 to about 20 carbon atoms; optionally substituted carbocyclic aryl such as optionally substituted phenyl, or optionally substituted heteroaromatic; and pharmaceutically acceptable salts thereof.

Preferred compounds of the invention include compounds of Formulae I', IV' and V' which are defined the same as Formulae I, IV and V respectively, expect that the sum of o and p is at least one, i.e. the pyrazolidinone has at least one non-hydrogen ring carbon substituent. More preferred compounds of the invention include those of the following Formula VI:

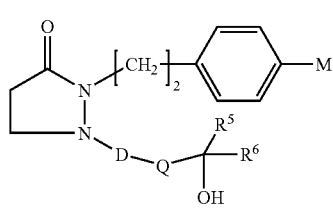

Wherein M is COX with X is OR' and R' is H;

D is $(CH_2)_{n''}$ wherein n" is 2;

Q is $(CH_2)_{n'''}$ wherein n''' is 0 or 1;

$R^5$ is H or optionally branched $C_1$-$C_6$ alkyl;

$R^6$ is optionally branched $C_1$-$C_6$ alkyl, optionally substituted aryl $C_1$-$C_6$ alkyl, optionally substituted heteroaryl $C_1$-$C_6$ alkyl, optionally substituted $C_3$-$C_6$ cylcoalkyl $C_1$-$C_6$ alkyl or optionally substituted $C_3$-$C_6$ cycloalkyl.

A particularly preferred embodiment of the invention is pyrazolidinone derivatives according to formula VI wherein M is —C(O)OH; D is —$(CH_2)_2$; Q is —$(CH_2)_{n'''}$— wherein n''' is an integer from 0-1; $R^5$ is H or optionally branched $C_1$-$C_6$ alkyl, preferably H, methyl or ethyl; $R^6$ is optionally branched $C_1$-$C_6$ alkyl, preferably butyl, pentyl, n-isobutyl, 1-methyl propyl, optionally substituted $C_3$-$C_6$ cycloalkyl $C_1$-$C_6$ alkyl, preferably cyclobutyl, optionally substituted $C_3$-$C_6$ cycloalkyl, optionally substituted benzyl optionally fused, preferably unfused;

Other more preferred compounds of invention include those defined in Formula VI wherein M, n" are as defined above; n'" is 1, $R^5$ is H or optionally substituted $C_1$-$C_6$ alkyl; $R^6$ is optionally branched $C_1$-$C_6$ alkyl, preferably butyl, pentyl, n-isobutyl, 1-methyl propyl, optionally substituted $C_3$-$C_6$ cycloalkyl $C_1$-$C_6$ alkyl, preferably cyclobutyl $C_1$-$C_6$ alkyl.

Another more preferred group of compounds of invention include those defined in Formula VI wherein M, n" are as defined as above; n'" is 0; $R^5$ is H; $R^6$ is —$CHR^7$—W, wherein $R^7$ is H, or $C_1$-$C_6$ alkyl, preferably H or methyl, most preferably H; W is optionally substituted aryl, preferably phenyl, substituted phenyl or optionally substituted heteroaryl.

Preferred compounds of the invention exhibit good binding activity in a standard prostaglandin EP2 and/or EP4 receptor binding assays. Such an assays are defined in Examples 31 and 33, which follows.

As discussed above, compounds of the invention are useful for treatment of diseases and disorders associated with prostaglandin, particularly the prostaglandin E2. Therapeutic methods of the invention in general comprise administering an effective amount of one or more compounds as disclosed herein to a mammal in need thereof.

1,2-substituted 5-pyrrolidinone compounds of the invention are particularly useful for treatment of a mammal suffering from or susceptible to (prophylactic therapy) preterm labor, dysmenorrhea, asthma and other conditions treated by bronchodilation, hypertension, congestive heart disease, tissue or organ transplant rejection, undesired blood-clotting and other undesired platelet activities, preeclampsia and/or eclampsia, and eosinphil-related disorders. 1,2-substituted 5-pyrrolidinone compounds of the invention also are useful to treat a mammal suffering from or suspected of suffering from infertility, particularly a female suffering from infertility. 1,2-substituted 5-pyrrolidinone compounds of the invention may be particularly beneficial for treatment of female mammals suffering from an ovulatory disorder. Additionally, 1,2-substituted 5-pyrrolidinone compounds of the invention can be administered to females undergoing reproductive treatments such as in-vitro fertilization or implant procedures, e.g. to stimulate follicular development and maturation. Substituted pyrazolidinone compounds of the invention may also have utility as a media additive for in vitro maturation of follicles, oocytes and/or pre-implantation embryos for improved effectiveness of IVF treatment protocols. Compounds of the invention also are useful to treat sexual dysfunction, including male erectile dysfunction, associated fibrotic disease and female sexual arousal disorder.

Preferred compounds of the invention also will be useful for treatment of undesired bone loss (e.g. osteoporosis, particularly in women) or otherwise promoting bone formation and treatment of other bone diseases such as Paget's disease, healing or replacement of bone grafts, and the like.

Preferred compounds of the invention also will be useful for treating inflammatory and/or autoimmune diseases including, but not restricted to, rheumatoid arthritis, multiple sclerosis, psoriasis, inflammatory bowel disease and ulcerative colitis.

Compounds of the invention also are useful for treatment of a subject suffering from or susceptible to renal dysfunction, including a mammal suffering from or susceptible to acute or chronic renal failure, glomerulonephritis or uraemia.

Compounds of the invention also are useful for treatment of a subject suffering from or susceptible to an immune disorder including an immune deficiency disease or disorder, including such a disorder associated with a viral infection particularly a retroviral infection such as an HIV infection. Particularly benefited by such therapies will be a human suffering from or susceptible to AIDS.

Compounds of the invention will be further useful to reduce elevated intraocular pressure of a subject, e.g. through relaxation of pre-contracted isolated ciliary muscle. In particular, a mammal such as a human suffering from or susceptible to glaucoma or other disorder associated with elevated intra-ocular pressure. Compounds of the invention also will be useful for treatment of a mammal, particularly a human, that is suffering from or susceptible to dry eye.

Compounds of the invention also will be useful for promoting sleep in a subject, e.g. to treat a mammal particularly a human suffering from or susceptible to a sleep disorder such as may be associated with advanced age, such as a human of 65 years or older.

Compounds of the invention will be further useful to treat a mammal suffering from or susceptible to ulcers, particularly gastric ulcers. Such therapies may be conducted in conjunction with a patient being treated with an anti-inflammatory agent, which can promote gastric ulcers.

Compounds of the invention also may be administered to a mammal particularly a human that is suffering from or susceptible to a skin disorder, particularly dry skin (ichthyosis) or skin rush.

In a further aspect, the invention provides a use of a substituted pyrazolidinone compound, including a particularly of any one of Formulae I through VI for the treatment or prevention (including prophylactic treatment) of a disease or condition as disclosed herein, including preterm labor, ovulation induction, cervical ripening, dysmenorrhea, asthma, hypertension, infertility or fertility disorder, undesired blood clotting, preeclampsia or eclampsia, an eosinophil disorder, sexual dysfunction, osteoporosis and other destructive bone disease or disorder, renal dysfunction (acute and chronic), immune deficiency disorder or disease, dry eye, skin disorders such as ichthyosis, elevated intraocular pressure such as associated with glaucoma, sleep disorders, ulcers, and other diseases and disorders associated with the prostaglandins and receptors thereof.

In a yet further aspect, the invention use of a substituted pyrazolidinone compound, including a compound of any one of Formulae I, I', III, IV, IV', V, V' and VI for the preparation of a medicament for the treatment or prevention (including prophylactic treatment) of a disease or condition as disclosed herein, including infertility, preterm labor, asthma, hypertension, sexual dysfunction including erectile dysfunction, osteoporosis and other destructive bone disease or disorder, inflammation, and other diseases and disorders associated with the prostaglandin EP2 receptor.

The invention also provides pharmaceutical compositions that comprise one or more substituted pyrazolidinone compounds of the invention and a suitable carrier for the compositions. Other aspects of the invention are disclosed infra.

DETAILED DESCRIPTION OF THE INVENTION

We have now discovered that substituted pyrazolidinone compounds, including compounds of the above Formulae I, I', II, III, IV, IV', V, V' and VI are useful for treatment of a variety of disorders, particularly diseases and disorders associated with prostaglandin, especially the prostaglandin E2 receptor, such as by inhibiting prostanoid-induced smooth muscle contraction.

Suitable alkyl substituent groups of compounds of the invention (which includes compounds of Formulae I, I', II, III, IV, IV', V, V' and VI as those formulae are defined above) typically have from 1 to about 12 carbon atoms, more preferably 1 to about 8 carbon atoms, still more preferably 1, 2, 3, 4, 5, or 6 carbon atoms. As used herein, the term alkyl unless otherwise modified refers to both cyclic and noncyclic groups, although of course cyclic groups will comprise at least three carbon ring members. Preferred alkenyl and alkynyl groups of compounds of the invention have one or more unsaturated linkages and typically from 2 to about 12 carbon atoms, more preferably 2 to about 8 carbon atoms, still more preferably 2, 3, 4, 5, or 6 carbon atoms. The terms alkenyl and alkynyl as used herein refer to both cyclic and noncyclic groups, although straight or branched noncyclic groups are generally more preferred. Preferred alkoxy groups of compounds of the invention include groups having one or more oxygen linkages and from 1 to about 12 carbon atoms, more preferably from 1 to about 8 carbon atoms, and still more preferably 1, 2, 3, 4, 5 or 6 carbon atoms. Preferred alkylthio groups of compounds of the invention include those groups having one or more thioether linkages and from 1 to about 12 carbon atoms, more preferably from 1 to about 8 carbon atoms, and still more preferably 1, 2, 3, 4, 5, or 6 carbon atoms. Preferred alkylsulfinyl groups of compounds of the invention include those groups having one or more sulfoxide (SO) groups and from 1 to about 12 carbon atoms, more preferably from 1 to about 8 carbon atoms, and still more preferably 1, 2, 3, 4, 5, or 6 carbon atoms. Preferred alkylsulfonyl groups of compounds of the invention include those groups having one or more sulfonyl ($SO_2$) groups and from 1 to about 12 carbon atoms, more preferably from 1 to about 8 carbon atoms, and still more preferably 1, 2, 3, 4, 5 or 6 carbon atoms. Preferred aminoalkyl groups include those groups having one or more primary, secondary and/or tertiary amine groups, and from 1 to about 12 carbon atoms, more preferably 1 to about 8 carbon atoms, still more preferably 1, 2, 3, 4, 5, or 6 carbon atoms. Secondary and tertiary amine groups are generally more preferred than primary amine moieties. Suitable heteroaromatic groups of compounds of the invention contain one or more N, O or S atoms and include, e.g., coumarinyl including 8-coumarinyl, quinolinyl including 8-quinolinyl, pyridyl, pyrazinyl, pyrimidyl, furyl, pyrrolyl, thienyl, thiazolyl, oxazolyl, oxidizolyl, triazole, imidazolyl, indolyl, benzofuranyl and benzothiazole. Suitable heteroalicyclic groups of compounds of the invention contain one or more N, O or S atoms and include, e.g., tetrahydrofuranyl, thienyl, tetrahydropyranyl, piperidinyl, morpholino and pyrrolidinyl groups. Suitable carbocyclic aryl groups of compounds of the invention include single and multiple ring compounds, including multiple ring compounds that contain separate and/or fused aryl groups. Typical carbocyclic aryl groups of compounds of the invention contain 1 to 3 separate or fused rings and from 6 to about 18 carbon ring atoms. Specifically preferred carbocyclic aryl groups include phenyl; naphthyl including 1-naphthyl and 2-naphthyl; biphenyl; phenanthryl; anthracyl; and acenaphthyl. Substituted carbocyclic groups are particularly suitable including substituted phenyl, such as 2-substituted phenyl, 3-substituted phenyl, 4-substituted phenyl, 2,3-substituted phenyl, 2,4-substituted phenyl, and 2,4-substituted phenyl; and substituted naphthyl, including naphthyl substituted at the 5, 6 and/or 7 positions.

Suitable aralkyl groups of compounds of the invention include single and multiple ring compounds, including multiple ring compounds that contain separate and/or fused aryl groups. Typical aralkyl groups contain 1 to 3 separate or fused rings and from 6 to about 18 carbon ring atoms. Preferred aralkyl groups include benzyl and methylenenaphthyl (—$CH_2$-naphthyl), and other carbocyclic aralkyl groups, as discussed above.

Suitable heteroaralkyl groups of compounds of the invention include single and multiple ring compounds, including multiple ring compounds that contain separate and/or fused heteroaromatic groups, where such groups are substituted onto an alkyl linkage. More preferably, a heteroaralkyl group contains a heteroaromatic group that has 1 to 3 rings, 3 to 8 ring members in each ring and from 1 to 3 hetero (N, O or S) atoms, substituted onto an alkyl linkage. Suitable heteroaromatic groups substituted onto an alkyl linkage include e.g., coumarinyl including 8-coumarinyl, quinolinyl including 8-quinolinyl, pyridyl, pyrazinyl, pyrimidyl, furyl, pyrrolyl, thienyl, thiazolyl, oxazolyl, oxidizolyl, triazole, imidazolyl, indolyl, benzofuranyl and benzothiazole.

Suitable heteroalicyclicalkyl groups of compounds of the invention include single and multiple ring compounds, where such groups are substituted onto an alkyl linkage. More preferably, a heteroalicylicalkyl group contains at least one ring that has 3 to 8 ring members from 1 to 3 hetero (N, O or S) atoms, substituted onto an alkyl linkage. Suitable heteroalicyclic groups substituted onto an alkyl linkage include e.g. tetrahydrofuranyl, thienyl, tetrahydropyranyl, piperidinyl, morpholino and pyrrolidinyl groups.

As discussed above, $R^1$, $R^{1'}$, $R^2$, $R^{2'}$, $R^3$, $R^4$, E, G, M, Q, U, and V groups are optionally substituted. A "substituted" $R^1$, $R^{1'}$, $R^2$, $R^{2'}$, $R^3$, $R^4$, E, G, M, Q, U, and V group or other substituent may be substituted by other than hydrogen at one or more available positions, typically 1 to 3 or 4 positions, by one or more suitable groups such as those disclosed herein. Suitable groups that may be present on a "substituted" $R^1$, $R^{1'}R^2R^{2'}$, $R^3$ and $R^4$ group or other substituent include e.g: halogen such as fluoro, chloro, bromo and iodo; cyano; hydroxyl; nitro; azido; alkanoyl such as a $C_{1-6}$ alkanoyl group such as acyl and the like; carboxamido; alkyl groups including those groups having 1 to about 12 carbon atoms, or 1, 2, 3, 4, 5, or 6 carbon atoms; alkenyl and alkynyl groups including groups having one or more unsaturated linkages and from 2 to about 12 carbon, or 2, 3, 4, 5 or 6 carbon atoms; alkoxy groups including those having one or more oxygen linkages and from 1 to about 12 carbon atoms, or 1, 2, 3, 4, 5 or 6 carbon atoms; aryloxy such as phenoxy; alkylthio groups including those moieties having one or more thioether linkages and from 1 to about 12 carbon atoms, or 1, 2, 3, 4, 5 or 6 carbon atoms; alkylsulfinyl groups including those moieties having one or more sulfinyl linkages and from 1 to about 12 carbon atoms, or 1, 2, 3, 4, 5, or 6 carbon atoms; alkylsulfonyl groups including those moieties having one or more sulfonyl linkages and from 1 to about 12 carbon atoms, or 1, 2, 3, 4, 5, or 6 carbon atoms; aminoalkyl groups such as groups having one or more N atoms and from 1 to about 12 carbon atoms, or 1, 2, 3, 4, 5 or 6 carbon atoms; carbocyclic aryl having 6 or more carbons; aralkyl having 1 to 3 separate or fused rings and from 6 to about 18 carbon ring atoms, with benzyl being a preferred group; aralkoxy having 1 to 3 separate or fused rings and from 6 to about 18 carbon ring atoms, with O-benzyl being a preferred group; or a heteroaromatic or heteroalicyclic group having 1 to 3 separate or fused rings with 3 to about 8 members per ring and one or more N, O or S atoms, e.g. coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazolyl, tetrahydrofuranyl, tetrahydropyranyl, piperidinyl, morpholino and pyrrolidinyl.

Preferred substituents of $R^1$, $R^2$, $R^{1'}$, $R^{2'}$ groups and ring substituents of carbocyclic or heteroaromatic groups of compounds of the invention include hydroxy; halogen (F, Cl, Br and I) hydroxyl; azido; nitro; optionally substituted alkyl having 1 to about 12 carbons such as methyl, ethyl, propyl and butyl and branched groups such as isopropyl, sec-butyl and tert-butyl, and including halogenated alkyl, particularly fluoro-alkyl having 1 to about 6 carbon atoms; optionally substituted alkoxy having 1 to about 12 carbons such as methoxy, ethoxy, propoxy and butoxy, and including halogenated alkoxy; optionally substituted alkylthio having 1 to about 6 carbons such as methylthio and ethylthio; optionally substituted alkylsulfinyl having 1 to about 6 carbons such as methylsulfinyl (—S(O)CH$_3$) and ethylsulfinyl (—S(O)CH$_2$CH$_3$); optionally substituted alkylsulfonyl having 1 to about 6 carbons such as methylsulfonyl (—S(O)$_2$CH$_3$) and ethylsulfonyl (—S(O)$_2$CH$_2$CH$_3$); and optionally substituted arylalkoxy such as benzyloxy (C$_6$H$_5$CH$_2$O—); carboxy (—COOH) and alkanoyl such as alkanoyl having one or more keto groups and 1 to about 12 carbons such as formyl (—C(=O)H), acetyl, and the like.

A particularly preferred embodiment of the invention is pyrazolidinone derivatives according to formula VI wherein M is —C(O)OH; D is —(CH$_2$)$_2$; Q is (CH$_2$)$_{n'''}$ wherein n''' is 0 or 1; R$^5$ is H, optionally branched C$_1$-C$_6$ alkyl, preferably H or methyl or ethyl; R$^6$ is optionally branched C$_1$-C$_6$ alkyl, preferably butyl, pentyl, n-isobutyl, 1-methyl propyl, optionally substituted C$_3$-C$_6$ cycloalkyl C$_1$-C$_6$ alkyl, preferably substituted cyclobutyl C$_1$-C$_6$ alkyl, optionally substituted aryl C$_1$-C$_6$ alkyl, preferably optionally fused benzyl or optionally substituted heteroaryl C$_1$-C$_6$ alkyl;

Another particularly preferred embodiment of the invention is pyrazolidinone derivatives according to formula VI wherein M is —C(O)OH; D is —(CH$_2$)$_2$; Q is —(CH$_2$)$_{n'''}$ wherein n''' is 1; R$^5$ is H or C$_1$-C$_6$ alkyl, preferably H, methyl or ethyl; and R$^6$ is C$_1$-C$_6$ alkyl, preferably butyl, pentyl or 1-methyl propyl, C$_3$-C$_6$ cycloalkyl C$_1$-C$_6$ alkyl, preferably 1-(cyclopropylmethyl)cyclobutyl or 1-ethylcyclobutyl.

Another particularly preferred embodiment of the invention is pyrazolidinone derivatives according to formula VI wherein M is —C(O)OH; D is —(CH$_2$)$_2$; Q is —(CH$_2$)$_{n'''}$ wherein n''' is 0; R$^5$ is H; R$^6$ is CHR$^7$—W, wherein R$^7$ is H or methyl, preferably H; W is optionally fused aryl, preferably optionally fused phenyl, preferably unfused phenyl, preferably unsubstituted phenyl or substituted phenyl C$_1$-C$_6$ alkyl (substituted with a group selected from halogen, trifluoro methyl, oxo-trifluoromethyl), such as —CH(CH$_3$)Phe, 3-chloro-benzyl, 3-fluoro-benzyl, 3-iodo-benzyl, 3-trifluomethoxy benzyl, 3-trifluomethyl benzyl or optionally substituted heteroaryl such as 5-methyl-(1,3) benzodioxole.

Another particularly preferred embodiment of the invention is pyrazolidinone derivatives according to formula VI wherein M is —C(O)OH; D is —(CH$_2$)$_2$; Q is —(CH$_2$)$_{n'''}$ wherein n''' is 0; R$^5$ is H; R$^6$ is —CHR$^5$—W, wherein R$^7$ is H; W is phenyl substituted with C$_1$-C$_6$ alkyl, preferably methyl.

It should be understood that alkoxy, alkylthio, alkylsulfinyl, alkylsulfonyl and aminoalkyl substituent groups described above include groups where a hetero atom is directly bonded to a ring system, such as a carbocyclic aryl group or heteroaromatic group or heteroalicyclic group including pyrazolidinone group, as well as groups where a hetero atom of the group is spaced from such ring system by an alkylene linkage, e.g. of 1 to about 4 carbon atoms.

The term "C$_1$-C$_6$-alkyl" refers to monovalent branched or unbranched alkyl groups having 1 to 5 carbon atoms. This term is exemplified by groups such as methyl, ethyl, n-propyl, isopropyl, n-butyl, isobutyl, tert-butyl, n-hexyl and the like.

The term "C$_3$-C$_6$-cycloalkyl C$_1$-C$_6$-alkyl" refers to C$_1$-C$_6$-alkyl groups, as defined above, having saturated carbocyclic rings having 3 to 6 carbon atoms as substituent. Examples include ethyl cyclobutyl, cyclopropylmethyl cyclobutyl and the like.

The term "C$_3$-C$_6$-cycloalkyl" refers to saturated carbocyclic rings having 3 to 6 carbon atoms. Examples include cyclopropyl, cyclobutyl, cyclopentyl, cyclohexyl, cyclohexenyl and the like.

The term "Aryl" refers to aromatic carbocyclic groups of from 6 to 14 carbon atoms having a single ring (e.g. phenyl) or multiple condensed rings (e.g. naphthyl). Examples include phenyl, naphthyl, phenanthrenyl and the like.

The term "Aryl C$_1$-C$_6$-alkyl" refers to C$_1$-C$_6$-alkyl groups, as defined above, having an aryl substituent as defined above. Examples include benzyl.

The term "Heteroaryl" refers to a monocyclic heteroaromatic, or a bicyclic or a tricyclic fused-ring heteroaromatic group containing at least one heteroatom selected from S, N and O. Particular examples of heteroaromatic groups include optionally substituted pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, benzodioxolyl, quinolizinyl, quinazolinyl, pthalazinyl, quinoxalinyl, cinnnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetra-hydroisoquinolyl, purinyl, pteridinyl, carbazolyl, xanthenyl or benzoquinolyl.

The term "Heteroaryl C$_1$-C$_6$-alkyl" refers to C$_1$-C$_6$-alkyl groups having a heteroaryl substituent, including 2-furylmethyl, 2-thienylmethyl, 2-(1H-indol-3-yl)ethyl and the like.

The term "heteroalkyl" is used herein is inclusive of alkoxy, alkylthio, alkylamino, alkylsulfinyl and alkylsulfonyl. The term "heteroalkenyl" as used herein is inclusive of such alkoxy, alkylthio, alkylamino, alkylsulfinyl and alkylsulfonyl groups that further include one or more carbon-carbon double bonds, typically one or two carbon-carbon double bonds. The term "heteroalkynyl" as used herein is inclusive of such alkoxy, alkylthio, alkylamino, alkylsulfinyl and alkylsulfonyl groups that further include one or more carbon-carbon triple bonds, typically one or two carbon-carbon triple bonds.

The term "acidic substituent" is used for a substituent comprising an acidic hydrogen which, within the context of the invention, means a group having a hydrogen atom that can be removed by a base yielding an anion or its corresponding salt or solvate. The general principles of acidity and basicity of organic materials are well understood and are to be understood as defining the acidic substituent. They will not be detailed here. However, a description appears in Streitwieser, A. and Heathcock, C. H. "Introduction to Organic Chemistry, Second Edition" (Macmillan, N.Y., 1981), pages 60-64. Generally, acidic groups of the invention have pK values less than that of water, usually less than pK=10, typically less than pK=8, and frequently less than pK=6. They are chosen among the acids of carbon, sulfur, phosphorous and nitrogen, typically the carboxylic, sulfuric, sulfonic, sulfinic, phosphoric and phosphonic acids. Exemplary of acidic substituent are —CO$_2$H, —OSO$_3$H, —SO$_3$H, —SO$_2$H, —OPO$_3$H$_2$ and —PO$_3$H$_2$.

Specifically preferred compounds of the invention include the following depicted compounds, and pharmaceutically acceptable salts of these compounds.

4-[2-(2-(3-hydroxyoctyl)-5-oxopyrazolidin-1-yl)ethyl]benzoic acid;

4-{2-[2-(4-hydroxynon-2-ynyl)-5-oxopyrazolidin-1-yl]ethyl}benzoic acid;

4-{2-[2-(4-hydroxynonyl)-5-oxopyrazolidin-1-yl]
ethyl}benzoic acid;
4-(2-{2-[(2Z)-4-hydroxynon-2-enyl]-5-oxopyrazolidin-1-
yl}ethyl)benzoic acid;
4-(2-{2-[(2E)-4-hydroxynon-2-enyl]-5-oxopyrazolidin-1-
yl}ethyl)benzoic acid;
4-{2-[2-(4-hydroxyoctyl)-5-oxopyrazolidin-1-yl]
ethyl}benzoic acid;
4-{2-[2-(4-hydroxy-6-methylheptyl)-5-oxopyrazolidin-1-
yl]ethyl}benzoic acid;
4-{2-[2-(4-hydroxy-5-methyloctyl)-5-oxopyrazolidin-1-yl]
ethyl}benzoic acid;
4-{2-[2-(4-ethyl-4-hydroxyoctyl)-5-oxopyrazolidin-1-yl]
ethyl}benzoic acid;
4-{2-[2-(4-hydroxy-4-methylheptyl)-5-oxopyrazolidin-1-
yl]ethyl}benzoic acid;
4-{2-[2-(4-hydroxy-4,7-dimethyloctyl)-5-oxopyrazolidin-1-
yl]ethyl}benzoic acid;
4-{2-[2-(3-hydroxy-5-methylhexyl)-5-oxopyrazolidin-1-yl]
ethyl}benzoic acid;
4-{2-[2-(3-cyclobutyl-3-hydroxypropyl)-5-oxopyrazolidin-
1-yl]ethyl}benzoic acid;
4-{2-[2-((4S)-hydroxynonyl)-5-oxopyrazolidin-1-yl]
ethyl}benzoic acid;
4-{2-[2-((4R)-hydroxynonyl)-5-oxopyrazolidin-1-yl]
ethyl}benzoic acid
4-[2-(2-{4-[1-(cyclopropylmethyl)cyclobutyl]-4-hydroxy-
butyl}-5-oxopyrazolidin-1-yl)ethyl]benzoic acid;
4-(2-{2-[4-(1-ethylcyclobutyl)-4-hydroxybutyl]-5-oxopyra-
zolidin-1-yl}ethyl)benzoic acid;
4-(2-{2-[3-hydroxy-4-(3-methylphenyl)butyl]-5-oxopyra-
zolidin-1-yl}ethyl)benzoic acid;
4-{2-[2-(3-hydroxy-4-phenylbutyl)-5-oxopyrazolidin-1-yl]
ethyl}benzoic acid;
4-(2-{2-[4-(3-iodophenyl)-3-hydroxybutyl]-5-oxopyrazoli-
din-1-yl}ethyl)benzoic acid;
4-(2-{2-[4-(3-bromophenyl)-3-hydroxybutyl]-5-oxopyrazo-
lidin-1-yl}ethyl)benzoic acid;
4-[2-(2-{3-hydroxy-4-[3-(trifluoromethoxy)phenyl]butyl}-
5-oxopyrazolidin-1-yl)ethyl]benzoic acid;
4-(2-{2-[4-(3-fluorophenyl)-3-hydroxybutyl]-5-oxopyrazo-
lidin-1-yl}ethyl)benzoic acid;
4-[2-(2-{3-hydroxy-4-[3-(trifluoromethyl)phenyl]butyl}-5-
oxopyrazolidin-1-yl)ethyl]benzoic acid;
4-(2-{2-[(3S,4S)-3-hydroxy-4-phenylpentyl]-5-oxopyrazo-
lidin-1-yl}ethyl)benzoic acid;
4-(2-{2-[4-(1,3-benzodioxol-5-yl)-3-hydroxybutyl]-5-ox-
opyrazolidin-1-yl}ethyl)benzoic acid;
4-(2-{2-[4-(3-chlorophenyl)-3-hydroxybutyl]-5-oxopyrazo-
lidin-1-yl}ethyl)benzoic acid;
4-(2-{2-[(4R)-3-hydroxy-4-phenylpentyl]-5-oxopyrazoli-
din-1-yl}ethyl)benzoic acid; and pharmaceutically accept-
able salts thereof.

Compounds of the invention can be readily prepared. Suitable synthetic procedures are exemplified in the following illustrative Schemes 1, 2 and 3. It should be appreciated that the compounds shown in the following Schemes are exemplary only, and a variety of other compounds can be employed in a similar manner as described below. Additionally, while in some instances the Schemes 1, 2 and 3 detail certain preferred reaction conditions, other conditions and reagents may be suitably employed. In Scheme 1, V is H and U suitably has the same meaning as this substituent as defined above for Formulae V or is $R^6$ from formula VI. In the Schemes 2 and 3, substituents V and U suitably have the same meaning as those substituents are defined above for Formulae V or are respectively $R^5$ and $R^6$ from formula VI.

In Scheme 1 below, the protected hydrazine is reacted with an activated aralkyl in the presence of base to provide the substituted hydrazine reagent which can be cyclized to a pyrazolidinone compound upon treatment with a reagent such as 3-halopropionyl chloride in the presence of base.

Other substitutions of the 1-position nuclear nitrogen (i.e. addition of $R^1$ or $R^{1'}$ groups as those groups are specified in the above formulae) can be readily achieved through use of appropriate reagents that will undergo nucleophilic substitution such as an alkyl reagent that has a suitable leaving group e.g. halo, substituted sulfonyl (e.g. mesyl or tosyl), and the like.

Further substitution of the nuclear nitrogens (particularly $R^2$ and $R^{2'}$ groups as those groups are specified in the above formulae) can be accomplished upon appropriate treatment of the thus formed pyrazolidinone, e.g. as shown in Scheme 1, by acidic removal of the nitrogen protecting group (BOC), followed by reaction with a Michael reagent, and reduction of the ketone to a preferred hydroxy alkyl substituent. Other reagents can be employed to provide other substituents of that nuclear nitrogens, e.g. other α,β-unsaturated reagents such as α,β-unsaturated sulfinyls, sulfonyls, nitrites, and the like, which then can be further functionalized as desired.

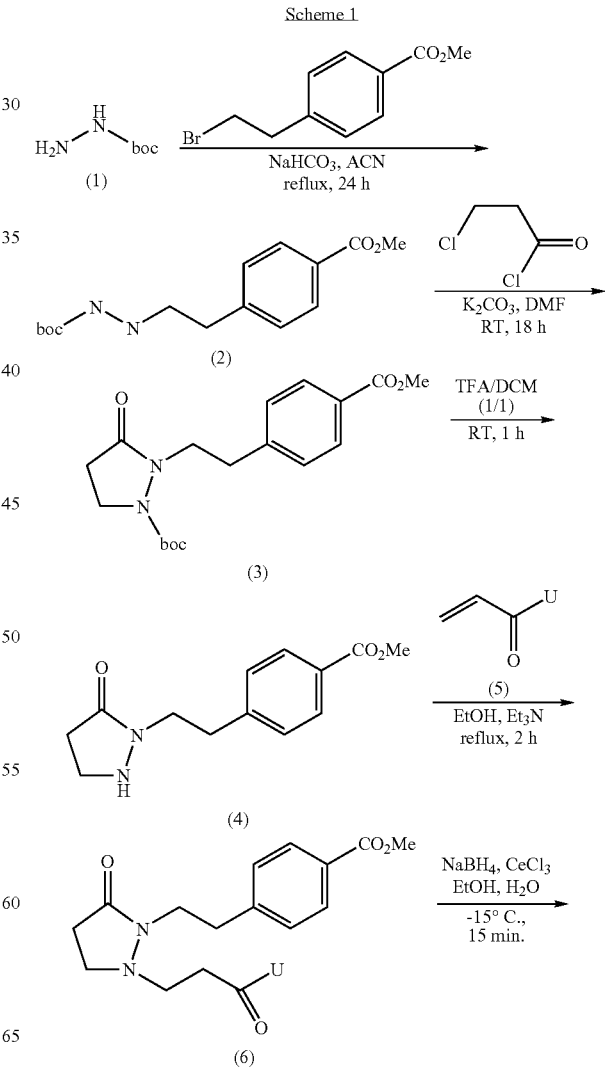

Scheme 1

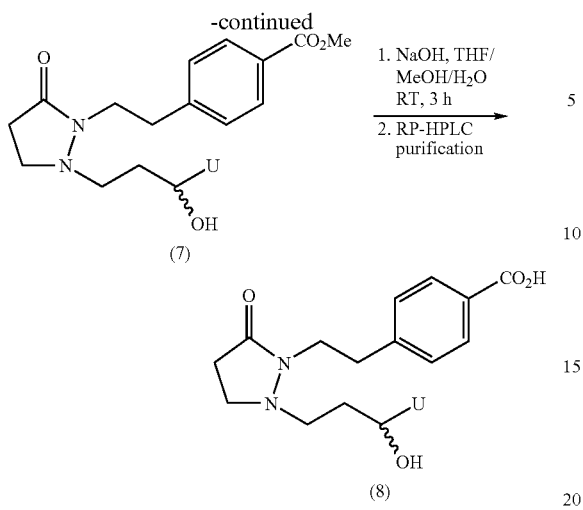

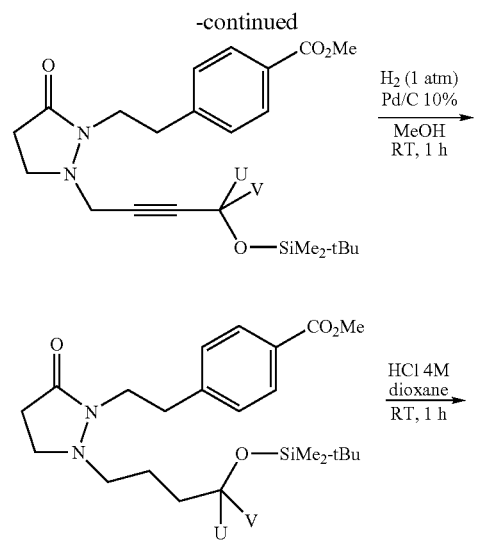

Scheme 2 below depicts an alternate route to compounds of the invention, which includes reaction of the substituted propargyl halide reagent with a pyrazolidinone reagent that has a secondary nuclear nitrogen. The propargyl halide can be grafted onto that ring nitrogen in the presence of base, and the substituted acetylenic group can be further functionalized as desired, e.g. hydrogenated to an alkenylene or alkylene linkage.

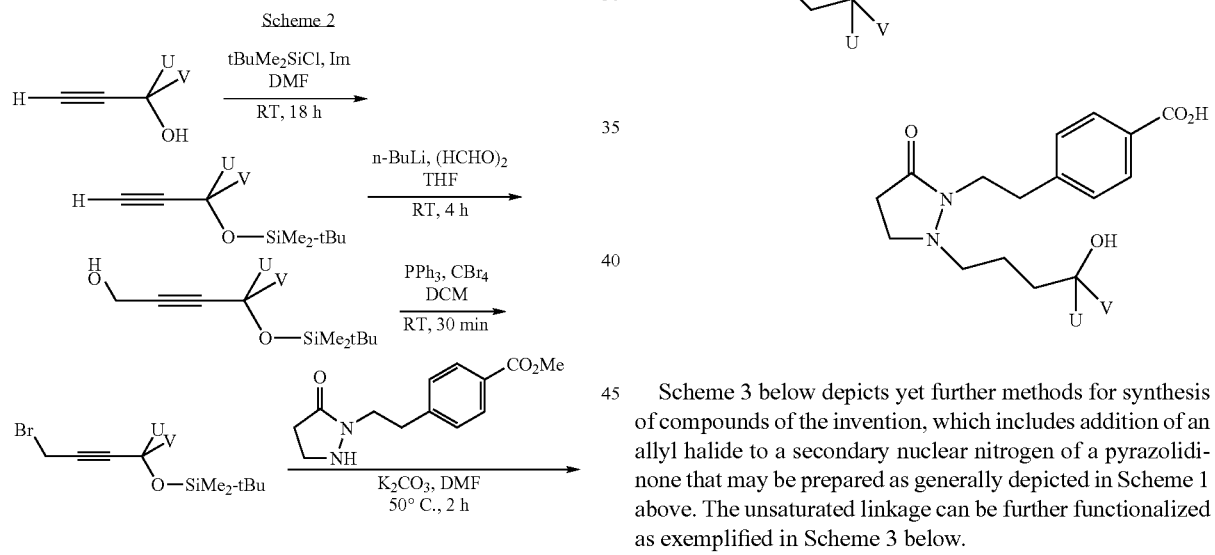

Scheme 3 below depicts yet further methods for synthesis of compounds of the invention, which includes addition of an allyl halide to a secondary nuclear nitrogen of a pyrazolidinone that may be prepared as generally depicted in Scheme 1 above. The unsaturated linkage can be further functionalized as exemplified in Scheme 3 below.

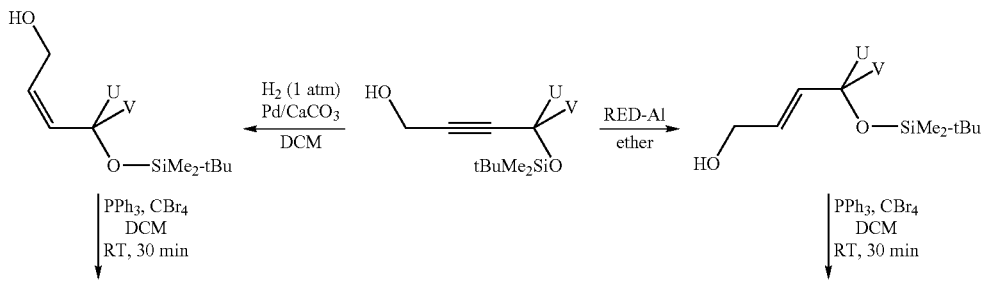

-continued

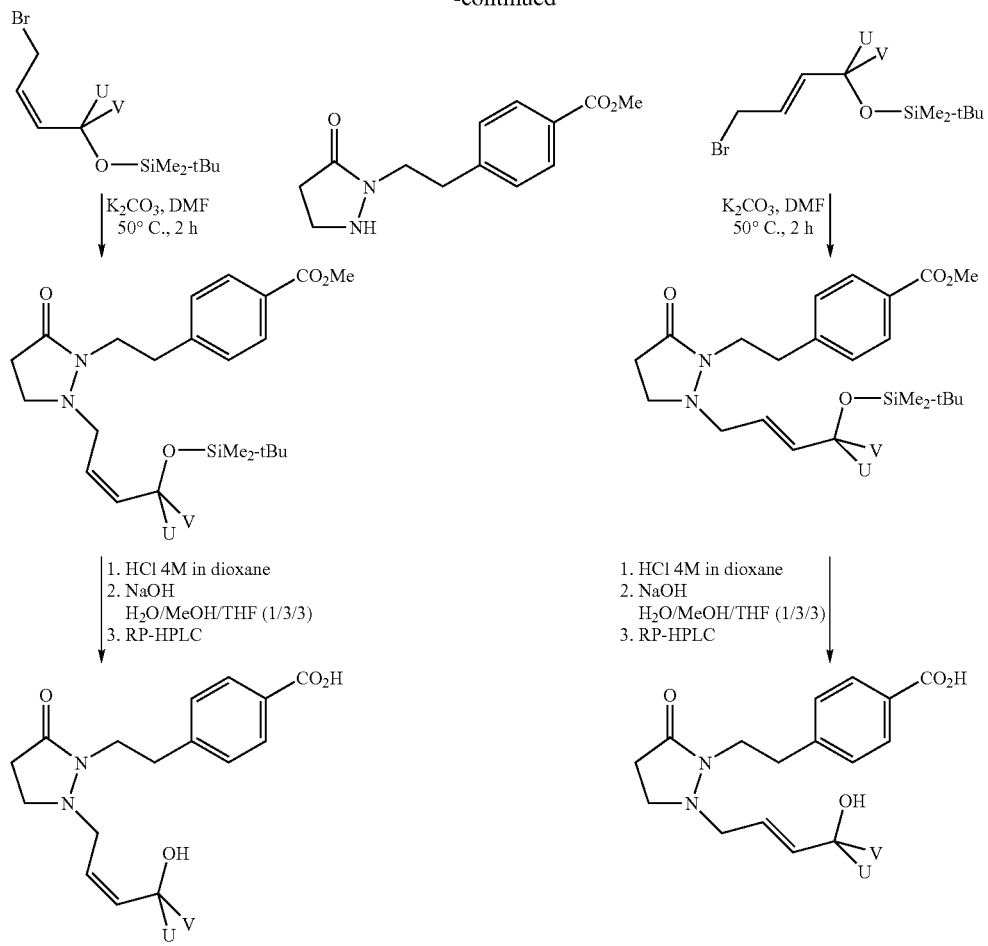

Additional preferred syntheses of compounds of the invention are detailed in the examples which follow.

As discussed above, preferred compounds of the invention exhibit good activity in a standard in vitro EP2 and/or EP4 receptor binding assays. References herein to "standard EP2 and EP4 receptor binding assays" are intended to refer to the protocol as defined in Example 31 and Example 32, which follow. Generally preferred compounds of the invention have a Ki (μM) of about 100 or less, more preferably about 50 or less, still more preferably a Ki (μM) of about 10 or 20 or less, even more preferably a Ki (μM) of about 5 or less in such defined standard EP2 and EP4 receptor binding assays as exemplified by Example 31 and Example 32 which follow.

As indicated above, the present invention includes methods for treating or preventing prostalandin mediated or associated diseases or disorders.

Preferred therapeutic methods of the invention include inhibiting undesired smooth muscle contraction, including undesired prostanoid-induced smooth muscle contraction. Methods of the invention include treatment of a patient suffering from or susceptible to dysmenorrhea, premature labor, asthma and other conditions that can be relieved by bronchodilation, inflammation, hypertension, undesired blood-clotting (e.g. to reduce or prevent thromboses) and other undesired platelet actives, preeclampsia and/or eclampsia and eosinophil-related disorders (eosinophil disorders).

Treatment and/or prevention of undesired blood clotting may include treatment and prophylaxis of venous thrombosis and pulmonary embolism, arterial thrombosis e.g. myocardial ischemia, myocardial infarction, unstable angina, stroke associated with thrombosis, and peripheral arterial thrombosis. Compounds of the invention also may be useful for anti-coagulation involving artificial organs, cardiac valves, medical implementation (e.g. an indwelling device such as a catheter, stent, etc.) and the like.

The invention also includes methods for treatment of infertility, which generally comprise administration of one or more compounds of the invention to a mammal, particularly a primate such as a human, suffering from or suspected of suffering from infertility. See the *Merck Manual*, vol. 2, pages 12-17 (16th ed.) for identification of patients suffering from or suspected of suffering from infertility, which in the case of humans, can include failure to conceive within one year of unprotected intercourse.

The treatment methods of the invention may be particularly beneficial for female mammals suffering from an ovulatory disorder. Additionally, compounds of the invention can be administered to females undergoing assisted reproductive treatments such as in-vitro fertilization, e.g. to stimulate follicular development and maturation, as well as implantation procedures. In particular, treatment methods of the invention may be used in conjunction with in vitro fertilization technology to enhance survival and/or fertilization of a mammalian egg such as in IVF setting.

Treatment methods of the invention also may be employed for control of cervical ripening in late pregnancy (e.g. in humans, late pregnancy would be third trimester, particularly week 30 onward).

Therapeutic methods of the invention also include treatment of glaucoma, inhibition or prevention of bone loss such as to treat osteoporosis, and for promoting bone formation (e.g. to use as a therapy in a bone fracture) and other bone diseases such as Paget's disease.

Compounds of the invention also will be useful to treat sexual dysfunction, including male erectile dysfunction.

The therapeutic methods of the invention generally comprise administration of an effective amount of one or more compounds of the invention to a subject including a mammal, such as a primate, especially a human, in need of such treatment.

Typical candidates for treatment in accordance with the methods of the invention persons suffering from or suspected of suffering from any of the above disorders or diseases, such as a female susceptible or suffering from preterm labor, or a subject suffering from or susceptible to dysmenorrhea or undesired bone loss.

The treatment methods of the invention also will be useful for treatment of mammals other than humans, including for veterinary applications such as to treat horses and livestock e.g. cattle, sheep, cows, goats, swine and the like, and pets such as dogs and cats. Methods of the invention to treat premature labor will be particularly useful for such veterinary applications. Therapeutic methods of the invention also will be useful for treatment of infertility in such veterinary applications.

For diagnostic or research applications, a wide variety of mammals will be suitable subjects including rodents (e.g. mice, rats, hamsters), rabbits, primates and swine such as inbred pigs and the like. Additionally, for in vitro applications, such as in vitro diagnostic and research applications, body fluids (e.g., blood, plasma, serum, cellular interstitial fluid, saliva, feces and urine) and cell and tissue samples of the above subjects will be suitable for use.

Compounds of the invention may be administered as a "cocktail" formulation, i.e. coordinated administration of one or more compounds of the invention together with one or more other active therapeutics, particularly one or more other known fertility agents. For instance, one or more compounds of the invention may be administered in coordination with a regime of a pain relief agent, an anti-inflammatory agent, or an anti-cogulant, depending on the indication being treated. Suitable anti-coagulants for such coordinated drug therapies include e.g. warfarin, heparin, hirudin or hirulog or an anti-platelet such as ReoPro.

For treatment of fertility disorders, one or more compounds of the invention may be suitably administered in coordination with one or more known fertility agents such as Follicle Stimulating and/or Leutinizing Hormone such as Gonal-F, Metrodin HP or Pergonal, for simultaneous, sequential or separate use.

In certain preferred aspects of the invention, particularly compositional aspects of the invention, less preferred and hence excluded from such aspects are compounds of Formula V as defined above where G is $CH_2$; n' is 3; E is hydrogen and p is 2; $R^4$ is hydrogen and o is 2; n" is 2; n''' is zero; and/or V is alkyl.

Compounds of the invention can be administered by a variety of routes, such as orally or by injection, e.g., intramuscular, intraperitoneal, subcutaneous or intravenous injection, or topically such as transdermally, vaginally and the like. Compounds of the invention may be suitably administered to a subject in the protonated and water-soluble form, e.g., as a pharmaceutically acceptable salt of an organic or inorganic acid, e.g., hydrochloride, sulfate, hemi-sulfate, phosphate, nitrate, acetate, oxalate, citrate, maleate, mesylate, etc. If the compound has an acidic group, e.g. a carboxy group, base additional salts may be prepared. Lists of additional suitable salts may be found in Part 5 of *Remington's Pharmaceutical Sciences*, 20$^{th}$ Edition, 2000, Marck Publishing Company, Easton, Pa.

Compounds of the invention can be employed, either alone or in combination with one or more other therapeutic agents as discussed above, as a pharmaceutical composition in mixture with conventional excipient, i.e., pharmaceutically acceptable organic or inorganic carrier substances suitable for oral, parenteral, enteral or topical application which do not deleteriously react with the active compounds and are not deleterious to the recipient thereof. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

Pharmaceutical compositions of the invention include a compound of the invention packaged together with instructions (written) for therapeutic use of the compound to treat e.g. premature labor, dysmenorrhea or asthma, or other disorder as disclosed herein, such as a disease or disorder associated with or mediated by the prostaglandin EP2 and/or EP4 receptors.

For oral administration, pharmaceutical compositions containing one or more substituted pyrazolidinone compounds of the invention may be formulated as e.g. tablets, troches, lozenges, aqueous or oily suspensions, dispersible powders or granules, emulsions, hard or soft capsules, syrups, elixers and the like. Typically suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

For parenteral application, e.g., sub-cutaneous, intraperitoneal or intramuscular, particularly suitable are solutions, preferably oily or aqueous solutions as well as suspensions, emulsions, or implants, including suppositories. Ampules are convenient unit dosages.

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines. See also *Remington's Pharmaceutical Sciences*, supra. In general, a suitable effective dose of one or more compounds of the invention, particularly when using the more potent compound(s) of the invention, will be in the range of from 0.01 to 100 milligrams per kilogram of bodyweight of recipient per day, preferably in the range of from 0.01 to 20 milligrams per kilogram bodyweight of recipient per day, more preferably in the range of 0.05 to 4 milligrams per kilogram bodyweight of recipient per day. The desired dose is suitably administered once daily, or several sub-doses, e.g. 2 to 4 sub-doses, are administered at appropriate intervals through the day, or other appropriate schedule. Such sub-doses may be administered as unit dosage forms, e.g., containing from 0.05 to 10 milligrams of compound(s) of the invention, per unit dosage.

The entire text of all documents cited herein are incorporated by reference herein. The following non-limiting examples are illustrative of the invention.

EXAMPLES 1-30

Syntheses of Compounds of the Invention

Example 1

Synthesis of 4-[2-(2-(3-hydroxyoctyl)-5-oxopyrazolidin-1-yl)ethyl]benzoic acid

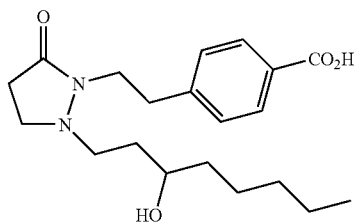

Intermediate 1.1: Methyl 4-(bromoethyl)benzoate

A 2 M solution in hexane of trimethylsilyldiazomethane (0.072 mol, 36 mL) was added dropwise to a solution of 4-(bromoethyl)benzoic acid (15 g, 0.065 mol) in DCM (150 mL) and MeOH (36 mL). The resulting solution was stirred at RT for 2 h then was concentrated under reduced pressure to afford the title compound (15.8 g, 98%) as a pale yellow oil. $^1$H NMR (CDCl$_3$) δ 3.2 (t, 2H), 3.6 (t, 2H), 3.9 (s, 3H), 7.3 (d, 2H), 8.0 (d, 2H).

Intermediate 1.2: tert-Butyl 2-[2-(4-(methoxycarbonyl)phenyl)ethyl]hydrazine carboxylate.

To a solution of Intermediate 1.1 (15.6 g, 0.065 mol) in acetonitrile (150 mL) were added tert-butyl carbazate (8.6 g, 0.065 mol), NaHCO$_3$ (22.0 g, 0.26 mol) and a catalytic amount of NaI. The resulting mixture was refluxed for 24 h then concentrated under reduced pressure. The crude residue was diluted with EtOAc (200 mL) and washed with water (200 mL), brine (200 mL), dried over sodium sulfate and concentrated in vacuo. The crude residue was purified by flash column chromatography using EtOAc/hexanes as eluant to afford the title compound (5.5 g, 30%) as a white solid. R$_f$ 0.5 (EtOAc/hexanes 1/1); $^1$H NMR (CDCl$_3$) δ 1.44 (s, 9H), 2.85 (t, J=7.3 Hz, 2H), 3.15 (t, J=7.3 Hz, 2H), 3.89 (s, 3H), 7.29 (d, J=7.0 Hz, 2H), 7.95 (d, J=7.0 Hz, 2H).

Intermediate 1.3: tert-Butyl 2-[2-(4-(methoxycarbonyl)phenyl)ethyl]-3-oxopyrazolidine-1-carboxylate.

To a solution of Intermediate 1.2 (1.7 g, 5.77 mmol) in DMF (30 mL) were added K$_2$CO$_3$ (1.6 g, 11.5 mmol) and chloro propyonyl chloride (0.55 mL, 5.77 mmol). The resulting mixture was stirred at RT for 18 h then was diluted with EtOAc (100 mL) and washed with water (2×100 mL) and brine (100 mL). The organic solution was dried and concentrated under reduced pressure. The crude mixture was purified by flash column chromatography using EtOAc/hexanes as eluant to afford the title compound (1.1 g, 55%) as a colorless oil. R$_f$ 0.4 (EtOAc/hexanes 1/1); $^1$H NMR (CDCl$_3$) δ 1.5 (s, 9H), 2.4 (t, 2H), 2.95 (d, 2H), 3.72 (t, 2H), 3.90 (s, 3H), 4.05 (t, 2H), 7.29 (d, J=7.0 Hz, 2H), 7.95 (d, J=7.0 Hz, 2H).

Intermediate 1.4: Methyl 4-[2-(5-oxopyrazolidin-1-yl)ethyl]benzoate.

The Intermediate 1.3 (1.0 g, 0.0028 mol) was taken in DCM (5 mL) and treated with TFA (5 mL). The resulting solution was stirred at RT for 1 h then concentrated under reduced pressure. The crude oil was diluted with EtAOc (50 mL) and washed with a saturated solution of NaHCO$_3$ (50 mL), brine (50 mL), dried and concentrated to afford the title compound (0.61 g, 88%) as a yellow solid. $^1$H NMR (CDCl$_3$) δ 2.48 (t, J=7.7 Hz, 2H), 2.98 (t, J=7.3 Hz, 2H), 3.29 (t, J=6.8 Hz, 2H), 3.73 (t, J=6.9 Hz, 2H), 3.89 (s, 3H), 7.29 (d, J=7.0 Hz, 2H), 7.96 (d, J=7.0 Hz, 2H); MS (m/z) 249 (M+1).

Intermediate 1.5: Methyl 4-[2-(5-oxo-2-(3-oxooctyl)pyrazolidin-1-yl)ethyl]-benzoate.

To a solution of the Intermediate 1.4 (0.46 g, 1.86 mmol) in iPrOH were added Et$_3$N (1.3 mL, 9.3 mmol) and 1-octene-3-one (0.83 mL, 5.6 mmol). The resulting solution was stirred at reflux for 2 h then concentrated in vacuo and the crude oil purified by flash column chromatography (EtOAc/hexanes) to afford the title compound (0.50 g, 72%) as a colorless oil. R$_f$ 0.2 (EtOAc); $^1$H NMR (CDCl$_3$) δ 0.89 (t, J=5.1 Hz, 3H), 1.20-1.40 (m, 4H), 1.52-1.60 (m, 2H), 2.42 (t, J=7.3 Hz, 2H), 2.30-2.60 (m, 4H), 2.92 (t, J=7.3 Hz, 2H), 2.90-3.20 (m, 4H), 3.4-3.9 (m, 2H), 3.89 (s, 3H), 7.29 (d, J=6.7 Hz, 2H), 7.93 (d, J=6.7 Hz, 2H); MS (m/z) 375 (M+1).

Intermediate 1.6: Methyl 4-{2-[2-(3-hydroxyoctyl)-5-oxopyrazolidin-1-yl]ethyl}benzoate.

To a solution of Intermediate 1.5 (0.50 g, 1.34 mmol) in EtOH (6 mL) and water (10 mL) cooled at −15° C. were added CeCl$_3$ (0.33 g, 1.34 mmol) followed by NaBH$_4$ (0.076 g, 2 mmol). After 10 minutes the reaction was diluted with EtAOc (50 mL) and washed with water (50 mL), brine (50 mL), dried and concentrated in vacuo to afford the crude compound (0.5 g, 98%) used in the next without further purification. R$_f$ 0.15 (EtOAc); MS (m/z) 377.4 (M+1).

The title compound, 4-[2-(2-(3-hydroxyoctyl)-5-oxopyrazolidin-1-yl)ethyl]benzoic acid (Example 1), was then prepared as follows. To a solution of Intermediate 1.6 (200 mg, 0.53 mmol) in water (2 mL), MeOH (6 mL), and THF (6 mL) was added NaOH (64 mg, 1.6 mmol). The resulting solution was stirred at RT for 8 h then concentrated under reduced pressure. The crude mixture was purified by RP-HPLC using ACN/H$_2$O/and 0.1% TFA to afford the desired compound (150 mg, 60%) as a colorless oil. $^1$H NMR (CD$_3$OD) δ 0.91 (t, 3H), 1.15-1.75 (m, 10H), 2.2-2.8 (m, 2H), 2.85-3.05 (m, 4H), 3.20-3.45 (m, 6H), 3.6-3.8 (m, 2H), 7.34 (d, J=8.0 Hz, 2H), 7.95 (d, J=8.0 Hz, 2H), MS (m/z) 362 (M+1).

Example 2

Synthesis of 4-{2-[2-(4-hydroxynon-2-ynyl)-5-oxopyrazolidin-1-yl]ethyl}benzoic acid

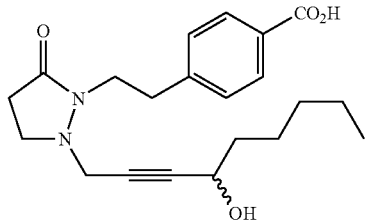

Intermediate 2.1: tert-Butyl(dimethyl)[(1-pentylprop-2-ynyl)oxy]silane.

To a solution of 1-octyn-3-ol (5.0 g, 0.039 mol) in DMF (50 mL) were added tert-butyldimethylsilyl chloride (7.16 g, 0.0475 mol) and imidazole (3.2 g, 0.0475 mol). The resulting solution was stirred at RT for 18 h then diluted with ether (200 mL) and washed with water (2×200 mL), saturated solution of $NH_4Cl$ (200 mL), and brine (200 mL). The organic solution was dried over sodium sulfate and concentrated in vacuo to afford the desired compound (9.0 g, 95%) as a colorless oil used in the next step without further purification. $R_f$ 0.9 (EtOAc/hexanes 1/9); $^1$H NMR (CDCl$_3$) δ 0.09 (s, 3H), 0.12 (s, 3H), 0.89 (s, 9H), 0.85-1.00 (t, 3H), 1.20-1.70 (m, 8H), 2.35 (s, 1H), 4.30-4.35 (m, 1H).

Intermediate 2.2: 4-{[tert-Butyl(dimethyl)silyl]oxy}non-2-yn-1-ol.

To a solution of Intermediate 2.1 (0.50 g, 2.08 mmol) in dry THF (15 mL) cooled at −70° C. was added dropwise a 1.6M solution of n-BuLi in hexanes (1.36 mL, 2.18 mmol). The resulting solution was stirred at −70° C. for 10 minutes then paraformaldehyde (0.16 g, 5.46 mmol) was added. The resulting mixture was stirred at RT for 4 h then was diluted with EtOAc (100 mL) and washed with a saturated solution of $NH_4Cl$ (100 mL), brine (100 mL), dried and concentrated in vacuo. The crude residue was purified by flash column chromatography (EtOAc/hexanes) to afford the title compound (0.42 g, 75%) as a colorless oil. $R_f$ 0.3 (EtOAc/hexanes 1/9); $^1$H NMR (CDCl$_3$) δ 0.09 (s, 3H), 0.11 (s, 3H), 0.89 (s, 9H), 0.85-0.90 (t, 3H), 1.20-1.70 (m, 8H), 4.27 (s, 2H), 4.30-4.40 (m, 1H).

Intermediate 2.3: [(4-Bromo-1-pentylbut-2-ynyl)oxy](tert-butyl)dimethylsilane.

To a solution of Intermediate 2.2 (0.42 g, 1.55 mmol) in DCM (10 mL) were added PPh$_3$ (0.49 g, 1.86 mmol) and CBr$_4$ (0.62 g, 1.86 mmol). The resulting solution was stirred at RT for 1 h then concentrated in vacuo and the crude residue was purified by flash column chromatography (EtOAc/hexanes 0.5/9.5) to afford the desired compound (0.55 g, 99%) as a colorless oil. $R_f$ 0.9 (EtOAc/hexanes 1/9); $^1$H NMR (CDCl$_3$) δ0.09 (s, 3H), 0.11 (s, 3H), 0.89 (s, 9H), 0.85-0.90 (t, 3H), 1.20-1.70 (m, 8H), 3.92 (s, 2H), 4.33-4.43 (m, 1H).

Intermediate 2.4: Methyl 4{2-[2-(4-{[tert-butyl(dimethyl)silyl]oxy}non-2-ynyl)-5-oxopyrazolidin-1-yl]ethyl}benzoate.

To a solution of Intermediate 1.4 (0.3 g, 1.2 mmol) in DMF (10 mL) were added Intermediate 2.3 (0.50 g, 1.55 mmol), $K_2CO_3$ (0.33 g, 2.38 mmol), and a catalytic amount of NaI. The resulting mixture was stirred at 50° C. for 2 h then was diluted with EtOAc (50 mL) and washed with water (50 mL) and brine (50 mL). The organic solution was dried over sodium sulfate and concentrated in vacuo. The crude mixture was purified by silica gel column chromatography (EtOAc/hexanes) to yield the title compound (0.25 g, 45%) as a colorless oil. $R_f$ 0.5 (EtOAc/hexanes 1/1); $^1$H NMR (CDCl$_3$) δ 0.09 (s, 3H), 0.11 (s, 3H), 0.88 (s, 9H), 0.8-1.00 (m, 3H), 1.20-1.45 (m, 9H), 1.55-1.70 (m, 2H), 2.85-3.00 (m, 3H), 3.20-3.43 (m, 2H), 3.50-3.60 (m, 2H), 3.89 (s, 3H), 4.25-4.35 (m, 1H), 7.26 (d, J=8.1 Hz, 2H), 7.96 (d, J=8.1 Hz, 2H); MS (m/z) 501.2 (M+1).

Intermediate 2.5: Methyl 4-{2-[2-(4-hydroxynon-2-ynyl)-5-oxopyrazolidin-1-yl]ethyl}benzoate.

Intermediate 2.4 (45 mg, 0.09 mmol) was dissolved in a 4M HCl solution in dioxane (4 mL). The resulting solution was stirred at RT for 1 h then was concentrated in vacuo to afford the title compound (40 mg) used in the next step without further purification. MS (m/z) 387 (M+1).

The title compound, 4-{2-[2-(4-hydroxynon-2-ynyl)-5-oxopyrazolidin-1-yl]ethyl}benzoic acid (Example 2), was prepared from Intermediate 2.5 as described in Example 1 to provide the title compound (20 mg, 50%) was obtained as a colorless viscous oil. $^1$H NMR (acetone-d$_6$) δ 0.87 (t, J=7.0 Hz, 3H), 1.20-1.70 (m, 8H), 2.90-3.00 (m, 2H), 3.30-3.45 (m, 2H), 3.60-4.00 (m, 4H), 4.32 (t, J=6.6 Hz, 1H), 7.38 (d, J=8.4 Hz, 2H), 8.00 (d, J=8.4 Hz, 2H); MS (m/z) 373 (M+1).

Example 3

Synthesis of 4-{2-[2-(4-hydroxynonyl)-5-oxopyrazolidin-1-yl]ethyl}benzoic acid

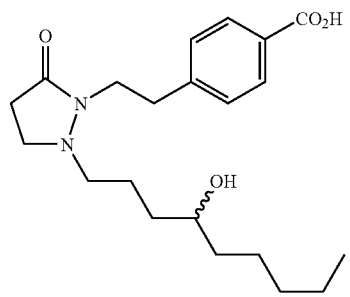

Intermediate 3.1: Methyl 4-{2-[2-(4-{[tert-butyl(dimethyl)silyl]oxy}nonyl)-5-oxo pyrazolidin-1-yl]ethyl}benzoate.

A mixture of Intermediate 2.4 (80 mg, 0.16 mmol) and 10% Palladium on carbon (10 mg) in MeOH (5 mL) was stirred under hydrogen atmosphere (1 atm) for 1 h. The mixture was filtered through celite and concentrated in vacuo to afford the title compound (80 mg, 98%) as a colorless oil. MS (m/z) 505.5 (M+1).

Intermediate 3.2: Methyl 4-{2-[2-(4-hydroxynonyl)-5-oxopyrazolidin-1-yl)-ethyl]-benzoate Intermediate 3.1 (80 mg, 0.16 mmol) was dissolved in a 4M HCl solution in dioxane (4 mL). The resulting solution was stirred at RT for 1 h then was concentrated in vacuo to afford the title compound (50 mg) used in the next step without further purification. MS (m/z) 391 (M+1).

The title compound, 4-{2-[2-(4-hydroxynonyl)-5-oxopyrazolidin-1-yl]ethyl}benzoic acid (Example 3), was then prepared as from Intermediate 3.2 as described to prepare the compound of Example 1, to provide 4-{2-[2-(4-hydroxynonyl)-5-oxopyrazolidin-1-yl]ethyl}benzoic acid (35 mg, 45%) as a colorless viscous oil. $^1$H NMR (acetone-d$_6$) δ 0.87

(J=7.0 Hz, 3H), 1.20-1.80 (m, 12H), 2.50-3.05 (m, 6H), 3.20-3.80 (m, 4H), 7.39 (d, J=8.4 Hz, 2H), 7.90 (d, J=8.4 Hz, 2H), 8.4 (br s, 2H); MS (m/z) 377.5 (M+1).

Example 4

Synthesis of 4-(2-{2-[(2Z)-4-hydroxynon-2-enyl]-5-oxopyrazolidin-1-yl}ethyl)benzoic acid

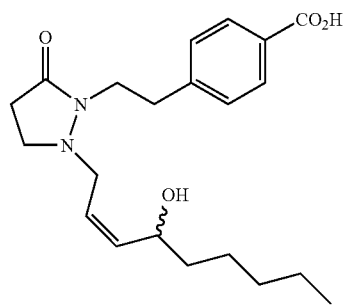

Intermediate 4.1: (2Z)-4-{[tert-Butyl(dimethyl)silyl]oxy}non-2-en-1-ol.

A mixture of Intermediate 2.2 (100 mg) and Pd/CaCO$_3$ (10 mg) in DCM (5 mL) was hydrogenated at 1 atm for 3 h then filtered through celite and concentrated in vacuo to afford the desired Intermediate (98 mg, 98%) as a colorless oil. R$_f$ 0.3 (EtOAc/hexanes 1/9); $^1$H NMR (CDCl$_3$) δ 0.09 (s, 3H), 0.12 (s, 3H), 0.89 (s, 9H), 0.85-1.00 (t, 3H), 1.20-1.80 (m, 8H), 4.12 (dd, J=5.1 and 10.1 Hz, 1H), 4.22 (dd, J=6.2 and 10.1 Hz, 1H), 4.35 (dd, J=5.1 and 6.6, 1H), 5.4-5.6 (m, 1H).

Intermediate 4.2: {[(2Z)-4-Bromo-1-pentylbut-2-enyl]oxy}(tert-butyl)dimethyl)silane.

To a solution of Intermediate 4.1 (420 mg, 1.54 mmol) in dry DCM (15 mL) were added PPh$_3$ (490 mg, 1.86 mmol) and CBr$_4$ (617 mg, 1.86 mmol). The resulting solution was stirred at RT for 1 h then concentrated in vacuo. The crude residue was purified by flash chromatography (EtOAc/hexanes 0.5/9.5) to afford the desired Intermediate (510 mg, 97%) as a colorless oil. R$_f$ 0.9 (EtOAc/hexanes 1/9); $^1$H NMR (CDCl$_3$) δ 0.09 (s, 3H), 0.12 (s, 3H), 0.89 (s, 9H), 0.85-1.00 (t, 3H), 1.20-1.60 (m, 8H), 3.90-4.05 (m, 2H), 4.40-4.50 (m, 1H), 4.45-4.52 (m, 1H), 4.58-4.70 (m, 1H).

Intermediate 4.3: Methyl 4-{2-[2-((2Z)-4-{[tert-butyl(dimethyl)silyl]oxy}non-2-enyl)-5-oxopyrazolidin-1-yl]ethyl}benzoate.

To a solution of Intermediate 1.4 (140 mg, 0.56 mmol) in DMF (6 mL) were added Intermediate 4.2 (250 mg, 0.75 mmol), K$_2$CO$_3$ (500 mg, 3.61 mmol), and a catalytic amount of NaI. The resulting mixture was stirred at 50° C. for 2 h then was diluted with EtOAc (50 mL) and washed with water (50 mL) and brine (50 mL). The organic solution was dried over sodium sulfate and concentrated in vacuo. The crude mixture was purified by silica gel column chromatography (EtOAc/hexanes) to yield the title compound (85 mg, 30%) as a colorless oil. R$_f$ 0.6 (EtOAc/hexanes 1/1); $^1$H NMR (CDCl$_3$) δ 0.09 (s, 3H), 0.11 (s, 3H), 0.88 (s, 9H), 0.8-1.00 (m, 3H), 1.20-1.45 (m, 10H), 2.90-3.00 (m, 3H), 3.10-3.24 (m, 2H), 3.30-3.45 (m, 2H), 3.90 (m, 3H), 4.30-4.40 (m, 1H), 5.35-5.45 (m, 1H), 5.55-5.70 (m, 1H), 7.28 (d, J=8.0 Hz, 2H), 7.94 (d, J=8.0 Hz, 2H); MS (m/z) 503 (M+1).

Intermediate 4.4: Methyl 4-(2-{2-[(2Z)-4-hydroxynon-2-enyl]-5-oxopyrazolidin-1-yl}ethyl)benzoate.

Intermediate 4.3 (80 mg, 0.159 mmol) was dissolved in a 4M HCl solution in dioxane (4 mL). The resulting solution was stirred at RT for 1 h then was concentrated in vacuo to afford the title compound (70 mg) used in the next step without further purification. MS (m/z) 389.2 (M+1).

The title compound, 4-(2-{2-[(2Z)-4-hydroxynon-2-enyl]-5-oxopyrazolidin-1-yl}ethyl)benzoic acid (Example 4), was prepared from Intermediate 4.4 according to the procedure of Example 1, to provide 4-(2-{2-[(2Z)-4-hydroxynon-2-enyl]-5-oxopyrazolidin-1-yl}ethyl)benzoic acid as a colorless viscous oil. $^1$H NMR (methanol-d$_4$) δ 0.85-0.95 (t, 3H), 1.20-1.70 (m, 8H), 2.90-3.00 (m, 2H), 3.20-3.30 (m, 2H), 3.45-3.55 (m, 2H), 3.30-3.40 (m, 1H), 5.50-5.70 (m, 2H), 7.38 (d, J=8.4 Hz, 2H), 7.95 (d, J=8.4 Hz, 2H); MS (m/z) 375 (M+1).

Example 5

Synthesis of 4-(2-{2-[(2E)-4-hydroxynon-2-enyl]-5-oxopyrazolidin-1-yl}ethyl)benzoic acid

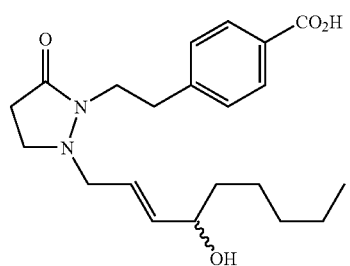

Intermediate 5.1: (2E)-4-{[tert-Butyl(dimethyl)silyl]oxy}non-2-en-1-ol.

To a solution of the Intermediate 2.2 (200 mg, 0.74 mmol) in dry ether (5 mL) was added dropwise at 0° C. a 65% Red-Al solution in toluene (0.28 mL, 0.88 mmol). The resulting solution was stirred at 0° C. for 4 h and 15 min. at RT. The reaction was quenched by the addition of a saturated solution of Rochelle salt (40 mL) and extracted with EtOAc (50 mL). The organic solution was washed with brine (50 mL), dried and concentrated in vacuo to afford the desired Intermediate (750 mg, 95%) as a colorless oil. R$_f$ 0.3 (EtOAc/hexanes 1/9); $^1$H NMR (CDCl$_3$) δ 0.09 (s, 3H), 0.12 (s, 3H), 0.89 (s, 9H), 0.85-1.00 (t, 3H), 1.20-1.50 (m, 8H), 4.10-4.20 (m, 3H) 5.60-5.82 (m, 2H).

Intermediate 5.2: {[(2E)-4-Bromo-1-pentylbut-2-enyl]oxy}(tert-butyl)dimethyl)silane.

To a solution of Intermediate 5.1 (750 mg, 2.77 mmol) in dry DCM (15 mL) were added PPh$_3$ (800 mg, 3.04 mmol) and CBr$_4$ (1010 mg, 3.04 mmol). The resulting solution was stirred at RT for 1 h then concentrated in vacuo. The crude residue was purified by flash chromatography (EtOAc/hexanes 0.5/9.5) to afford the desired Intermediate (460 mg, 50%) as a colorless oil. R$_f$ 0.9 (EtOAc/hexanes 1/9); $^1$H NMR (CDCl$_3$) δ 0.09 (s, 3H), 0.12 (s, 3H), 0.90 (s, 9H), 0.85-0.95 (t, 3H), 1.20-1.60 (m, 8H), 3.95 (d, J=7.4 Hz, 2H), 4.10-4.20 (m, 1H), 4.65-4.90 (m, 2H), 4.58-4.70 (m, 1H).

Intermediate 5.3: Methyl 4-{2-[2-((2Z)-4-{[tert-butyl(dimethyl)silyl]oxy}non-2-enyl)-5-oxopyrazolidin-1-yl]ethyl}benzoate.

To a solution of Intermediate 1.4 (100 mg, 0.40 mmol) in DMF (5 mL) were added Intermediate 5.2 (200 mg, 0.60 mmol), K$_2$CO$_3$ (140 mg, 1.01 mmol), and a catalytic amount of NaI. The resulting mixture was stirred at 50° C. for 2 h then was diluted with EtOAc (50 mL) and washed with water (50 mL) and brine (50 mL). The organic solution was dried over sodium sulfate and concentrated in vacuo. The crude mixture was purified by silica gel column chromatography (EtOAc/hexanes) to yield the title compound (120 mg, 60%) as a colorless oil. $R_f$ 0.4 (EtOAc/hexanes 1/1); $^1$H NMR (CDCl$_3$) δ 0.09 (s, 3H), 0.11 (s, 3H), 0.88 (s, 9H), 0.8-1.00 (m, 3H), 1.20-1.60 (m, 10H), 2.90-3.00 (m, 3H), 3.10-3.25 (m, 2H), 3.30-3.45 (m, 2H), 3.89 (s, 3H), 4.05-4.15 (m, 1H), 4.55-4.72 (m, 2H), 7.31 (d, J=8.0 Hz, 2H), 7.94 (d, J=8.0 Hz, 2H); MS (m/z) 503 (M+1).

Intermediate 5.4: Methyl 4-(2-{2-[(2E)-4-hydroxynon-2-enyl]-5-oxopyrazolidin-1-yl}ethyl)benzoate.

Intermediate 5.3 (120 mg, 0.24 mmol) was dissolved in a 4M HCl solution in dioxane (4 mL). The resulting solution was stirred at RT for 1 h then was concentrated in vacuo to afford the title compound (80 mg, 86%) used in the next step without further purification. MS (m/z) 389.2 (M+1).

The title compound, 4-(2-{2-[(2E)-4-hydroxynon-2-enyl]-5-oxopyrazolidin-1-yl}ethyl)benzoic acid (Example 5), was prepared from Intermediate 5.4 as described in Example 1 above, to provide 4-(2-{2-[(2E)-4-hydroxynon-2-enyl]-5-oxopyrazolidin-1-yl}ethyl)benzoic acid (50 mg, 56%) as a colorless viscous oil. $^1$H NMR (methanol-d$_4$) δ 0.85-0.95 (m, 3H), 1.20-1.60 (m, 8H), 2.20-2.80 (m, 2H), 2.90-3.05 (m, 2H), 3.40-3.90 (m, 4H), 3.95-4.10 (m, 1H), 5.60-5.80 (m, 2H), 7.38 (d, J=8.4 Hz, 2H), 7.95 (d, J=8.4 Hz, 2H); MS (m/z) 375 (M+1).

Example 6

Synthesis of 4-{2-[2-(4-hydroxyoctyl)-5-oxopyrazolidin-1-yl]ethyl}benzoic acid

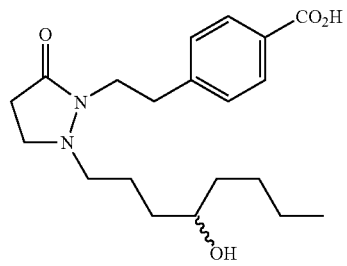

Intermediate 6.1: tert-Butyl[(1-butylprop-2-ynyl)oxy]dimethylsilane.

To a solution of hept-1-yn-3-ol (5.0 g, 0.0446 mol) in dry DMF (50 mL) were added imidazole (3.64 g, 0.054 mol) and tert-butyldimethylsilyl chloride (6.06 g, 0.054 mol). The resulting mixture was stirred at RT for 18 h and then treated with saturated NH$_4$Cl (25 mL) and ethyl acetate (250 mL). The organic layer was washed with saturated NH$_4$Cl (50 mL), water (4×100 mL), brine (2×100 mL), dried over sodium sulfate, and concentrated in vacuo to afford the crude product (9.57 g, 95%), as a yellow oil, which was used in the next step without further purification. $R_f$ 0.9 (EtOAc/hexanes 1/9); $^1$H NMR (CDCl$_3$) δ 0.09 (s, 3H), 0.12 (s, 3H), 0.89 (s, 9H), 1.31-1.38 (m, 4H), 1.65-1.67 (m, 2H), 3.35 (s, 1H), 4.32-4.33 (m, 1H).

Intermediate 6.2: 4-(tert-Butyl-dimethyl-silanyloxy)-oct-2-yn-1-ol.

An oven-dried flask was charged with a solution of intermediate 6.1 (4.14 g, 0.018 mol) in THF (180 mL, 0.1 M) under nitrogen atmosphere. The solution was cooled to −70° C., in an acetone-dry ice bath, and then a 1.6 M solution of n-BuLi in hexanes (14 mL, 0.022 mol) was added, dropwise, over 15 minutes. The mixture was stirred for further 0.5 h, when solid paraformaldehyde (2.2 g, 0.073 mol) was added, in one portion, under nitrogen atmosphere. The stirring was continued for further 10 minutes, and then the cooling bath removed. The resulting solution was allowed to react at RT for 18 hr and then treated with saturated NH$_4$Cl (100 mL) and ethyl acetate (300 mL). The organic layer was washed with saturated NH$_4$Cl (2×100 mL), water (2×100 mL), brine (200 mL), dried over sodium sulfate, and concentrated in vacuo to give a yellow oily residue. The residue was purified by flash column chromatography (EtOAc/hexanes, 1/9) to give the desired product (4.02 g, 86%) as a colorless oil. $R_f$ 0.16 (EtOAc/hexanes 1/9); $^1$H NMR (CDCl$_3$) δ 0.09 (s, 3H), 0.11 (s, 3H), 0.88 (s, 3H), 0.89 (s, 9H), 1.40-1.26 (m, 4H), 1.6-1.61 (m, 2H), 4.27 (d, J=1.8 Hz, 2H), 4.37-4.34 (m, 1H).

Intermediate 6.3: [(4-Bromo-1-butylbut-2-ynyl)oxy](tert-butyl)dimethylsilane.

To a solution of Intermediate 6.2 (0.60 g, 2.34 mmol) in DCM (15 mL) were added PPh$_3$ (0.74 g, 2.80 mmol) and CBr$_4$ (0.93 g, 2.80 mmol). The resulting solution was stirred at RT for 1 h then concentrated in vacuo and the crude residue was purified by flash column chromatography (EtOAc/hexanes 0.5/9.5) to afford the desired compound (0.60 g, 80%) as a colorless oil. $R_f$ 0.9 (EtOAc/hexanes 1/9); $^1$H NMR (CDCl$_3$) δ 0.10 (s, 3H), 0.12 (s, 3H), 0.89 (s, 9H), 0.85-0.90 (m, 3H), 1.25-1.45 (m, 4H), 1.60-1.70 (m, 2H), 3.92 (s, 2H), 4.35-4.42 (m, 1H).

Intermediate 6.4: Methyl 4{2-[2-(4-{[tert-butyl(dimethyl)silyl]oxy}oct-2-ynyl)-5-oxopyrazolidin-1-yl]ethyl}benzoate.

To a solution of Intermediate 1.4 (100 mg, 0.40 mmol) in DMF (10 mL) were added Intermediate 6.3 (257 mg, 0.80 mmol), K$_2$CO$_3$ (167 mg, 1.21 mmol), and a catalytic amount of NaI. The resulting mixture was stirred at 50° C. for 2 h then was diluted with EtOAc (50 mL) and washed with water (50 mL) and brine (50 mL). The organic solution was dried over sodium sulfate and concentrated in vacuo. The crude mixture was purified by silica gel column chromatography (EtOAc/hexanes) to yield the title compound (100 mg, 51%) as a colorless oil. $R_f$ 0.6 (EtOAc/hexanes 1/1); $^1$H NMR (CDCl$_3$) δ 0.07 (s, 3H), 0.09 (s, 3H), 0.88 (s, 9H), 0.80-0.95 (m, 3H), 1.20-1.40 (m, 4H), 1.55-1.70 (m, 2H), 2.90-3.00 (m, 3H), 3.25-3.40 (m, 2H), 3.50-3.60 (m, 2H), 3.89 (s, 3H), 4.25-4.35 (m, 1H), 7.26 (d, J=8.1 Hz, 2H), 7.96 (d, J=8.1 Hz, 2H); MS (m/z) 487.3 (M+1).

Intermediate 6.5: Methyl 4-{2-[2-(4-{[tert-butyl(dimethyl)silyl]oxy}octyl)-5-oxo pyrazolidin-1-yl]ethyl}benzoate.

A mixture of Intermediate 6.4 (100 mg, 0.21 mmol) and 10% palladium on carbon (10 mg) in MeOH (5 mL) was stirred under hydrogen atmosphere (1 atm) for 1 h. The mixture was filtered through celite and concentrated in vacuo to afford the title compound (80 mg, 98%) used in the next step without further purification. $R_f$ 0.5 (EtOAc/hexanes 1/1); $^1$H NMR (CDCl$_3$) δ 0.07 (s, 3H), 0.09 (s, 3H), 0.88 (s, 9H), 0.80-0.95 (m, 3H), 1.20-1.60 (m, 6H), 2.40-2.70 (m, 2H), 2.90-3.00 (m, 2H), 3.05-3.30 (m, 2H), 3.60-3.70 (m, 2H), 3.89 (s, 3H), 7.26 (d, J=8.1 Hz, 2H), 7.96 (d, J=8.1 Hz, 2H); MS (m/z) 491 (M+1).

Intermediate 6.6: Methyl 4-{2-[2-(4-hydroxyoctyl)-5-oxopyrazolidin-1-yl]-ethyl}-benzoate.

Intermediate 6.5 (100 mg, 0.20 mmol) was dissolved in a 4M HCl solution in dioxane (4 mL). The resulting solution was stirred at RT for 1 h then was concentrated in vacuo to afford the title compound (80 mg) used in the next step without further purification. MS (m/z) 487 (M+1).

The title compound, 4-{2-[2-(4-hydroxyoctyl)-5-oxopyrazolidin-1-yl]ethyl}benzoic acid (Example 6), was prepared from Intermediate 6.6 as described in Example 1 above, to provide 4-{2-[2-(4-hydroxyoctyl)-5-oxopyrazolidin-1-yl]ethyl}benzoic acid (28 mg, 30%) as a colorless viscous oil. $^1$H NMR (methanol-$d_4$) δ 0.85-0.95 (m, 3H), 1.20-1.80 (m, 10H), 2.30-3.00 (m, 6H), 3.40-4.00 (m, 3H), 7.35 (d, J=8.4 Hz, 2H), 8.00 (d, J=8.4 Hz, 2H); MS (m/z) 363 (M+1).

Example 7

Synthesis of 4-{2-[2-(4-hydroxy-6-methylheptyl)-5-oxopyrazolidin-1-yl]ethyl}benzoic acid

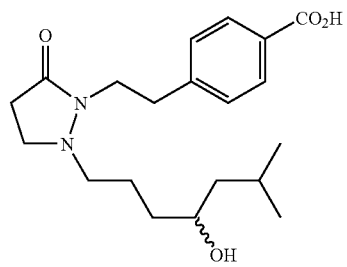

Intermediate 7.1: tert-Butyl-(1-isobutyl-prop-2-ynyloxy)-dimethyl-silane.

To a solution of 5-methyl-hex-1-yn-3-ol (5.0 g, 0.045 mol) in dry DMF (50 mL) were added imidazole (3.64 g, 0.054 mol) and tert-butyldimethylsilyl chloride (6.06 g, 0.054 mol). The resulting mixture was stirred at RT for 2.5 h and then treated with saturated NH$_4$Cl (25 mL) and EtOAc (250 mL). The organic layer was washed with saturated NH$_4$Cl (50 mL), water (4×100 mL), brine (2×100 mL), dried over sodium sulfate, and concentrated in vacuo to afford the crude product (9.84 g, 97.5%), as a yellow oil, which was used in the next step without further purification. $R_f$ 0.9 (EtOAc/hexanes 1/9); $^1$H NMR (CDCl$_3$) δ 0.10 (s, 3H), 0.13 (s, 3H), 0.90-0.88 (m, 15H), 1.53-1.46 (m, 1H), 1.65-1.58 (m, 1H), 1.87-1.77 (septet, J=6.6 Hz, 1H), 2.36-2.35 (t, J=1.84 Hz, 1H), 4.39-4.37 (m, 1H).

Intermediate 7.2: 4-(tert-Butyl-dimethyl-silanyloxy)-6-methyl-hept-2-yn-1-ol.

An oven-dried flask was charged with a solution of intermediate 7.1 (4.08 g, 0.0181 mol, 95%) in THF (180 mL, 0.1 M) under nitrogen atmosphere. The solution was cooled to −70° C., in an acetone-dry ice bath, and then a 1.6 M solution of n-BuLi in hexanes (12 mL, 0.019 mol) was added, dropwise, over 20 minutes. The mixture was stirred for further 15 minutes, when solid paraformaldehyde (1.88 g, 0.0724 mol) was added, in one portion, under nitrogen atmosphere. The stirring was continued for further 10 minutes, and then the cooling bath removed. The resulting solution was allowed to react at RT for 18 h and then treated with saturated NH$_4$Cl (100 mL) and EtOAc (300 mL). The organic layer was washed with saturated NH$_4$Cl (2×100 mL), water (2×100 mL), brine (200 mL), dried over sodium sulfate, and concentrated in vacuo to give a yellow oily residue. The residue was purified by flash column chromatography (EtOAc/hexanes, 1/9) to give fractions of the desired intermediate (2.57 g, 55%) as a colorless oil. $R_f$ 0.24 (EtOAc/hexanes 1/9); $^1$H NMR (CDCl$_3$) δ 0.98 (d, J=1.08 Hz, 3H), 0.12 (d, J=0.72 Hz, 3H), 0.91-0.88 (m, 15H), 1.52-1.44 (m, 1H), 1.63-1.56 (m, 1H), 1.85-1.75 (septet, J=6.95 Hz, 1H), 4.28-4.27 (m, 2H), 4.44-4.40 (m, 1H).

Intermediate 7.3: [(4-bromo-1-isobutylbut-2-ynyl)oxy](tert-butyl)dimethylsilane.

To a solution of intermediate 7.2 (0.60 g, 2.34 mmol) in DCM (15 mL) were added PPh$_3$ (0.74 g, 2.80 mmol) and CBr$_4$ (0.93 g, 2.80 mmol). The resulting solution was stirred at RT for 1 h then concentrated in vacuo and the crude residue was purified by flash column chromatography (EtOAc/hexanes 0.5/9.5) to afford the desired compound (0.50 g, 67%) as a colorless oil. $R_f$ 0.9 (EtOAc/hexanes 1/9); $^1$H NMR (CDCl$_3$) δ 0.10 (s, 3H), 0.12 (s, 3H), 0.80-1.00 (m, 15H), 1.41-1.51 (m, 1H), 1.55-1.65 (m, 1H), 1.75-1.85 (m, 1H), 3.92 (s, 2H), 4.40-4.50 (m, 1H).

Intermediate 7.3: [(4-bromo-1-isobutylbut-2-ynyl)oxy](tert-butyl)dimethylsilane.

To a solution of Intermediate 7.2 (0.60 g, 2.34 mmol) in DCM (15 mL) were added PPh$_3$ (0.74 g, 2.80 mmol) and CBr$_4$ (0.93 g, 2.80 mmol). The resulting solution was stirred at RT for 1 h then concentrated in vacuo and the crude residue was purified by flash column chromatography (EtOAc/hexanes 0.5/9.5) to afford the desired compound (0.50 g, 67%) as a colorless oil. $R_f$ 0.9 (EtOAc/hexanes 1/9); $^1$H NMR (CDCl$_3$) δ 0.10 (s, 3H), 0.12 (s, 3H), 0.80-1.00 (m, 15H), 1.41-1.51 (m, 1H), 1.55-1.65 (m, 1H), 1.75-1.85 (m, 1H), 3.92 (s, 2H), 4.40-4.50 (m, 1H).

Intermediate 7.4: Methyl 4-{2-[2-(4-{[tert-butyl(dimethyl)silyl]oxy}-6-methylhept-2-ynyl)-5-oxopyrazolidin-1-yl]ethyl}benzoate.

To a solution of Intermediate 1.4 (100 mg, 0.40 mmol) in DMF (10 mL) were added Intermediate 7.3 (255 mg, 0.80 mmol), K$_2$CO$_3$ (167 mg, 1.21 mmol), and a catalytic amount of NaI. The resulting mixture was stirred at 50° C. for 2 h then was diluted with EtOAc (50 mL) and washed with water (50 mL) and brine (50 mL). The organic solution was dried over sodium sulfate and concentrated in vacuo. The crude mixture was purified by silica gel column chromatography (EtOAc/hexanes) to yield the title compound (60 mg, 31%) as a colorless oil. $R_f$ 0.5 (EtOAc/hexanes 1/1); $^1$H NMR (CDCl$_3$) δ 0.07 (s, 3H), 0.09 (s, 3H), 0.88 (s, 9H), 0.80-0.95 (m, 15H), 1.30-1.80 (m, 3H), 2.90-3.00 (m, 3H), 3.25-3.40 (m, 2H), 3.50-3.60 (m, 2H), 3.88 (s, 3H), 4.25-4.35 (m, 1H), 7.26 (d, J=8.1 Hz, 2H), 7.96 (d, J=8.1 Hz, 2H); MS (m/z) 487.3 (M+1).

Intermediate 7.5: Methyl 4-{2-[2-(4-{[tert-butyl(dimethyl)silyl]oxy}-6-methylheptyl)-5-oxopyrazolidin-1-yl]ethyl}benzoate.

A mixture of Intermediate 7.4 (50 mg, 0.10 mmol) and 10% Palladium on carbon (10 mg) in MeOH (5 mL) was stirred under hydrogen atmosphere (1 atm) for 1 h. The mixture was filtered through celite and concentrated in vacuo to afford the title compound (48 mg, 98%) used in the next step without further purification. $R_f$ 0.45 (EtOAc/hexanes 1/1), MS (m/z) 491 (M+1).

Intermediate 7.6: Methyl 4-{2-[2-(4-hydroxy-6-methylheptyl)-5-oxopyrazolidin-1-yl]ethyl}benzoate.

Intermediate 7.5 (48 mg, 0.10 mmol) was dissolved in a 4M HCl solution in dioxane (4 mL). The resulting solution was stirred at RT for 1 h then was concentrated in vacuo to afford the title compound (80 mg) used in the next step without further purification. MS (m/z) 377 (M+1).

The title compound, 4-{2-[2-(4-hydroxy-6-methylheptyl)-5-oxopyrazolidin-1-yl]ethyl}benzoic acid (Example 7), was prepared from Intermediate 7.6 as described in Example 1 to provide 4-{2-[2-(4-hydroxy-6-methylheptyl)-5-oxopyrazolidin-1-yl]ethyl}benzoic acid (18 mg, 40%) as a colorless viscous oil. $^1$H NMR (methanol-d$_4$) δ 0.85-0.95 (m, 3H), 1.20-1.80 (m, 10H), 2.30-3.00 (m, 6H), 3.40-4.00 (m, 3H), 7.35 (d, J=8.4 Hz, 2H), 8.00 (d, J=8.4 Hz, 2H); MS (m/z) 363 (M+1).

Example 8

Synthesis of 4-{2-[2-(4-hydroxy-5-methyloctyl)-5-oxopyrazolidin-1-yl]ethyl}benzoic acid

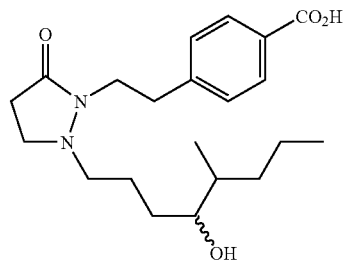

Intermediate 8.1 tert-Butyl-dimethyl-[1-(1-methyl-butyl)-prop-2-ynyloxy]-silane.

To a solution of 4-methyl-hept-1-yn-3-ol (2.53 g, 0.02 mol) in dry DMF (25 mL) were added imidazole (1.63 g, 0.024 mol) and tert-butyldimethylsilyl chloride (3.62 g, 0.024 mol). The resulting solution was stirred at RT for 18 h and then treated with saturated NH$_4$Cl (15 mL) and EtOAc (120 mL). The organic layer was washed with saturated NH$_4$Cl (20 mL), water (4×20 mL), brine (2×20 mL), dried over sodium sulfate, and concentrated in vacuo to afford a crude product (4.65 g, 97%), as a yellow oil, which was used in the next step without further purification. R$_f$ 0.9 (EtOAc/hexanes 1/9); $^1$H NMR (CDCl$_3$) δ 0.08 (s, 3H), 0.12 (s, 3H), 0.96-0.85 (m, 15H), 1.57-1.10 (m, 4H), 1.69-1.61 (m, 1H), 2.33 (t, J=2.20 Hz, 1H), 4.22-4.18 (m, 1H).

Intermediate 8.2: 4-(tert-Butyl-dimethyl-silanyloxy)-5-methyl-oct-2-yn-1-ol.

An oven-dried flask was charged with a solution of intermediate 8.1 (4.09 g, 0.017 mol, 95%) in THF (170 mL, 0.1 M) under nitrogen atmosphere. The solution was cooled to –70° C., in an acetone-dry ice bath, and then a 1.6 M solution of n-BuLi in hexanes (13 mL, 0.020 mol) was added, dropwise, over 15 minutes. The mixture was stirred for further 20 minutes, when solid paraformaldehyde (2.11 g, 0.070 mol) was added, in one portion, under nitrogen atmosphere. The stirring was continued for further 10 minutes, and then the cooling bath removed. The resulting solution was allowed to react at RT for 18 hr and then treated with saturated NH$_4$Cl (100 mL) and EtOAc (300 mL). The organic layer was washed with saturated NH$_4$Cl (2×100 mL), water (2×100 mL), brine (200 mL), dried over sodium sulfate, filtered, and concentrated in vacuo to give a yellow oily residue (4.52 g). The residue was purified by flash column chromatography (EtOAc/hexanes, 1/9) to give fractions of the desired intermediate (3.48 g, 76%) as a yellow oil. R$_f$ 0.24 (EtOAc/hexanes 1/9); $^1$H NMR (CDCl$_3$) δ 0.07 (s, 3H), 0.11 (s, 3H), 0.94-0.85 (m, 15H), 1.56-1.08 (m, 4H), 1.69-1.59 (m, 1H), 4.25-4.23 (m, 1H), 4.28 (s, 2H).

Intermediate 8.3: {[4-bromo-1-(1-methylbutyl)but-2-ynyl]oxy}(tert-butyl)dimethylsilane.

To a solution of Intermediate 8.2 (0.63 g, 2.34 mmol) in DCM (15 mL) were added PPh$_3$ (0.74 g, 2.80 mmol) and CBr$_4$ (0.93 g, 2.80 mmol). The resulting solution was stirred at RT for 1 h then concentrated in vacuo and the crude residue was purified by flash column chromatography (EtOAc/hexanes 0.5/9.5) to afford the desired compound (0.54 g, 70%) as a colorless oil. R$_f$ 0.9 (EtOAc/hexanes 1/9); $^1$H NMR (CDCl$_3$) δ 0.08 (s, 3H), 0.12 (s, 3H), 0.80-1.00 (m, 15H), 1.10-1.70 (m, 5H), 3.93 (s, 2H), 4.20-4.30 (m, 1H).

Intermediate 8.4: Methyl 4-{2-[2-(4-{[tert-butyl(dimethyl)silyl]oxy}-5-methyloct-2-ynyl)-5-oxopyrazolidin-1-yl]ethyl}benzoate.

To a solution of Intermediate 1.4 (100 mg, 0.40 mmol) in DMF (10 mL) were added Intermediate 8.3 (266 mg, 0.80 mmol), K$_2$CO$_3$ (110.6 mg, 0.80 mmol), and a catalytic amount of NaI. The resulting mixture was stirred at RT for 48 h then was diluted with EtOAc (50 mL) and washed with water (50 mL) and brine (50 mL). The organic solution was dried over sodium sulfate and concentrated in vacuo. The crude mixture was purified by silica gel column chromatography (EtOAc/hexanes) to yield the title compound (110 mg, 55%) as a colorless oil. R$_f$ 0.7 (EtOAc/hexane 1/1); H NMR (CDCl$_3$) δ 0.07 (s, 3H), 0.09 (s, 3H), 0.80-0.95 (m, 15H), 1.00-1.70 (m, 5H), 2.90-3.00 (m, 2H), 3.25-3.40 (m, 2H), 3.55-3.70 (m, 2H), 3.89 (s, 3H), 4.25-4.35 (m, 1H), 7.26 (d, J=8.1 Hz, 2H), 7.96 (d, J=8.1 Hz, 2H); MS (m/z) 501 (M+1).

Intermediate 8.5: Methyl 4-{2-[2-(4-{[tert-butyl(dimethyl)silyl]oxy}-5-methyloctyl)-5-oxopyrazolidin-1-yl]ethyl}benzoate.

A mixture of Intermediate 8.4 (100 mg, 0.10 mmol) and 10% Palladium on carbon (10 mg) in MeOH (5 mL) was stirred under hydrogen atmosphere (1 atm) for 1 h. The mixture was filtered through celite and concentrated in vacuo to afford the title compound (100 mg, 98%) used in the next step without further purification. R$_f$ 0.65 (EtOAc/hexane 1/1), MS (m/z) 503 (M+1).

Intermediate 8.6: Methyl 4-{2-[2-[(4-hydroxy-5-methyloctyl)-5-oxopyrazolidin-1-yl]ethyl}benzoate.

Intermediate 8.5 (100 mg, 0.20 mmol) was dissolved in a 4M HCl solution in dioxane (4 mL). The resulting solution was stirred at RT for 1 h then was concentrated in vacuo to afford the title compound (70 mg, 91%) used in the next step without further purification. MS (m/z) 389.3 (M+1).

The title compound, 4-{2-[2-(4-hydroxy-5-methyloctyl)-5-oxopyrazolidin-1-yl]ethyl}benzoic acid (Example 8), was prepared from Intermediate 8.6 as described in Example 1 above, to provide 4-{2-[2-(4-hydroxy-5-methyloctyl)-5-oxopyrazolidin-1-yl]ethyl}benzoic acid (18 mg, 20%) as a colorless viscous oil. $^1$H NMR (methanol-d$_4$) δ 0.80-1.80 (m, 11H), 2.30-3.00 (m, 6H), 3.40-4.00 (m, 3H), 7.35 (d, J=8.4 Hz, 2H), 8.00 (d, J=8.4 Hz, 2H); MS (m/z) 375 (M+1).

Example 9

Synthesis of 4-{2-[2-(4-ethyl-4-hydroxyoctyl)-5-oxopyrazolidin-1-yl]ethyl}benzoic acid

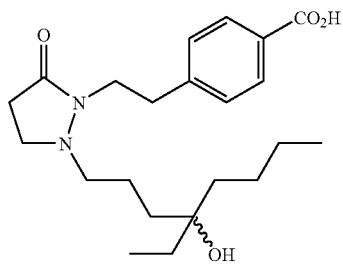

Intermediate 9.1: tert-Butyl-(1-butyl-1-ethyl-prop-2-ynyloxy)-dimethylsilane.

An oven-dried flask was charged with 3-ethyl-hept-1-yn-3-ol (1.0 g, 0.007 mol) and dry DMF (7.0 mL). To this solution, cooled in an ice bath, was added Et$_3$N (4.0 mL, 0.029 mol) followed by dropwise addition of tert-butyldimethylsilyltrifluoro methanesulfonate (2.5 g, 0.014 mol) under nitrogen atmosphere. The resulting mixture was stirred at RT for 18 h and then diluted with EtOAc (80 mL). The organic layer was washed with a saturated solution of NH$_4$Cl (30 mL), water (4×20 mL), brine (40 mL), dried over sodium sulfate, filtered, and evaporated to afford the desired compound (1.80 g, 98%), as a yellow oil, used in the next step without further purification. R$_f$ 0.9 (EtOAc/hexanes 1/9); $^1$H NMR (CDCl$_3$) δ 0.15 (s, 6H), 0.96-0.84 (m, 15H), 1.65-1.29 (m, 8H), 2.39 (s, 1H).

Intermediate 9.2: 4-(tert-Butyl-dimethyl-silanyloxy)-4-ethyl-oct-2-yn-1-ol.

An oven-dried flask was charged with a solution of intermediate 9.1 (1.80 g, 0.007 mol) in THF (72.0 mL, 0.1 M) under nitrogen atmosphere. The solution was cooled to −70° C., in an acetone-dry ice bath, and then a 1.6 M solution of n-BuLi in hexanes (5.4 mL, 0.0086 mol) was added, dropwise, over 10 minutes. The mixture was stirred for further 0.5 h, when solid paraformaldehyde (0.87 g, 0.004 mol) was added, in one portion, under nitrogen atmosphere. The stirring was continued for further 10 minutes, and then the cooling bath removed. The resulting solution was allowed to react at RT for 18 hr and then treated with saturated NH$_4$Cl (100 mL) and EtOAc (300 mL). The organic layer was washed with saturated NH$_4$Cl (2×100 mL), water (2×100 mL), brine (200 mL), dried over sodium sulfate, and concentrated in vacuo to give a yellow oily residue. The residue was purified by flash column chromatography (EtOAc/hexanes 1/9) to give the desired intermediate (4.02 g, 86%) as a colorless oil. R$_f$ 0.16 (EtOAc/hexanes 1/9); $^1$H NMR (CDCl$_3$) δ 0.14 (s, 6H), 0.94-0.85 (m, 15H), 1.45-1.27 (m, 4H), 1.64-1.55 (m, 4H), 4.29 (d, J=6.22 Hz, 2H).

Intermediate 9.3: (4-Bromo-1-butyl-1-ethyl-but-2-ynyloxy)-tert-butyl-dimethyl-silane.

To a solution of intermediate 9.2 (0.50 g, 1.76 mmol) in DCM (6.0 mL) were added PPh$_3$ (0.86 g, 3.17 mmol) and CBr$_4$ (1.1 g, 3.17 mmol). The resulting solution was stirred at RT for 1 h and then concentrated in vacuo. The crude product was purified by flash column chromatography (hexanes) to afford fractions of the desired compound (0.83 g, 80%) as a colorless oil. R$_f$ 0.83, (EtOAc/hexanes 1/9). $^1$H NMR (CDCl$_3$) δ 0.15 (s, 6H), 0.94-0.85 (m, 15H), 1.45-1.27 (m, 4H), 1.64-1.55 (m, 4H), 3.94 (s, 2H).

Intermediate 9.4: 4-(2-{[4-(tert-Butyl-dimethyl-silanyloxy)-4-ethyl-oct-2-ynyl]-5-oxo-pyrazolidin-1-yl}-ethyl)-benzoic acid methyl ester.

To a solution of intermediate 1.4 (113.1 mg, 0.446 mol) in DMF (4.5 mL) were added intermediate 9.3 (310.7 mg, 0.898 mmol), K$_2$CO$_3$ (386 mg, 2.80 mmol) and catalytic amount of NaI. The resulting mixture was stirred at RT for 18 h and then diluted with EtOAc (25 mL). The organic layer was washed with a saturated solution of NH$_4$Cl (2×10 mL), water (4×10 mL), brine (2×10 mL), dried over sodium sulfate, and evaporated in vacuo to give a crude product which was purified on flash column chromatography (EtOAc/hexanes 3/7) to afford the desired compound (142.6 mg, 62%) as a yellow oil. $^1$H NMR (CDCl$_3$) δ 0.10 (s, 6H), 0.91-0.80 (m, 15H), 1.33-1.23 (m, 4H), 1.61-1.53 (m, 4H), 2.94 (t, J=7.32 Hz, 2H), 3.30 (s, 2H), 3.57 (s, 2H), 3.86 (s, 3H), 7.26 (d, J=8.06 Hz, 2H), 7.93 (d, J=7.69 Hz, 2H); MS (m/z) 515 (M+1).

Intermediate 9.5: 4-(2-{-[4-(tert-Butyl-dimethyl-silanyloxy)-4-ethyl-octyl]-5-oxo-pyrazolidin-1-yl}-ethyl)-benzoic acid methyl ester.

A heterogeneous mixture of intermediate 9.4 (142.6 mg, 0.277 mmol) and 10% Palladium on carbon (10 mg) in MeOH (10 mL) was stirred under hydrogen atmosphere (1 atm) for 1 h. The mixture was filtered through celite and concentrated in vacuo to afford the title compound (139.0 mg, 97%), as a colorless oil, which was used in the next step without further-purification. $^1$H NMR (CDCl$_3$) δ 0.061 (s, 6H), 0.91-0.81 (m, 15H), 1.31-1.23 (m, 4H), 1.54-1.36 (m, 4H), 2.67 (s, 2H), 2.98 (t, J=6.96 Hz, 2H), 7.29 (d, J=8.06 Hz, 2H), 7.95 (d, J=8.06 Hz, 2H); MS (m/z) 519 (M+1).

Intermediate 9.6: 4-{2-[2-(4-Ethyl-4-hydroxy-octyl)-5-oxo-pyrazolidin-1-yl]-ethyl}-benzoic acid methyl ester.

Intermediate 9.5 (139.0 mg, 0.268 mmol) was dissolved in a 4M HCl solution in dioxane (10 mL). The resulting solution was stirred at RT for 1 h and then concentrated in vacuo to afford the title compound (108 mg, 99.6%) used in the next step without further purification.

The title compound, 4-{2-[2-(4-ethyl-4-hydroxy-octyl)-5-oxo-pyrazolidin-1-yl]-ethyl}benzoic acid (Example 9), was prepared from Intermediate 9.6 according to the procedure described for Example 1 above to provide 4-{2-[2-(4-ethyl-4-hydroxy-octyl)-5-oxo-pyrazolidin-1-yl]-ethyl}benzoic acid (10.6 mg, 41.7%) as a colorless viscous oil. $^1$H NMR (CD$_3$OD) δ 0.94-0.83 (m, 6H), 1.48 (s, 2H), 2.98-2.95 (m, 2H), 3.21 (s, 2H), 3.30-3.28 (m, 2H), 7.35-7.32 (m, 2H), 7.94-7.90 (m, 2H); MS (m/z) 391 (M+1).

Example 10

Synthesis of 4-{2-[2-(4-hydroxy-4-methylheptyl)-5-oxopyrazolidin-1-yl]ethyl}benzoic acid

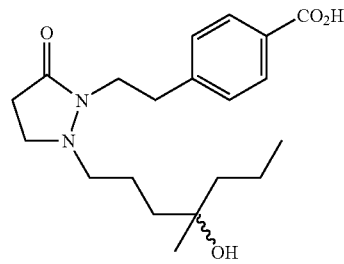

Intermediate 10.1: tert-Butyl-dimethyl-(1-methyl-1-propyl-prop-2-ynyloxy)-silane. An oven dried flask was charged with 3-methyl-hex-1-yn-3-ol (1.02 g, 0.009 mol) and dry DMF (9.0 mL). To this solution, cooled in an ice bath, was added Et$_3$N (4.6 mL, 0.033 mol) followed by dropwise addition of tert-butyldimethylsilyl trifluoromethanesulfonate (2.9 g, 0.016 mol) under nitrogen atmosphere. The resulting mixture was stirred at RT for 18 h and then diluted with EtOAc (50 mL). The organic layer was washed with a saturated solution of NH$_4$Cl (30 mL), water (4×20 mL), brine (40 mL), dried over sodium sulfate, and evaporated to afford the desired compound (2.05 g, 99.6%), as a yellow oil, used in the next step without further purification. R$_f$ 0.9 (EtOAc/hexanes 1/9); $^1$H NMR (CDCl$_3$) δ 0.152 (s, 3H), 0.156 (s, 3H), 0.85-0.84 (m, 9H), 0.91 (t, J=6.69 Hz, 3H), 1.41 (s, 3H), 1.61-1.44 (m, 4H), 3.37 (s, 1H).

Intermediate 10.2: 4-(tert-Butyl-dimethyl-silanoxy)-4-methyl-hept-2-yn-1-ol.

An oven-dried flask was charged with a solution of intermediate 10.1 (2.05 g, 0.009 mol) in THF (91.0 mL, 0.1 M) under nitrogen atmosphere. The solution was cooled to −70° C., in an acetone-dry ice bath, and then a 1.6 M solution of n-BuLi in hexanes (8.0 mL, 0.013 mol) was added, dropwise, over 15 minutes. The mixture was stirred for further 0.5 h, when solid paraformaldehyde (1.4 g, 0.004 mol) was added, in one portion, under nitrogen atmosphere. The stirring was continued for further 15 minutes, and then the cooling bath removed. The resulting solution was allowed to react at room temperature for 18 hr and then treated with saturated NH$_4$Cl (100 mL) and EtOAc (300 mL). The organic layer was washed with saturated NH$_4$Cl (2×100 mL), water (2×100 mL), brine (200 mL), dried over sodium sulfate, filtered, and concentrated in vacuo to give a yellow oily residue. The residue was purified by flash column chromatography (EtOAc/hexanes, 1/9) to give fractions of the desired intermediate (1.61 g, 69%) as a colorless oil. R$_f$ 0.16 (EtOAc/hexanes 1/9); $^1$H NMR (CDCl$_3$) δ 0.14 (s, 6H), 0.85 (s, 9H), 0.90 (t, J=7.32 Hz, 3H), 1.40 (s, 3H), 1.59-1.41 (m, 4H), 4.28 (d, J=6.22 Hz, 2H).

Intermediate 10.3: (4-bromo-1-methyl-1-propyl-but-2-ynyloxy)-tert-butyl-dimethyl-silane.

To a solution of intermediate 10.2 (0.48 g, 1.88 mmol) in DCM (8.0 mL) were added PPh$_3$ (0.89 g, 3.4 mmol) and CBr$_4$ (0.63 g, 3.4 mmol). The resulting solution was stirred at RT for 1 h and then concentrated in vacuo. The crude product was purified by flash column chromatography (hexanes) to afford fractions of the desired compound (0.58 g, 96%) as a colorless oil. R$_f$ 0.75, (EtOAc/hexanes 1/9). $^1$H NMR (CDCl$_3$) δ 0.15 (s, 6H), 0.85 (s, 9H), 0.91 (t, J=7.32 Hz, 3H), 1.39 (s, 3H), 1.63-1.42 (m, 4H), 3.93 (s, 3H).

Intermediate 10.4: 4-(2-{2-[4-(tert-Butyl-dimethyl-silanyloxy)-4-methyl-hept-2-ynyl]-5-oxo-pyrazolidin-1-yl}-ethyl)-benzoic acid methyl ester.

To a solution of intermediate 1.4 (80.1 mg, 0.323 mmol) in DMF (3.0 mL) were added intermediate 10.3 (380 mg, 1.20 mmol), K$_2$CO$_3$ (267.4 mg, 1.93 mmol) and catalytic amount of NaI. The resulting mixture was stirred at RT for 18 h and then diluted with EtOAc (30 mL). The organic layer was washed with a saturated solution of NH$_4$Cl (2×5 mL), water (4×10 mL), brine (2×10 mL), dried over sodium sulfate, and evaporated in vacuo to give a crude residue. Purification by flash column chromatography (EtOAc/hexanes 3/7) gave the desired compound (143.4 mg, 29.5%) as a colorless oil. $^1$H NMR (CDCl$_3$) δ 0.11 (s, 6H), 0.84 (s, 9H), 0.90 (t, J=7.32, 3H), 1.38 (s, 3H), 1.58-1.38 (m, 4H), 2.96 (t, J=7.32 Hz, 2H), 3.32 (s, 2H), 3.57 (s, 2H), 3.89 (s, 3H), 7.29 (d, J=8.06, 2H), 7.95 (d, J=8.06 Hz, 2H); MS (m/z) 487 (M+1).

Intermediate 10.5: 4-(2-{2-[4-(tert-Butyl-dimethyl-silanyloxy)-4-methyl-heptyl]-5-oxo-pyrazolidin-1-yl}-ethyl)-benzoic acid methyl ester.

A heterogeneous mixture of intermediate 10.4 (203.6 mg, 0.407 mmol) and 10% Palladium on carbon (10 mg) in MeOH (10 mL) was stirred under hydrogen atmosphere (1 atm) for 1 h. The mixture was filtered through celite and concentrated in vacuo to afford the title compound (151.3 mg, 74%), as a colorless oil, which was used in the next step without further purification. $^1$H NMR (CDCl$_3$) δ 0.06 (s, 6H), 0.85 (s, 9H), 0.88 (t, J=7.32 Hz, 3H), 1.16 (s, 3H), 1.52-1.24 (m, 8H), 2.66 (t, J=6.96 Hz, 2H), 2.98 (t, J=7.32 Hz, 2H), 3.18 (s, 2H), 3.88 (s, 3H), 7.29 (d, J=8.06 Hz, 2H), 7.95 (d, J=8.06 Hz, 2H); MS (m/z) 491 (M+1).

Intermediate 10.6: 4-{2-[2-(4-Hydroxy-4-methyl-heptyl)-5-oxo-pyrazolidin-1-yl]-ethyl}-benzoic acid methyl ester.

Intermediate 10.5 (91.0 mg, 0.186 mmol) was dissolved in a 4M HCl solution in dioxane (10 mL). The resulting solution was stirred at RT for 1.5 h and then concentrated in vacuo to afford 4-{2-[2-(4-Hydroxy-4-methyl-heptyl)-5-oxo-pyrazolidin-1-yl]-ethyl}-benzoic acid methyl ester (86.2 mg, 99.6%) used in the next step without further purification.

The title compound, 4-{2-[2-(4-Hydroxy-4-methyl-heptyl)-5-oxo-pyrazolidin-1-yl]-ethyl}-benzoic acid (Example 10), was prepared from Intermediate 10.6 as described in Example 1 above, to provide 4-{2-[2-(4-Hydroxy-4-methyl-heptyl)-5-oxo-pyrazolidin-1-yl]-ethyl}-benzoic acid (11.9 mg, 18.0%) as a colorless viscous oil. $^1$H NMR (CD$_3$OD) δ 0.93 (t, J=6.96 Hz, 3H), 1.14 (s, 3H), 1.54-1.34 (m, 8H), 3.0-2.96 (m, 2H), 2.76 (br t, 2H), 3.23 (br t, 2H), 3.30-3.28 (m, 3H), 7.34 (d, J=8.06 Hz, 2H), 7.92 (d, J=8.06 Hz, 2H); MS (m/z) 363 (M+1).

Example 11

Synthesis of 4-{2-[2-(4-hydroxy-4,7-dimethyloctyl)-5-oxopyrazolidin-1-yl]ethyl}benzoic acid

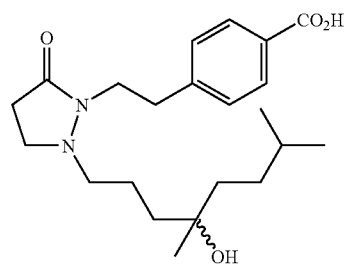

Intermediate 11.1: tert-Butyl-(1-isobutyl-1-methyl-prop-2-ynyloxy)-dimethylsilane.

An oven-dried flask was charged with 3,6-dimethyl-1-heptyn-3-ol (1.0 g, 0.007 mol) and dry DMF (7.0 mL). To this solution, cooled in an ice bath, was added Et$_3$N (3.6 mL, 0.025 mol) followed by dropwise addition of tert-butyldimethylsilyl trifluoromethanesulfonate (2.5 g, 0.014 mol) under nitrogen atmosphere. The resulting mixture was stirred at RT for 18 h and then diluted with EtOAc (80 mL). The organic layer was washed with saturated solution of NH$_4$Cl (30 mL), water (4×20 mL), brine (40 mL), dried over sodium sulfate, and evaporated to afford the desired compound (1.8 g), as a yellow oil, used in the next step without further purification. R$_f$ 0.9 (EtOAc/hexanes 1/9); $^1$H NMR (CDCl$_3$) δ 0.15 (s, 6H), 0.88-0.84 (m, 15H), 1.38-1.29 (m, 1H), 1.42 (s, 3H), 1.54-1.48 (m, 2H), 1.62-1.55 (m, 2H), 2.38 (s, 1H).

Intermediate 11.2: 4-(tert-Butyl-dimethylsilanoxy)-4,6-dimethyl-hept-2-yn-1-ol.

To a solution of intermediate 11.1 (1.83 g, 0.007) in dry THF (72 mL) cooled at −70° C., in a dry ice-acetone bath, was added dropwise a 1.6 M solution of n-BuLi in hexanes (6.0 mL, 0.01 mol) over 12 minutes. The resulting solution was stirred at −70° C. for further 0.5 h and then solid paraformaldehyde (0.86 g, 0.029 mol) was added, in one portion, under nitrogen atmosphere. After 10 minutes, the cooling bath was removed and the mixture stirred at RT overnight, and then diluted with EtOAc (100 mL). The organic layer was washed with a saturated solution of NH$_4$Cl (100 mL), water (100 mL), brine (100 mL), dried over saturated sodium sulfate, filtered, evaporated in vacuo to give a crude product. Purification on flash column chromatography (EtOAc/hexanes 1/9) afforded the desired compound (0.93 g, 45.5%) as a colorless oil. R$_f$ 0.15 (EtOAc/hexanes 1/9); $^1$H NMR (CDCl$_3$) δ 0.15 (s, 6H), 0.85 (s, 9H), 0.87 (d, J=6.59 Hz, 6H), 1.36-1.27 (m, 1H), 1.39 (s, 3H), 1.60-1.46 (m, 4H).

Intermediate 11.3: [4-Bromo-1-isopentyl-1-methylbut-2-ynyl]oxy](tert-butyl)dimethyl silane.

To a solution of Intermediate 11.2 (365 mg, 1.29 mmol) in 10 mL of DCM was added PPh$_3$ (407 mg, 1.55 mmol) and CBr$_4$(513 mg, 1.55 mmol). The resulting solution was stirred at RT for 1 h then concentrated in vacuo. The crude residue was purified by flash column chromatography (EtOAc/hexanes 0.5/9.5) over silica gel to afford the desired compound (437 mg, 98%) as colorless oil. $^1$HNMR (CDCl$_3$) δ 0.16 (s, 6H), 0.85 (s, 9H), 0.87 (s, 3H), 0.89 (s, 3H), 1.25-1.35 (m, 1H), 1.39 (s, 3H), 1.45-1.65 (m, 4H), 3.93 (s, 2H).

Intermediate 11.4: Methyl 4-{2-[2-(4-{[tert-butyl(dimethyl)siyl]oxy}-4,7-dimethyloct-2-ynyl)-5-oxopyrazolidin-1-yl]ethyl}benzoate.

To a solution of intermediate 1.4 (117 mg, 0.47 mmol) in DMF (8 mL) was added intermediate 11.3 (325 mg, 0.938 mmol), K$_2$CO$_3$ (195 mg, 1.41 mmol), and a catalytic amount of NaI. The resulting mixture was stirred at 50° C. for 2 h then was diluted with EtOAc (50 mL) and washed with water (50 mL) and brine (50 mL). The organic solution was dried over Na$_2$SO$_4$ and concentrated in vacuo. The crude mixture was purified by silica gel column chromatography (EtOAc/hexanes) to yield methyl 4-{2-[2-(4-{[tert-butyl(dimethyl)siyl]oxy}-4,7-dimethyloct-2-ynyl)-5-oxopyrazolidin-1-yl]ethyl}benzoate (110 mg, 45%) as a colorless oil. $^1$H NMR (CDCl$_3$) δ 0.12 (s, 6H), 0.84 (s, 9H), 0.86 (s, 3H), 0.87 (s, 3H), 1.25-1.35 (m, 1H), 1.39 (s, 3H), 1.45-1.60 (m, 4H), 2.94-2.95 (m, 4H), 3.25-3.35 (br m, 2H), 3.55-3.65 (br m, 2H), 3.89 (s, 5H), 7.26 (d, J=7.9 Hz, 2H), 7.94 (d, J=7.9 Hz, 2H); MS (m/z) 514.7 (M+1).

Intermediate 11.5: Methyl 4-{2-[2-(4-{[tert-butyl(dimethyl)silyl]oxy}-4,7-dimethyloctyl)-5-oxopyrazolidin-1-yl]ethyl}benzoate.

A mixture of intermediate 11.4 (110 mg, 0.214 mmol) and 10% Palladium on carbon (11.4 mg, 5 mol %) in MeOH (10 mL) was stirred under hydrogen atmosphere (1 atm) for 2 h. The mixture was filtered through celite and concentrated in vacuo to afford methyl 4-{2-[2-(4-{[tert-butyl(dimethyl)silyl]oxy}-4,7-dimethyloctyl)-5-oxopyrazolidin-1-yl]ethyl}benzoate, which was used in the next step without purification. MS (m/z) 519.1 (M+1).

Intermediate 11.6: Methyl 4-{2-[2-(4-hydroxy-4,7-dimethyloctyl)-5-oxopyrazolidin-1-yl]ethyl}benzoate.

Intermediate 11.5 was dissolved in a 4 M HCl solution in dioxane (5 mL). The resulting solution was stirred at RT for 2 h then was concentrated in vacuo to afford the free alcohol. The crude compound was used directly for next step without further purification. MS (m/z) 405.3 (M+1).

The title compound, 4-{2-[2-(4-hydroxy-4,7-dimethyloctyl)-5-oxopyrazolidin-1-yl]ethyl}benzoic acid (Example 11), was prepared from Intermediate 11.6 according to procedure described in Example 1 above to provide 4-{2-[2-(4-hydroxy-4,7-dimethyloctyl)-5-oxopyrazolidin-1-yl]ethyl}benzoic acid (14.9 mg, 14%) as a colorless oil. $^1$H NMR (methanol-d$_4$) δ 0.80-1.00 (m, 7H), 1.10-1.30 (m, 6H), 1.35-1.60 (m, 7H), 2.70-2.85 (m, 2H), 2.90-3.05 (m, 2H), 3.15-3.35 (m, 4H), 7.45 (d, J=8.5 Hz, 2H), 7.93 (d, J=8.5 Hz, 2H); MS (m/z) 391.2 (M+1).

Example 12

Synthesis of 4-{2-[2-(3-hydroxy-5-methylhexyl)-5-oxopyrazolidin-1-yl]ethyl}benzoic acid

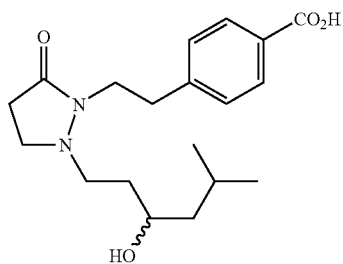

Intermediate 12.1: 5-methylhex-1-en-3-ol

To a solution of 5-methyl-1-hexyl-3-ol (670 mg, 5.97 mmol) in DCM (15 ml) was added Pd/CaCO$_3$ (130 mg). The mixture was hydrogenated (1 atm) at RT for 6 h. After the catalyst was removed through Celite filtration, the solvent was removed under vacuum to give 500 mg of the title compound as colorless on used in the next step without purification. $^1$H NMR (CDCl$_3$) δ: 0.92 (d, 6H), 1.30-1.32 (m), 1.41-1.44 (m), 1.71-1.74 (m), 4.15 (m, 1H), 5.08 (d, J=10.6 Hz, 1H), 5.20 (d, J=17.2 Hz, 1H), 5.80 (m, 1H).

Intermediate 12.2: 5-methylhex-1-en-3-one

To a solution of Intermediate 12.1 (500 mg, 4.4 mmol) in DCM (10 ml) was added Dess-Martin periodinane reagent (2.05 g, 4.84 mmol) and the solution was stirred at RT for 20 minutes. Ether (20 mL) was added to the mixture, and later 15 ml of 1.3 M NaOH solution was added. The mixture was stirred for an additional 10 minutes. After all the precipitate was dissolved into aqueous layer, the solution was extracted with ether (3×50 mL). The combined organic layer was washed with 1.3 M NaOH solution (100 mL), brine (100 mL), dried and concentrated to give 500 mg of the title compound as colorless oil used in the next step without purification.

Intermediate 12.3: methyl 4-{2-[2-(5-methyl-3-oxohexyl)-5-oxopyrazolidin-1-yl]ethyl}benzoate.

To a solution of Intermediate 12.2 (134 mg, 1.2 mmol) in isopropanol (10 ml) was added intermediate 1.4 (75 mg, 0.30 mmol) and Et$_3$N (94 mL, 1 0.30 mmol). The reaction was refluxed for 2 h and was then concentrated under reduced pressure. The residue was dissolved into EtOAc (50 mL) and washed with 1N HCl (50 mL), 5% NaHCO$_3$ (50 mL), and brine (50 mL), dried over anhydrous Na$_2$SO$_4$ and evaporated under reduced pressure. The crude product was purified by flash column chromatography (silica gel; to give the title compound as colorless oil (100 mg, 92%). R$_f$=0.2 (EtOAc); MS (ES) m/e 361.2 (MH$^+$); $^1$H NMR (CDCl$_3$) δ 0.91 (d, J=6.59 Hz, 6H), 2.14 (m, 1H), 2.30 (d, J=6.96 Hz, 2H), 2.51 (m, 2H), 2.93 (t, J=7.32 Hz, 2H), 2.90-3.09 (m, 4H), 3.87 (s, 3H), 7.26 (d, J=7.69 Hz, 2H), 7.94 (d, J=7.32 Hz, 2H).

Intermediate 12.4: methyl 4-{2-[2-(3-hydroxy-5-methylhexyl)-5-oxopyrazolidin-1-yl]ethyl}benzoate To a solution of 12.3 (160 mg, 0.44 mmol) in MeOH (2 ml) at −15° C. was added CeCl$_3$.6H$_2$O (165 mg, 0.44 mmol) in water (1 ml). Then NaBH$_4$ (35 mg, 0.67 mmol) was added in one portion. The reaction mixture was stirred for 15 minutes and was evaporated, dissolved in EtOAc, washed with brine (50 mL), dried (NaSO$_4$) and concentrated in vacuo to afford the title compound (150 mg) as colorless oil used in the next step without purification. MS (m/z) 363.2 (M+1)

The title compound, 4-{2-[2-(3-hydroxy-5-methylhexyl)-5-oxopyrazolidin-1-yl]ethyl}benzoic acid (Example 12), was prepared from Intermediate 12.4 as described in Example 1 above, to provide 4-{2-[2-(3-hydroxy-5-methylhexyl)-5-oxopyrazolidin-1-yl]ethyl}benzoic acid (59 mg, 50%) as a colorless viscous oil. $^1$H NMR (methanol-$d_4$) δ 0.9 (d, 6H), 1.24 (m, 1H), 1.40 (m, 1H), 1.52 (m, 1H), 1.61 (m, 1H), 1.79 (m, 1H), 2.90 (m, 2H), 3.0 (m, 2H), 3.2 (m, 2H) 3.75 (m, 1H), 7.34 (d, J=7.69 Hz, 2H), 7.90 (d, J=7.32 Hz, 2H); MS (m/z) 349.2 (M+1).

Example 13

Synthesis of 4-{2-[2-(3-hydroxy-4-methylheptyl)-5-oxopyrazolidin-1-yl]ethyl}benzoic acid

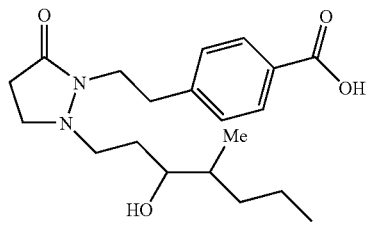

Intermediate 13.1: 4-methylhept-1-en-3-ol.

To a solution of 4-methyl-1-heptyl-3-ol (695 mg, 5.5 mmol) in DCM (5 ml) was added Pd/CaCO$_3$ (139 mg). The mixture was hydrogenated (1 atm) at RT for 4 h. After the catalyst was removed by filtration through Celite, the solvent was removed under vacuum to give the intermediate 13.1 (500 mg) as colorless oil used in the next step without purification. $^1$H NMR (CDCl$_3$) δ: 0.92 (d, 6H), 1.30-1.32 (m), 1.41-1.44 (m), 1.71-1.74 (m), 4.15 (m, 1H), 5.08 (d, J=10.8 Hz, 1H), 5.20 (d, J=16.1 Hz, 1H), 5.80 (m, 1H).

Intermediate 13.2: 4-methylhept-1-en-3-one

To a solution of Intermediate 13.1 (700 mg, 5.5 mmol) in DCM (10 ml) was added Dess-Martin periodinane reagent (2.57 g, 6.6 mmol) and the solution was stirred at room temperature for 20 minutes. Ether (20 mL) was added to the mixture, and later 15 ml of 1.3 M NaOH solution was added. The mixture was stirred for an additional 10 minutes. After all the precipitate was dissolved into aqueous layer, the solution was extracted with ether (3×50 mL). The combined organic layer was washed with 1.3 M NaOH solution, brine, dried, and concentrated to afford the title compound (500 mg) as colorless oil used in the next step without purification.

Intermediate 13.3: methyl 4-{2-[2-(4-methyl-3-oxoheptyl)-5-oxopyrazolidin-1-yl]ethyl}benzoate.

To a solution of Intermediate 13.2 (151 mg, 1.2 mmol) in isopropanol (10 ml) were added intermediate 1.4 (75 mg, 0.30 mmol) and Et$_3$N (94 μL, 0.03 mmol). The reaction was refluxed for 2 h then concentrated under reduced pressure. The crude residue was dissolved in EtOAc (50 mL) and washed with 1N HCl solution (50 mL), 5% NaHCO$_3$ (50 mL), and brine (50 mL), dried over anhydrous Na$_2$SO$_4$ and evaporated under reduced pressure. The crude product was purified by flash column chromatography (EtOAc) to give the title compound as colorless oil (98 mg, 87%). R$_f$ 0.2 (EtOAc); MS (ES) m/e 375.2 (M+H$^+$).

Intermediate 13.4: methyl 4-{2-[2-(4-methyl-3-oxoheptyl)-5-oxopyrazolidin-1-yl]ethyl}benzoate To a solution of Intermediate 13.3 (96 mg, 0.257 mmol) in MeOH (2 ml) at −15° C. was added a solution of CeCl$_3$.6H$_2$O (96 mg, 0.257 mmol) in water (1 ml). Then NaBH$_4$ (15 mg, 0.386 mmol) was added in one portion. The reaction mixture was stirred for 15 minutes and then was evaporated, dissolved in EtOAc (40 mL), washed with brine (50 mL), dried (NaSO$_4$) and concentrated in vacuo to afford the title compound (150 mg) as colorless oil used in the next step without purification. MS (m/z) 377.2 (M+1).

The title compound, 4-{2-[2-(3-hydroxy-4-methylheptyl)-5-oxopyrazolidin-1-yl]ethyl}benzoic acid, was prepared from intermediate 13.4 as described in Example 1 above, to provide 4-{2-[2-(3-hydroxy-4-methylheptyl)-5-oxopyrazolidin-1-yl]ethyl}benzoic acid (15 mg, 16%) was obtained as a colorless viscous oil. $^1$H NMR (methanol-$d_4$) δ 0.85-1.00 (m, 6H), 1.15-1.85 (m, 7H), 2.50-2.90 (m, 4H), 2.9-3.0 (m, 2H), 3.2-3.4 (m, 2H) 3.60-3.70 (m, 1H), 7.35 (d, J=8.06 Hz, 2H), 7.93 (d, J=8.06 Hz, 2H); MS (m/z) 363.2 (M+1).

Example 14

Synthesis of 4-{2-[2-((4S)-hydroxynonyl)-5-oxopyrazolidin-1-yl]ethyl}benzoic acid

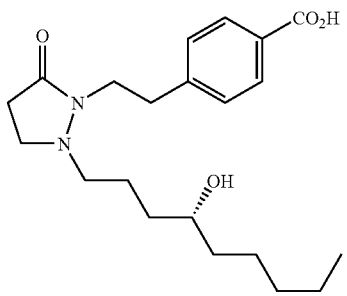

Intermediate 14.1: tert-Butyl(dimethyl){[1(S)-1 pentyl prop-2-ynyl]oxy}silanetert-Butyl.

An oven-dried flask was charged with (3S)-oct-1-yn-3 ol ((2.0 g, 0.016 mol), dry DMF (16 mL), imidazole (1.3 g, 0.019 mol) and solid tert-butyldimethylsilyl chloride (2.88 g, 0.019 mol). The resulting mixture was stirred at RT for 18 h and then diluted with ETOAc (80 mL). The organic layer was washed with a saturated solution of NH$_4$Cl (30 mL), water (4×20 mL), brine (40 mL), dried over sodium sulfate, filtered, and evaporated to afford the desired compound (4.13 g), as a yellow oil, used in the next step without further purification. R$_f$ 0.9 (EtOAc/hexanes 1/9); $^1$H NMR (CDCl$_3$) δ 0.09 (s, 3H), 012 (s, 3H), 0.91-0.84 (m, 12H), 1.30-1.27 (m, 4H), 1.43-1.36 (m, 2H), 1.68-1.62 (m, 2H), 2.36-2.35 (m, 1H), 4.33-4.30 (m, 1H).

Intermediate 14.2 4-(tert-Butyl-dimethyl-silanyloxy)-4-methyl-non-2-yn-1-ol.

To a solution of Intermediate 14.1 (4.13 g, 0.017) in dry THF (170 mL) cooled at −70° C., in a dry ice-acetone bath, was added dropwise a 1.6 M solution on n-BuLi in hexanes (13 mL, 0.021 mol) over 12 minutes. The resulting solution was stirred at −70° C. for further 0.5 h, and then solid paraformaldehyde (2.47 g, 0.082 mol) was added at once. After 10 minutes, a cooling bath was removed and the mixture stirred at RT for 18 h and then diluted with EtOAc (100 mL). The organic layer was washed with a saturated solution of NH$_4$Cl (100 mL), water (100 mL), brine (100 mL), dried over saturated sodium sulfate, filtered, and evaporated in vacuo to give a crude product. Purification on flash column chromatography (EtOAc/hexanes 1/9) afforded the desired compound (3.0 g, 65%) as a colorless oil. R$_f$ 0.15 (EtOAc/hexanes 1/9); $^1$H NMR (CDCl$_3$) δ 0.09 (s, 3H), 0.11 (s, 3H), 0.89-086 (m, 12H), 1.33-1.24 (m, 4H), 1.42-1.37 (m, 2H), 1.66-1.60 (m, 2H), 4,275 (s, 2H), 4.36 (t, J=6.59 Hz, 1H).

Intermediate 14.3: {[(1S)-4-Bromo-1-pentylbut-2-ynyl) oxy](tert-butyl)dimethylsilane To a solution of Intermediate 14.2 (420 mg, 1.56 mmol) in DCM (10 mL) were added PPh$_3$ (490 mg, 1.86 mmol, 1.2 eq) and CBr$_4$(617 mg, 1.86 mmol, 1.2 eq). The resulting solution was stirred at RT for 1 h then concentrated in vacuo. The crude residue was purified by flash column chromatography (EtOAc/hexanes 0.5/9.5) over silica gel to afford the desired compound (462 mg, 89%) as a colorless oil. $^1$HNMR (CDCl$_3$) δ 0.10 (s, 3H), 0.12 (s, 3H), 0.88-1.00 (m, 12H), 1.20-1.45 (m, 6H), 1.55-1.75 (m, 2H), 3.93 (s, 2H), 4.37 (t, J=6.4 Hz, 1H).

Intermediate 14.4: Methyl 4-{2-[2-((4S)-4-{[tert-butyl (dimethyl)siyl]oxy}non-2-ynyl)-5-oxopyrazolidin-1-yl] ethyl}benzoate.

To a solution of intermediate 1.4 (106 mg, 0.43 mmol) in DMF (8 mL) was added intermediate 14.3 (284 mg, 0.854 mmol), K$_2$CO$_3$ (178 mg, 1.29 mmol), and a catalytic amount of NaI. The resulting mixture was stirred at 50° C. for 2 h, the allowed to cool to RT overnight. The reaction mixture was diluted with ether (20 mL) and washed with water (20 mL) and brine (10 mL). The aqueous layer was extracted with ether (2×10 mL). The combined organic phase was dried over Na$_2$SO$_4$ and concentrated in vacuo. The crude mixture was purified by silica gel column chromatography (EtOAc/hexanes 1/3) to yield the title compound (80.8 mg, 38%) as a colorless oil. R$_f$ 0.14 (EtOAc/hexanes 1/3); $^1$H NMR (CDCl$_3$) δ 0.07 (s, 3H), 0.09 (s, 3H), 0.85-0.95 (m, 12H), 1.20-1.50 (m, 6H), 1.55-1.70 (m, 2H), 2.90-3.00 (m, 4H), 3.25-3.40 (broad, 2H), 3.50-3.65 (broad, 2H), 3.89 (s, 5H), 4.29-4.32 (t, J=6.2 Hz, 1H), 7.29 (d, J=7.2 Hz, 2H), 7.94 (d, J=7.2 Hz, 2H).

Intermediate 14.5: Methyl 4-{2-[2-((4S)-4-{[tert-butyl (dimethyl)siyl]oxy}nonyl)-5-oxopyrazolidin-1-yl] ethyl}benzoate A mixture of Intermediate 14.4 (80.8 mg, 0.162 mmol) and 10% Palladium on carbon (8.6 mg, 5 mol %) in MeOH (10 mL) was stirred under hydrogen atmosphere (1 atm) for 1 h. The mixture was filtered through celite and concentrated in vacuo to afford the title compound (81 mg, quantitative), which was used in the next step without purification.

Intermediate 14.6: Methyl 4-(2-{2-[(4S)-4-hydroxynonyl]-5-oxopyrazolidin-1-yl}ethyl)benzoate Intermediate 14.5 (81 mg, 0.161 mmol) was dissolved in a 4 M HCl solution in dioxane (5 mL). The resulting solution was stirred at RT for 1 h then was concentrated in vacuo to afford the free alcohol intermediate (60 mg, 96%). The crude compound was used directly for next step without further purification. MS (m/z) 391.3 (M+1).

The title compound, 4-{2-[2-((4S)-hydroxynonyl)-5-oxopyrazolidin-1-yl]ethyl}benzoic acid, was prepared from Intermediate 14.6 according to procedure described above for Example 1, to provide 4-{2-[2-((4S)-hydroxynonyl)-5-oxopyrazolidin-1-yl]ethyl}benzoic acid (38.5 mg, 48%, 3 steps) as a colorless oil. $^1$H NMR (methanol-d$_4$) δ 0.80-0.90 (m, 3H), 1.20-1.75 (m, 12H), 2.10-3.10 (m, 6H), 3.15-4.00 (m, 5H), 7.34 (d, J=8.0 Hz, 2H), 7.94 (d, J=8.0 Hz, 2H); MS (m/z) 377.3 (M+1).

Example 15

Synthesis of 4-{2-[2-((4R)-hydroxynonyl)-5-oxopyrazolidin-1-yl]ethyl}benzoic acid

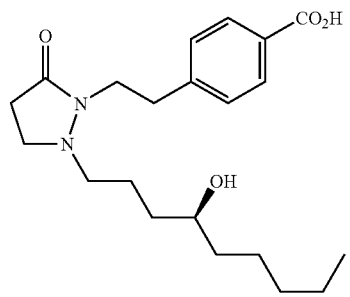

Intermediate 15.1: tert-Butyl-dimethyl-(1R-pentyl-prop-2ynyloxy)silane.

To a solution of (3R)-oct-1-yn-3-ol (1.0 g, 0.0079 mol) in dry DMF (50 mL) were added imidazole (0.84 g, 0.012 mol) and solid tert-butyldimethylsilyl chloride (1.80 g, 0.012 mol). The resulting mixture was stirred at RT for 18 h and then treated with saturated NH$_4$Cl (25 mL) and EtOAc (250 mL). The organic layer was washed with saturated NH$_4$Cl (50 mL), water (4×100 mL), brine (2×100 mL), dried over sodium sulfate, filtered, and concentrated in vacuo to afford a crude product (1.86 g, 98%), as a yellow oil, which was used in the next step without further purification. R$_f$ 0.9 (EtOAc/hexanes 1/9); $^1$H NMR (CDCl$_3$) δ 0.09 (s, 3H), 0.12 (s, 3H), 0.91-0.85 (m, 12H), 1.33-1.25 (m, 2H), 1.46-1.36 (m, J=6.59 Hz, 2H), 1.68-1.62 (m, 2H), 2.36 (d, J=1.83 Hz, 1H), 4.32 (td, J=6.59 Hz, 1.83, 1H).

Intermediate 15.2: 4-(tert-Butyl-dimethyl-silanyloxy)-non-2-yn-1-ol.

To a solution of Intermediate 15.1 (1.87 g, 0.0078) in dry THF (78 mL) cooled at −70° C., in a dry-ice acetone bath, was added dropwise a 1.6 M solution on n-BuLi in hexanes (7.0 mL, 0.011 mol) over 10 minutes. The resulting solution was stirred at −70° C. for further 0.5 h, and then solid paraformaldehyde (2.47 g, 0.0824 mol) was added at once. After 10 minutes, the cooling bath was removed, and the mixture stirred at RT for 18 h, and then diluted with EtOAc (100 mL). The organic layer was washed with a saturated solution of NH$_4$Cl (100 mL), water (100 mL), brine (100 mL), dried over saturated sodium sulfate, filtered, and evaporated in vacuo to give an oily residue which was purified on flash column chromatography (EtOAc/hexanes 1/9) to afford the desired compound (0.5 g, 23%) as a colorless oil. R$_f$ 0.06 (EtOAc/hexanes 1/9); 1H NMR (CDCl$_3$) δ 0.09 (s, 3H), 0.11 (s, 3H), 0.89-0.88 (m, 12H), 1.45-1.25 (m, 6H), 1.67-1.61 (m, 2H), 4.27 (d, J=6.22 Hz, 2H), 4.36 (t, J=6.22, 1H).

Intermediate 15.3 (4-Bromo-1-pentyl-but-2-ynyloxy)-tert-butyl-dimethyl-silane.

To a solution of Intermediate 15.2 (0.47 g, 1.23 mmol) in DCM (8.0 mL) were added PPh$_3$ (0.48 g, 1.84 mmol) and CBr$_4$ (0.61 g, 1.84 mmol). The resulting solution was stirred at RT for 1 h and then concentrated in vacuo to afford a crude product which on flash column chromatography (hexanes) gave the desired compound (0.39 g, 94%) as a colorless oil. R$_f$ 0.75, (EtOAc/hexanes 1/9). $^1$H NMR (CDCl$_3$) δ 0.09 (s, 3H), 0.12 (s, 3H), 0.88 (m, 12H), 1.31-1.25 (m, 4H), 1.45-1.35 (m, 2H), 1.67-1.61 (m, 2H), 3.92 (s, 2H), 4.36 (t, 1H).

Intermediate 15.4: 4-(2-{2-[4-(tert-Butyl-dimethyl-silanyloxy)-non-2-ynyl]-5-oxo-pyrazolidin-1-yl}-ethyl)-benzoic acid methyl ester.

To a solution of Intermediate 1.4 (0.142 g, 0.60 mmol) in DMF (20 mL) were added Intermediate 15.3 (380 mg, 1.20 mmol), $K_2CO_3$ (497 mg, 3.60 mmol) and catalytic amount of NaI. The resulting mixture was stirred at RT for 18 h and then diluted with EtOAc (80 mL). The organic layer was washed with a saturated solution of $NH_4Cl$ (20 mL), water (4×20 mL), brine (2×20 mL), dried over sodium sulfate, filtered, and evaporated in vacuo to give a crude product. Purification on flash column chromatography (EtOAc/hexanes 3/7) gave fractions of the desired compound (247.2 mg, 82.4%) as a colorless oil. $^1$H NMR (CDCl$_3$) δ 0.07 (s, 3H), 0.088 (s, 3H), 0.88-0.85 (m, 12H), 1.41-1.25 (m, 6H), 1.66-1.58 (m, 2H), 2.96 (t, J=7.32 Hz, 2H), 4.36 (t, J=6.22 Hz, 1H); MS (m/z) 501 (M+1).

Intermediate 15.5: 4-(2-{2-[4-(tert-Butyl-dimethyl-silanyloxy)-nonyl]-5-oxo-pyrazolidin-1-yl}-ethyl)-benzoic acid methyl ester.

A heterogeneous mixture of intermediate 15.4 (203.6 mg, 0.407 mmol) and 10% Palladium on carbon (10 mg) in MeOH (10 mL) was stirred under hydrogen atmosphere (1 atm) for 1 h. The mixture was filtered through celite and concentrated in vacuo to afford the title compound (151.3 mg, 74%), as a colorless oil, which was used in the next step without further purification. $^1$H NMR (CDCl$_3$) δ 0.03 (s, 3H), 0.04 (s, 3H), 0.90-0.86 (m, 12H), 1.48-1.26 (m, 10H), 2.69 (br s, 2H), 2.97 (t, J=7.32 Hz, 2H), 3.19 (br s, 2H).

Intermediate 15.6: 4-(2-{2-(4-Hydroxy-nonyl)-5-oxo-pyrazolidin-1-yl]-ethyl}-benzoic acid methyl ester.

Intermediate 15.5 (151.3 mg, 0.30 mmol) was dissolved in a 4M HCl solution in dioxane (10 mL). The resulting solution was stirred at RT for 1 h and then concentrated in vacuo to afford the title compound (115.0 mg, 98%).

The title compound, 4-{2-[2-((4R)-hydroxy-nonyl)-5-oxo-pyrazolidin-1-yl]-ethyl}benzoic acid (Example 15), was prepared from Intermediate 15.6 according to the procedure described for Example 1 above to provide 4-{2-[2-((4R)-hydroxy-nonyl)-5-oxo-pyrazolidin-1-yl]-ethyl}benzoic acid (54.3 mg, 41.7%) as a colorless viscous oil. $^1$H NMR (methanol-d$_4$) δ 0.89 (m, 3H), 1.66-1.31 (m, 8H), 2.28 (s, 2H), 2.99-2.96 (m, 2H), 3.25 (bs, 2H), 3.53 (bs, 2H), 7.33 (d, J=8.06 Hz, 1H), 7.32 (d, J=8.06 Hz, 1H), 7.94 (d, J=8.06 Hz, 1H), 9.91 (d, J=8.06 Hz, 1H); MS (m/z) 377 (M+1).

Example 16

Synthesis of 4-{2-[2-(4-Hydroxy-4-methylnonyl)-5-oxopyrazolidin-1-yl]-ethyl}-benzoic acid

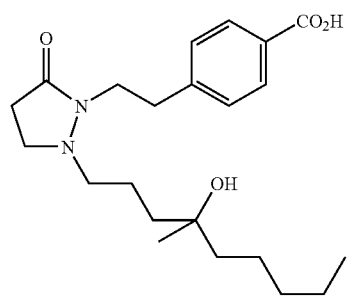

Intermediate 16.1: tert-Butyl(dimethyl)[(1-methyl-1-pentylprop-2-ynyl)oxy]sylane.

An oven-dried flask was charged with 3-methyl-oct-1-yn-3-ol (1.29 g, 9.17 mmol) and dry DMF (9.0 mL). To this solution, cooled in an ice bath, was added Et$_3$N (4.6 mL, 33.02 mmol) followed by dropwise addition of tert-butyldimethylsilyl trifluoromethanesulfonate (2.9 g, 16.5 mmol) under nitrogen. The resulting mixture was stirred at RT for 18 h and then diluted with EtOAc (80 mL). The organic layer was washed with a saturated solution of NH$_4$Cl (30 mL), water (4×20 mL), brine (40 mL), dried over sodium sulfate, filtered, and evaporated in vacuo to afford the desired compound (2.27 g, 97.6%), as a yellow oil, used in the next step without further purification. R$_f$ 0.85 (EtOAc/hexanes 1/9). $^1$H NMR (CDCl$_3$) δ 0.15 (s, 3H), 0.90-0.85 (m, 12H), 1.34-1.25 (m, 4H), 1.41 (s, 3H), 1.50-1.43 (m, 2H), 1.61-1.53 (m, 2H), 2.38 (s, 1H).

Intermediate 16.2: 4-{[tert-butyl-(dimethyl)-silyl]oxy}-4-methylnon-2-yn-1-ol.

To a solution of Intermediate 16.1 (2.3 g, 9.055 mmol) in dry THF (90 mL) cooled at –70° C., in a dry ice-acetone bath, was added dropwise a 1.6 M solution on n-BuLi in hexanes (8.0 mL, 12.8 mmol) over 15 minutes. The resulting solution was stirred at –70° C. for further 0.5 h, and then solid paraformaldehyde (2.47 g, 0.0824 mol) was added at once. After 15 minutes, the cooling bath was removed, and the mixture stirred at RT for 18 h, and then diluted with EtOAc (100 mL). The organic layer was washed with a saturated solution of NH$_4$Cl (100 mL), water (100 mL), brine (100 mL), dried over saturated sodium sulfate, filtered, and evaporated in vacuo to give an oily residue. Purification on flash column chromatography (EtOAc/hexanes 1/9) afforded the desired compound (1.70 g, 66%) as a colorless oil. R$_f$ 0.23 (EtOAc/hexanes 1/9); $^1$H NMR (CDCl$_3$) δ 0.14 (s, 3H), 0.89-0.84 (m, 12H), 1.34-1.24 (m, 4H), 1.39 (s, 3H), 1.51-1.42 (m, 2H), 1.59-1.52 (m, 2H), 4.28 (d, J=6.22 Hz, 1H).

Intermediate 16.3: [(4-Bromo-1-methyl-pentylbut-2-ynyl)oxy](tert-butyl)dimethylsilane.

To a solution of Intermediate 16.2 (1.16 g, 4.084 mmol) in dichloromethane (14 mL) were added PPh$_3$ (1.93 g, 7.35 mmol) and CBr$_4$ (2.44 g, 7.35 mmol). The resulting solution was stirred at RT for 1 h and then concentrated in vacuo to afford a crude product which on flash column chromatography (hexanes) gave the desired compound (1.40 g, 99%) as a colorless oil. R$_f$ 0.78, (EtOAc/hexanes 1/9); $^1$H NMR (CDCl$_3$) δ 0.15 (s, 3H), 0.90-0.84 (m, 12H), 1.32-1.26 (m, 2H), 1.45-141 (m, 2H), 1.38 (s, 3H), 1.60-1.54 (m, 4H), 3.93 (s, 3H).

Intermediate 16.4: Methyl 4-{2-[2-(4-{[tert-butyl(dimethyl)silyl]oxy}-4-methylnonyl)-5-oxopyrazolidin-1-yl]ethyl}benzoate.

To a solution of Intermediate 1.4 (142.6 mg, 0.575 mmol) in DMF (5.0 mL) were added the intermediate 16.3 (397.9 mg, 1.15 mmol), K$_2$CO$_3$ (477.0 mg, 1.38 mmol) and catalytic amount of NaI. The resulting mixture was stirred at RT for 18 h and then diluted with EtOAc (80 mL). The organic layer was washed with a saturated solution of NH$_4$Cl (2×20 mL), water (4×20 mL), brine (20 mL), dried over sodium sulfate, filtered, and evaporated in vacuo to give a crude product. Purification on flash column chromatography (EtOAc/hexanes 3/7) gave the desired compound (171.0 mg, 63.4%) as a colorless oil. $^1$H NMR (CDCl$_3$) δ 0.11 (s, 6H), 0.86-0.82 (m, 12H), 1.30-1.23 (m, 4H), 1.52-1.40 (m, 2H), 1.58-1.52 (m, 2H), 2.95 (t, J=7.32 Hz, 2H), 3.31 (br s, 2H), 3.56 (br s, 2H), 3.38 (s, 3H), 7.28, (d, J=8.06 Hz, 2H), 7.95 (d, J=8.06 Hz, 2H).

Intermediate 16.5: Methyl 4-{2-[2-(4-hydroxy-4-methyl-nonyl)-5-oxopyrazolidin-1-yl]ethyl}benzoate.

A heterogenous mixture of intermediate 16.4 (171.0 mg, 0.333 mmol) and 10% Palladium on carbon (10 mg) in MeOH (5.0 mL) was stirred under hydrogen atmosphere (1 atm) for 3 h. The mixture was filtered through celite and concentrated in vacuo to afford the title compound (116.7 mg, 68%), as a colorless oil, which was used in the next step without further purification. $^1$H NMR (CDCl$_3$) δ (0.06 (s, 6H), 0.85 (m, 12H), 1.16 (s, 3H), 1.60-1.25 (m, 12H), 2.65 (br t, 2H), 2.98-2.94 (br t, 2H), 3.13 (br s, 2H), 3.88 (s, 3H), 2.28 (d, J=8.06 Hz, 2H), 7.94 (d, J=8.06 Hz, 2H); MS (m/z) 519 (M+1).

Intermediate 16.6: 4-{2-[2-(4-Hydroxy-4-methyl-nonyl)-5-oxo-pyrazolidin-1-yl]-ethyl}-benzoic acid methyl ester.

Intermediate 16.5 (116.7 mg, 0.226 mmol) was dissolved in a 4M HCl solution in dioxane (10 mL). The resulting solution was stirred at RT for 0.5 h and then the solvent evaporated in vacuo to afford the title compound (99.0 mg, 0.224 mmol, 99.4%) used in the next step without further purification.

The title compound 4-{2-[2-(4-Hydroxy-4-methylnonyl)-5-oxopyrazolidin-1-yl]-ethyl}-benzoic acid (Example 16), was prepared from Intermediate 16.6 according to the procedure described for Example 1 to provide 4-{2-[2-(4-Hydroxy-4-methylnonyl)-5-oxopyrazolidin-1-yl]-ethyl}-benzoic acid (18.8 mg, 21.3%) as a colorless viscous oil. $^1$H NMR (methanol-d$_4$) δ 0.90 (t, J=6.59 Hz, 3H), 1.14 (s, 2H), 1.55-1.28 (m, 10H), 2.78 (br t, H), 2.98 (t, J=6.96 Hz, 2H), 3.24 (br t, 2H), 3.30 (m, 1H), 7.34 (d, J=8.42 Hz, 2H), 7.93 (d, J=8.42 Hz, 2H); MS (m/z) 391 (M+1).

Example 17

Synthesis of 4-{2-[2-(3-cyclobutyl-3-hydroxypropyl)-5-oxopyrazolidin-1-yl]ethyl}benzoic acid

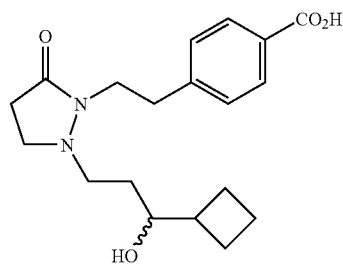

Intermediate 17.1: N,N-diethylcyclobutanecarboxamide.

To a solution of diethyl amine (2.19 g, 30 mmol) and Et$_3$N (3.33 g, 33 mmol) in THF (50 ml) was added dropwise cyclobutanecarboxyl chloride (3.56 g, 30 mmol) at 0° C. The reaction mixture was stirred at RT for 1 h and the precipitate was filtered out and THF was removed by in vacuo. The resulting oil was dissolved into EtOAc (100 mL), washed with 0.2 N HCl (100 mL), 5% NaHCO$_3$ (100 mL), brine (100 mL), dried (MgSO$_4$) and concentrated in vacuo to afford the title compound (4.4 g, 95% yield) as light yellow oil used in the next step without purification. $^1$H NMR (CDCl$_3$) δ 1.1 (m, 6H), 1.7-2.3 (m, 6H), 3.2 (m, 3H), 3.3 (q, J=7.32 Hz, 2H).

Intermediate 17.2: 1-cyclobutylprop-2-en-1-one.

To a solution of Intermediate 17.1 (500 mg, 3.3 mmol) in THF at 0° C. was added vinyl magnesium bromide (9.9 mL, 1.0 M in THF solution) dropwise and the reaction mixture was stirred at 0° C. for 0.5 h. The reaction temperature was slowly raised to RT over a period of 2 h and was quenched with NH$_4$Cl saturated solution. The resulting reaction mixture was extracted with EtOAc (50 mL), washed with 0.2N HCl (50 mL), 5% NaHCO$_3$ (50 mL), brine (50 mL), dried (MgSO$_4$), and concentrated to afford the title compound (60 mg) as colorless oil used in the next step without purification.

Intermediate 17.3: methyl 4-{2-[2-(3-cyclobutyl-3-oxopropyl)-5-oxopyrazolidin-1-yl]ethyl}benzoate To a solution of Intermediate 17.2 (60 mg, 0.55 mmol) in isopropanol (10 ml) was added Intermediate 1.4 (75 mg, 0.30 mmol) and Et$_3$N (94 µl, 0.30 mmol) and the reaction mixture was refluxed for 2 h. The reaction mixture was then concentrated under reduced pressure and was dissolved into EtOAc (40 mL). The organic layer was washed with 1N HCl solution (40 mL), 5% NaHCO$_3$ (40 mL), brine (40 mL), dried over Na$_2$SO$_4$ and evaporated under reduced pressure. The crude product was then purified by flash column chromatography (EtOAc) to give the title compound as colorless oil (25 mg). R$_f$ 0.2 (EtOAc); MS (m/z) 359.2 (M+1).

Intermediate 17.4: methyl 4-{2-[2-(3-cyclobutyl-3-hydroxypropyl)-5-oxopyrazolidin 1-yl]ethyl}benzoate.

To a solution of Intermediate 17.3 (25 mg, 0.07 mmol) in MeOH (2 ml) at −15° C. was added CeCl$_3$.6H$_2$O (26 mg, 0.07 mmol) in water (1 ml). Then NaBH$_4$ (4 mg, 0.11 mmol) was added in one portion. The reaction mixture was stirred for 15 minutes and the mixture was evaporated, dissolved in EtOAc, washed with brine and dried (NaSO$_4$) to afford the title compound (20 mg) as colorless oil used in the next step without purification. MS (m/z) 361.2 (M+1).

The title compound, 4-{2-[2-(3-cyclobutyl-3-hydroxypropyl)-5-oxopyrazolidin-1-yl]ethyl}benzoic acid (Example 17), was prepared as follows. To a solution of Intermediate 17.4 (20 mg, 0.06 mmol) in THF/MeOH/water (10 ml, 3:3:1) was added NaOH (20 mg, 0.5 mmol) and the mixture was stirred for 4 h. The solution was acidified to pH=2-3 with 1N HCl solution and the crude mixture was purified by preparative HPLC to give the title compound (9 mg, 43%) as colorless oil. $^1$H NMR (methanol-d$_4$) δ 0.4 (m, 1H), 1.6 (m, 1H), 1.75-2.10 (m, 6H), 2.40 (m, 1H), 2.90 (m, 2H), 3.0 (t, J=6.96 Hz, 2H), 3.2 (m, 6H) 3.50 (m, 1H), 7.34 (d, J=8.06 Hz, 2H), 7.90 (d, J=8.42 Hz, 2H); MS (m/z) 347.2 (M+1).

Example 18

Synthesis of 4-[2-(2-{4-[1-(cyclopropylmethyl)cyclobutyl]-4-hydroxybutyl}-5-oxopyrazolidin-1-yl)ethyl]benzoic acid

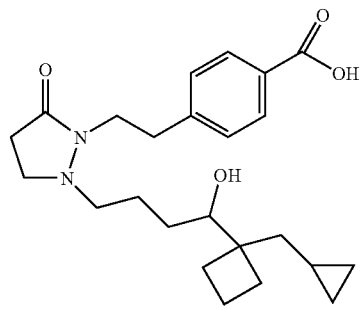

Intermediate 18.1: 1-(cyclopropylmethyl)cyclobutanecarboxylic acid

To a solution of LDA (100 ml, 2.0 M THF solution) in THF (100 ml) was added dropwise over a period of 20 minutes at 0° C., a solution of cyclobutane carboxylic acid (10 g, 0.1 mol) in THF (15 ml). The resulting mixture was stirred at RT for 2 h then bromoethylcyclopropane (15 g, 0.11 mol) was added dropwise and the mixture was stirred at RT. overnight. To the reaction mixture was added 2N HCl and the mixture was extracted with EtOAc. The organic layer was washed with water and brine to afford the title compound as light yellow oil (19.2 g), which was used in the next step without purification.

Intermediate 18.2: [1-(cyclopropylmethyl)cyclobutyl] methanol

To a solution of lithium aluminum hydride (150 ml, 1.0 M THF solution) was added dropwise a solution of intermediate 18.1 in THF (25 ml) and the mixture was refluxed for 0.5 h. The reaction mixture was cooled with ice and was added ether, followed by adding a saturated solution of sodium sulfate (25 ml) slowly. The mixture was stirred at RT until it became a white suspension, then was added sodium sulfate and the mixture was filtered and the filtrate was concentrated. The crude residue was purified by flash column chromatography (EtOAc/hexanes) to afford the title compound (8.83 g) as colorless oil. $R_f$ 0.40 (EtOAc/hexanes 1/5); $^1$H NMR (CDCl$_3$) d: 0.05 (m, 2H), 0.42 (m, 2H), 0.62 (m, 1H), 1.42 (d, J=6.96 Hz, 2H), 1.78-1.84 (m, 6H), 3.64 (s, 2H).

Intermediate 18.3:1-(cyclopropylmethyl)cyclobutanecarbaldehyde.

To a solution of oxalyl chloride (47 ml, 2.0 M solution in DCM, 0.024 mol) in DCM (100 ml) at −78° C. was added dropwise a solution of DMSO (13.4 ml) in DCM (12 ml) and the mixture was stirred at that temperature for 30 minutes. To this solution was added dropwise a solution of intermediate 18.2 (8.8 g) in DCM (12 ml) and the temperature was raised to −40° C. over a period of 30 minutes. To this solution was added dropwise Et$_3$N (53 mL) and the temperature was raised to 0° C. over a period of one. hour. To the reaction mixture was added water and 2N HCl and the mixture was extracted with DCM. The organic layer was washed by water and brine, dried over anhydrous magnesium sulfate to afford the title compound as yellow oil, which was used in the next step without further purification. Rf 0.7 (EtOAC/haxane 1/5).

Intermediate 18.4:1-[1-(cyclopropylmethyl)cyclobutyl] prop-2-yn-1-ol

To a solution of intermediate 18.3 in THF (50 ml) at −60° C. was added dropwise ethynylmagnesium bromide (400 ml, 0.5 M in THF solution) and the solution was stirred for 30 minutes allowing the temperature to reach 0° C. The reaction was quenched at −60° C. with saturated ammonium chloride solution (40 ml) and warmed to room temperature. The aqueous layer was extracted with EtOAc. The combined organic portions were washed with brine, dried over magnesium sulfate, filtered, and concentrated to afford the title compound as s light yellow oil, which was used in the next step without further purification.

Intermediate 18.5: tert-butyl({1-[1-(cyclopropylmethyl)cyclobutyl]prop-2-ynyl}oxy)dimethylsilane To a solution of intermediate 18.4 (7.86 g, 0.048. mol) in dry DMF (160 mL) was added imidazole (16.25 g, 0.34 mol) and tert-butyldimethylsilyl chloride (18.0 g, 0.119 mol). The mixture was stirred at RT. The reaction was quenched with saturated aqueous solution of ammonium chloride and diluted with ethyl acetate. The organic layer was washed with saturated ammonium chloride, water, brine, dried over sodium sulfate, and evaporated in vacuum to give an oily residue which was purified by flash column chromatography to afford the title compound (3.44 g) as colorless oil. $^1$H NMR (CDCl$_3$) d: 0.10 (m, 2H), 0.11 (s, 3H), 0.15 (s, 3H), 0.44 (d, J=7.69 Hz, 2H), 0.71 (m, 1H), 0.91 (s, 9H), 1.36 (d, J=Hz, 2H), 1.80 (m, 4H), 2.08 (m, 2H), 2.30 (s, 1H), 4.40 (s, 1H).

Intermediate 18.6: 4-{[tert-butyl(dimethyl)silyl]oxy}-4-[1-(cyclopropylmethyl)cyclobutyl]but-2-yn-1-ol To a solution of intermediate 18.5 (3.44 g, 12.4 mmol) in THF (100 ml) at −78° C. was added dropwise n-BuLi (9.3 ml, 1.6 M in hexanes) over a period of 10 minutes. The reaction mixture was stirred for 30 minutes before paraformaldehyde (1.49 g, 49.6 mmol) was added in one portion. After the mixture was stirred for 10 minutes, the cooling bath was removed and the mixture was stirred at RT for 18 hours. The resulting mixture was quenched with saturated solution of ammonium chloride and EtOAc. The organic layer was washed with water and brine, dried with magnesium sulfate, concentrated and purified by flash column chromatography to afford the title compound (2.37 g, 52% yield) as colorless oil. $R_f$ 0.6 (EtOAc/hexanes 1/4) $^1$H NMR (CDCl$_3$) d: 0.10 (m, 2H), 0.11 (s, 3H), 0.15 (s, 3H), 0.44 (m, 2H), 0.71 (m, 1H), 0.91 (s, 9H), 1.31 (m, 1H), 1.62 (m, 1H), 2.04 (m, 4H), 4.28. (s, 2H), 4.43 (s, 1H).

Intermediate 18.7: ({4-bromo-1-[1-(cyclopropylmethyl)cyclobutyl]but-2-ynyl}oxy)(tert-butyl)dimethylsilane To a solution of intermediate 18.6 (590 mg, 1.92 mmol) in DCM (10 ml) was added CBr$_4$ (700 mg, 2.11 mmol) and PPh$_3$ (604 mg, 2.30 mmol). The resulting solution was stirred at RT for 1 hour. Concentration of the reaction followed by flash column chromatography afforded the title compound (640 mg, 90% yield) as colorless oil. $R_f$ 0.9 (EtOAc/hexanes 1/9). $^1$H NMR (CDCl$_3$) d: 0.10 (m, 2H), 0.11 (s, 3H), 0.15 (s, 3H), 0.44 (m, 2H), 0.71 (m, 1H), 0.91. (s, 9H), 1.31 (m, 1H), 1.62. (m, 1H), 2.04 (m, 4H), 3.90 (s, 2H), 4.43 (s, 1H).

Intermediate 18.8: methyl 4-[2-(2-{4-([tert-butyl(dimethyl)silyl]oxy}-4-[1-(cyclopropylmethyl)cyclobutyl]butyl)-5-oxopyrazolidin-1-yl)ethyl]benzoate To a solution of intermediate 18.7 (640 mg, 1.72 mmol) in DMF (10 ml) was added intermediate 1.4 (287 mg, 1.16 mmol), K$_2$CO$_3$ (962 mg, 6.96 mmol) and KI (catalytic amount) at room temperature. The resulting mixture was stirred for 2 and a half days. DMF was removed under reduced pressure and the resulting residue was dissolved in EtOAc, washed with water and brine, dried (MgSO$_4$), concentrated and purified by flash column chromatography to afford the title compound (309 mg, 49% yield) as colorless oil. $R_f$ 0.6 (EtOAc/hexanes 1:1). $^1$H NMR (CDCl$_3$) d: 0.06 (m, 2H), 0.08 (s, 3H), 0.12 (s, 3H), 0.42 (m, 2H), 0.70 (m, 1H), 0.90 (s, 9H), 1.31 (m, 1H), 1.58 (s, 2H), 1.62 (m, 1H), 1.80 (m, 4H), 2.01 (m, 2H), 3.0 (m, 4H), 3.30 (m, 2H), 3.59 (m, 2H), 3.90 (s, 3H), 4.37 (s, 1H), 7.29 (d, J=8.42 Hz, 2H), 7.95 (d, J=8.06 Hz, 2H).

Intermediate 18.9: methyl 4-[2-(2-{4-[1-(cyclopropylmethyl)cyclobutyl]-4-hydroxybutyl}-5-oxopyrazolidin-1-yl)ethyl]benzoate To a solution of intermediate 18.8 (309 mg, 0.574 mmol) in MeOH (10 ml) was added 105 palladium on carbon (30 mg) and 1 drop of concentrated HCl. The resulting mixture was stirred under hydrogen atmosphere for 18 hours. The mixture was filtered through Celite and concentrated to afford the title compound (230 mg) methyl 4-[2-(2-{4-[1-(cyclopropylmethyl)cyclobutyl]-4-hydroxybutyl}-5-oxopyrazolidin-1-yl) ethyl]benzoate, as colorless oil MS (m/z) 429 (M+1).

The title compound 4-[2-(2-{4-[1-cyclopropylmethyl)cyclobutyl]-4-hydroxybutyl}-5-oxopyrazolidin-1yl)ethyl]benzoic acid (Example 18) was prepared as follows. To a solution of intermediate 18.9 (230 mg, 0.54 mmol) in 6 ml of MeOH/THF (1:1) at room temperature was added NaOH (216 mg, 5.4 mmol) in water (1 ml). The resulting mixture was stirred for 2 hours. The solution was acidified to pH=2-3 with 1 N HCl solution and the crude mixture was purified by preparative RP-HPLC to give the title compound (60 mg, 27%)

4-[2-(2-{4-[1-(cyclopropylmethyl)cyclobutyl]-4-hydroxybutyl}-5-oxopyrazolidin-1-yl)ethyl]benzoic acid as white powder. $^1$H NMR (methanol-$d_4$) d: 0.06 (m, 2H), 0.44 (d, 2H), 0.80 (m, 1H), 1.28 (m, 2H), 1.54 (m, 3H), 1.78-1.98 (m, 6H), 1.80 (m, 4H), 2.80 (m, 2H), 3.0 (t, 2H), 3.30 (m, 2H), 3.60 (m, 1H), 7.29 (d, J=8.42 Hz, 2H), 7.95 (d, J=8.06 Hz, 2H) MS (m/z) 415.2 (M+1).

Example 19

4-(2-{2-[4-(1-ethylcyclobutyl)-4-hydroxybutyl}-5-oxopyrazolidin-1-yl}ethyl)benzoic acid

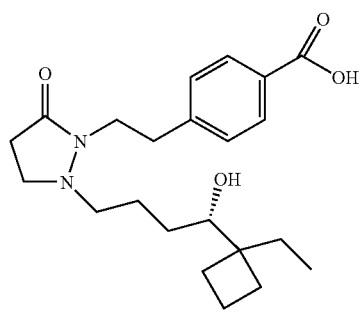

Intermediate 19.1: 1-ethylcyclobutanecarboxylic acid

To a solution of LDA (100 ml; 2.0 M THF solution) in THF (100 ml) was added dropwise over a period of 20 minutes under cooling with ice, a solution of cyclobutane carboxylic acid (10 g, 0.1 mol) in THF (15 ml) and the mixture was stirred at RT for 2 h. To the mixture iodoethane (15.6 g, 0.1 mol) was added dropwise and the mixture was stirred at RT overnight. To the reaction mixture was added 2N HCl and the mixture was extracted with ethyl acetate. The organic layer was washed with water and brine to afford the title compound as a light yellow oil (22.4 g), which was used in the next step without purification.

Intermediate 19.2: (1-ethylcyclobutyl)methanol

To a solution of lithium aluminum hydride (150 ml, 1.0 M THF solution) was added dropwise a solution of intermediate 19.1. in THF (25 ml) and the mixture was refluxed for 0.5 h. The reaction mixture was cooled with ice then diluted with ether, followed by the slow addition of a saturated solution of sodium sulfate (25 ml). The mixture was stirred at RT until it became a white suspension, then was added sodium sulfate and the mixture was filtered and the filtrate was concentrated. The crude residue was purified by flash column chromatography (EtOAc/hexanes) to afford the title compound (6.5 g) as colorless oil. $R_f$ 0.40 (EtOAc/hexanes 1/4); $^1$H NMR (CDCl$_3$) d: 0.81 (t, J=7.32 Hz, 3H), 1.51 (q, J=7.32 Hz, 2H), 1.68-1.85 (m, 6H), 3.52 (s, 2H).

Intermediate 19.3: 1-ethylcyclobutanecarbaldehyde

To a solution of oxalyl chloride (42.8 ml, 2.0 M solution in DCM) in DCM (100 ml) at −78° C. was added dropwise a solution of dimethylsulfoxide (12.1 ml) in methylene chloride (12 ml) and the mixture was stirred at that temperature for 30 minutes. To this solution was added dropwise a solution of intermediate 19.2 (6.5 g) in DCM (12 ml) and the temperature was raised to −40° C. over a period of 30 minutes. To this solution was added dropwise ET$_3$N (48 ml) and the temperature was raised to 0° C. over a period of one h. To the reaction mixture was added water and 2N HCl and the mixture was extracted with DCM. The organic layer was washed by water and brine, dried over anhydrous magnesium sulfate to afford the title compound as yellow oil, which will be used in the next step quickly without purification. $R_f$ 0.7 (EtOAC/hexanes 1/5).

Intermediate 19.4: 1-(1-ethylcyclobutyl)prop-2-yn-1-ol

To a solution of intermediate 19.3 in THF (50 ml) at −60° C. was added dropwise a solution of ethylnylmagnesium bromide (342 ml, 0.5 M in THF solution) and the solution was stirred for 30 minutes allowing the temperature to reach 0° C. The mixture was quenched at −60° C. with saturated ammonium chloride solution (40 ml) and warmed to RT. The aqueous layer was extracted with ethyl acetate. The combined organic portions were washed with brine, dried over magnesium sulfate, filtered, and concentrated to afford the title compound as s light yellow oil, which was used quickly in the next step without purification. $R_f$ 0.5 (EtOAc/hexanes 1/5).

Intermediate 19.5: tert-butyl {[1-(1-ethylcyclobutyl)prop-2-ynyl]oxy}dimethylsilane To a solution of 19.4 (8.5 g, 52 mmol) in DMF at RT was added imidazole (4.28 g, 63 mmol) and tert-butyldimethylsilyl chloride (9.50 g, 63.0 mmol). The resulting mixture was stirred at RT for 18 hours. The resulting precipitate was filtered and DMF was removed in vacuo. A saturated solution of NH$_4$Cl was added and the mixture extracted with EtOAc (2×). The collected organic phase was washed with water and brine, dried with MgSO$_4$, concentrated and purified by flash column chromatography to give the title compound (9.2 g, 64% yield for the above 3 steps) as colorless oil. $R_f$ 0.8 (hexanes); $^1$H NMR (CDCl$_3$) d: 0.10 (s, 3H), 0.15 (s, 3H), 0.88-0.90 (m, 12H), 1.26 (m, 2H), 1.66 (m, 2H), 1.76 (m, 2H), 2.05 (m, 2H), 2.35. (s, 1H, 4.22 (s, 1H).

Intermediate 19.6: 4-{[tent-butyl(dimethyl)silyl]oxy}-4-(1-ethylcyclobutyl)but-2-yn-1-ol To a solution of intermediate 19.5. (9.2 g, 36.4 mmol) in THF (100 ml) at −78° C. was added dropwise a solution of n-BuLi (27.3 ml, 1.6 M in hexanes) over a period of 10 minutes. The reaction mixture was stirred for 30 minutes before paraformaldehyde (4.37 g, 145.6 mmol) was added in one portion. After the mixture was stirred for 10 minutes, the cooling bath was removed and the mixture was stirred at room temperature for 18 hours. The resulting mixture was treated with saturated ammonium chloride and EtOAc. The organic layer was washed with water and brine, dried with magnesium sulfate, concentrated and purified by flash column chromatography to afford the title compound (6.8 g, 66% yield) as colorless oil. $R_f$ 0.6 (EtOAc/hexanes 1/4); $^1$H NMR (CDCl$_3$) d: 0.09 (s, 3H), 0.15 (s, 3H), 0.87 (t, J=7.32 Hz, 3H), 0.90 (s, 9H), 1.52 (m, 2H), 1.64 (m, 2H), 1.66. (m, 2H), 1.76 (m, 2H), 2.03 (m, 2H), 4.26 (s, 1H), 4.28 (s, 1H).

Intermediate 19.7: {[4 bromo-1-(1-ethylcyclobutyl)but-2-ynyl]oxy}(tert-butyl)dimethylsilane To a solution of intermediate 19.6 (0.328 g, 1.048 mmol, 1.0 eq) in DCM (9.0 mL, 0.12 M) were added PPh$_3$ (0.373 g, 1.38 mmol, 1.2 eq) and CBr$_4$ (0.456 g, 1.38 mmol, 1.2 eq). The resulting solution was stirred at RT for ½ h and then concentrated in vacuo. The crude product was purified by flash column chromatography (hexanes) to afford fractions of the desired compound (0.365 g, 1.04 mmol, 100%) as colorless oil. $R_f$ 0.68, (EtOAc/hexanes 1/9); $^1$H NMR (CDCl$_3$) d: 0.09 (s, 3H), 0.15 (s, 3H), 0.89 (t, J=7.32 Hz, 3H), 0.90 (s, 9H), 1.56 (m, 2H), 1.64 (m, 2H), 1.66 (m, 2H), 1.76 (m, 2H), 2.03 (m, 2H), 3.93 (s, 2H), 4.25 (s, 1H).

Intermediate 19.8: methyl 4-(2-{2-[4-{[tert-butyl(dimethyl)silyl]oxy}-4-(1-ethylcyclobutyl)butyl]-5-oxopyrazolidin-1-yl}ethyl)benzoate To a solution of intermediate 19.7 (307.3 mg, 0.883 mol) in DMF (3.0 mL, 0.1 M) were added 1.4 (130 mg, 0.524 mmol), K$_2$CO$_3$ (386 mg, 2.80 mmol) and catalytic amount of NaI The resulting mixture was stirred at RT for 18 h and then diluted with EtOAc (25 mL). The organic layer was washed with a saturated solution of NH$_4$Cl (2×10 mL), water (4×10 mL), brine (2×10 mL), dried over sodium sulfate, filtered, and evaporated in vacuo to give a crude product (311.2 mg) which on flash column chromatography (EtOAc/hexanes 3/7) gave. fractions of the desired compound (241.2 mg, 0.483 mmol, 92.2%) as a yellow oil. $^1$H NMR (CDCl$_3$) d: 0.07 (s, 3H), 0.11 (s, 3H), 0.89 (t, J=7.32 Hz, 3H), 0.90 (s, 9H), 1.56 (m, 2H), 1.64 (m, 2H), 1.66 (m, 2H), 1.76 (m, 2H), 2.03 (m, 2H), 2.95 (t, 2H), 3.3 (m, 2H), 3.59 (m, 2H), 3.89 (s, 3H), 4.20 (s, 1H), 7.28 (d, J=8.42. Hz, 2H), 7.94 (d, J=8.06 Hz, 2H).

Intermediate 19.9: methyl 4-(2-{2-[4-{(ter-butyl(dimethyl)silyl]oxy}-4-(1-ethylcyclobutyl)butyl]-5-oxopyrazolidin-1-yl}ethyl)benzoate.

A heterogeneous mixture of intermediate 19.8. (105.7 mg, 0.294 mmol) and 10% Palladium on carbon (10 mg) in MeOH (5.0 mL) was stirred under hydrogen atmosphere (1 atm) for 1 h. The mixture was filtered through celite and concentrated in vacuo to afford the title compound (122 mg, 80.3%), as a colorless oil, which was used in the next step without further purification.

Intermediate 19.10: methyl 4-(2-{2-[4-(1-ethylcyclobutyl)-4-hydroxybutyl]-5-oxopyrazolidin-1-yl}ethyl)benzoate Intermediate 19.9 (122.0 mg, 0.236 mmol) was dissolved in a 4M HCl solution in dioxane (10 mL). The resulting solution was stirred at room temperature for 1 hour and then concentrated in vacuo to afford the title compound (101 mg, 97.5%) 4-(2-{2-[4-(1-ethylcyclobutyl)-4-hydroxybutyl}-5-oxopyrazolidin-1-yl}ethyl)benzoic acid.

The title compound 4-(2-{2-[4-(1-ethylcyclobutyl)-4-hydroxybutyl}-5-oxopyrazolidin-1-yl}ethyl)benzoic acid (Example 19) was prepared as follows. To a solution of intermediate 19.10 (101.0 mg, 0.251 mmol) in MeOH (3 mL), THF (3 mL), and water (1 mL) was added NaOH (16.0 mg, 1.6 mmol). The resulting solution was stirred at RT for 8 h then concentrated under reduced pressure. The crude mixture was purified by RP-HPLC using ACN/H$_2$0 and 0.1% TFA to afford the title compound (55.4 mg, 0.123 mmol, 49%) 4-(2-{2-[4-(1-ethylcyclobutyl)-4-hydroxybutyl]-5-oxopyrazolidin-1-yl}ethyl)benzoic acid as a colorless oil. $^1$H NMR (methanol-d$_4$) d 0.92 (t, 3H), 1.30 (m, 8H), 1.98-2.0 (m, 2H), 2.81 (t, 2H), 2.99 (m, 2H), 3.25 (m, 2H), 3.45 (d, J=9.89 Hz, 1H), 7.29 d, J=8.42 Hz, 2H), 7.95. (d, J=8.06. Hz, 2H); MS (m/z) 389 (M+1).

Example 20

4-(2-{2-[3-hydroxy-4-(3-methylphenyl)butyl]-5-oxopyrazolidin-1-yl}ethyl)benzoic acid

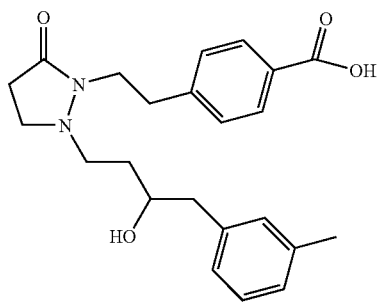

Intermediate 20.1: N-methoxy-N-methyl-2-(3-methylphenyl)acetamide

To a solution of (3-methylphenyl)acetic acid (1.0 g, 6.7 mmol) in DMF (20 mL0 were added N,O-dimethylhydroxylamine hydrochloride (0.78 g, 8.04 mmol), EDC (1.54 g, 8.04 mmol), HOBt (1.06 g, 8.04 mmol), and N,N-diisopropylethylamine (7.0 mL, 40.2 mmol). The solution was stirred at RT for 18 h then diluted with EtOAc (150 mL) and washed with HCl 1 M (100 mL), water (100 mL), saturated solution of NaHCO$_3$ (100 mL), and brine (100 mL). The organic solution was dried over sodium sulfate and concentrated in vacuo to afford the desired amide (1.2 g, 98%) used in the next step without further purification. R$_f$ 0.8 (EtOAc/hexanes 1/1).

Intermediate 20.2: 1-(3-methylphenyl)but-3-en-2-one

To a solution of intermediate 20.1 (1.2 g ml; 6.2 mmol) in THF (50 ml) was added dropwise at 0° C. a THF solution of vinylmagnesium bromide (6.2 mL, 11.0M, 6.2 mmol). The mixture was stirred at 0° C. for an additional hour then was quenched with a saturated solution of NH4Cl (100 mL). The resulting mixture was extracted with EtOAc (2×100 mL). The collected organic phase was washed with brine (100 mL), dried over sodium sulfate and concentrated in vacuo to afford the desired enone (1.1 g) used in the next step without further purification.

Intermediate 20.3: methyl 4-(2-{2-[4-(3-methylphenyl)-3-oxobutyl]-5-oxopyrazolidin-1-yl}ethyl)benzoate.

To a solution of the Intermediate 1.4 (0.46 g, 1.86 mmol) and Intermediate 20.2 (1.2 g) in EtOH was added Et$_3$N (0.47 mL, 3.4 mmol). The resulting solution was stirred at reflux for 2 h then concentrated in vacuo and the crude oil purified by flash column chromatography (EtOAc/hexanes) to afford the title compound (0.21 g, 27%) as a colorless oil. R$_f$ 0.3 (EtOAc/hexanes 4/1); MS (m/z) 409.5 (M+1).

Intermediate 20.4: methyl 4-(2-{2-[3-hydroxy-4-(3-methylphenyl)butyl]-5-oxopyrazolidin-1-yl}ethyl)benzoate.

To a solution of Intermediate 20.3 (0.20 g, 0.49 mmol) in THF (6 mL) were added at −15° C. a THF solution of (R)-CBS (0.25 mL, 1 M, 0.25 mmol) followed by a THF solution of BH$_3$.THF (0.51 mL, 1 M, 0.51 mmol). After 10 minutes the reaction was allowed to warm up and stirred at RT for an additional 18 h. The reaction mixture was diluted with EtAOc (50 mL) and washed a saturated solution of NaHCO3 (50 mL), brine (50 mL), dried and concentrated in vacuo to afford the crude compound used in the next without further purification. MS (m/z) 411.5 (M+1).

The title compound 4-(2-{2-[3-hydroxy-4-(3-methylphenyl)butyl]-5-oxopyrazolidin-1-yl}ethyl)benzoic acid (Example 20) was prepared as follows.

To a solution of Intermediate 20.4 in water (2 mL), MeOH (6 mL), and THF (6 mL) was added NaOH (64 mg, 1.6 mmol). The resulting solution was stirred at RT for 8 h then concentrated under reduced pressure. The crude mixture was purified by RP-HPLC using ACN/H$_2$O/to afford the desired compound as a white solid. $^1$H NMR (methanol-d$_4$) δ 1.50-1.80 (m, 2H), 2.30 (s, 3H), 2.65-2.82 (m, 2H), 2.85-3.00 (m, 4H), 3.10-3.20 (m, 2H), 3.40-3.85 (m, 2H), 3.85-3.98 (m, 1H), 6.98-7.18 (m, 4H), 7.33 (d, 2H), 7.92 (d, 2H); MS (m/z) 397.5 (M+1).

Example 21

4-{2-[2-(3-hydroxy-4-phenylbutyl)-5-oxopyrazolidin-1-yl]ethyl}benzoic acid

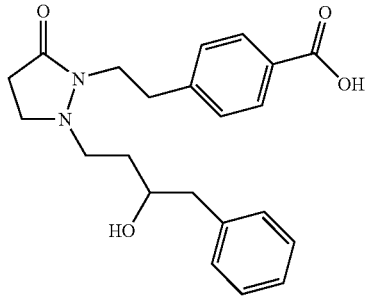

Example 21 was prepared using the procedures of Example 20 starting from phenylacetic acid to give 21 as a white solid. $^1$H NMR (methanol-$d_4$) δ 1.45-1.75 (m, 2H), 2.70-3.05 (m, 12H), 3.10-3.20 (m, 2H), 3.90-3.98 (m, 1H), 7.15-7.40 (m, 6H), 7.85-8.00 (d, 2H); MS (m/z) 383.5 (M+1).

Example 22

4-(2-{2-[3-hydroxy-4-(3-iodophenyl)butyl]-5-oxopyrazolidin-1-yl}ethyl)benzoic acid

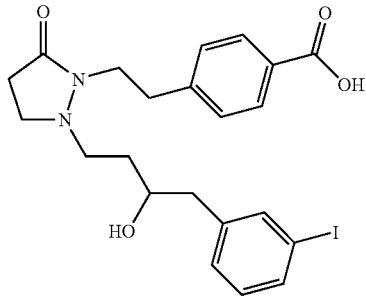

Example 22 was prepared using the procedures of Example 20 starting from (3-iodophenyl)acetic acid to give 22 as a white solid. $^1$H NMR (methanol-$d_4$) δ 1.50-1.68 (m, 2H), 2.20-2.65 (m, 2H), 2.70-2.80 (m, 2H), 2.85-3.10 (m, 4H), 3.10-3.25 (m, 2H), 3.25-3.45 (m, 5H), 3.85-4.00 (m, 1H), 7.07 (t, 1H), 7.20-7.40 (m, 3H), 7.50-7.70 (m, 2H), 7.93 (d, 2H); MS (m/z) 509 (M+1).

Example 23

4-(2-{2-[4-(3-bromophenyl)-3-hydroxybutyl]-5-oxopyrazolidin-1-yl}ethyl)benzoic acid

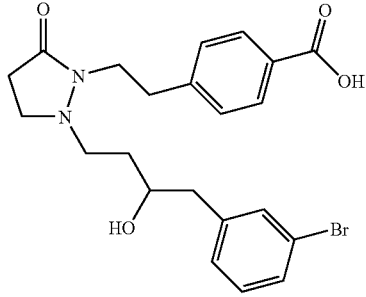

Example 23 was prepared using the procedures of Example 20 starting from (3-bromophenyl)acetic acid to give 23 as a white solid. $^1$H NMR (methanol-$d_4$) δ 1.65-1.95 (m, 2H), 2.70-2.85 (m, 2H), 3.07 (t, 2H), 3.20-3.40 (m, 5H), 3.60-3.90 (m, 4H), 3.96-4.05 (m, 1H), 7.15-7.50 (m, 6H), 7.96 (d, 2H); MS (m/z) 462 (M+1).

Example 24

4-[2-(2-{3-hydroxy-4-[3-(trifluoromethoxy)phenyl]butyl}-5-oxopyrazolidin-1-yl)ethyl]benzoic acid

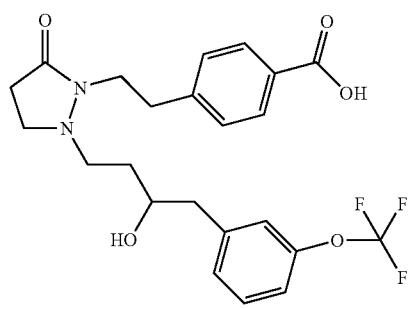

Example 24 was prepared using the procedures of Example 20 starting from [3-(trifluoromethoxy)phenyl]acetic acid to give 24 as a white solid. $^1$H NMR (methanol-$d_4$) δ 1.50-1.75 (m, 2H), 2.20-2.75 (m, 2H), 2.75-3.00 (m, 6H), 3.05-3.22 (m, 2H), 3.45-3.85 (m, 2H), 3.89-4.00 (m, 1H), 7.07-7.30 (m, 5H), 7.38 (t, 1H), 7.85 (d, 2H); MS (m/z) 467 (M+1).

Example 25

4-(2-{2-[4-(3-fluorophenyl)-3-hydroxybutyl]-5-oxopyrazolidin-1-yl}ethyl)benzoic acid

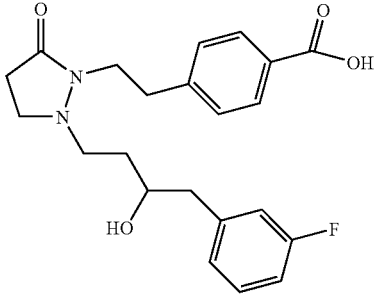

Example 25 was prepared using the procedures of Example 20 starting from (3-fluorophenyl)acetic acid to give 25 as a white solid. $^1$H NMR (methanol-$d_4$) δ 1.50-1.80 (m, 2H), 2.20-2.75 (m, 2H), 2.75-3.10 (m, 6H), 3.10-3.60 (m, 4H), 3.85-3.98 (m, 1H), 6.88-7.18 (m, 3H), 7.22-7.47 (m, 3H), 7.92 (d, 2H); MS (m/z) 401 (M+1).

Example 26

4-[2-(2-{3-hydroxy-4-[3-(trifluoromethyl)phenyl]butyl}-5-oxopyrazolidin-1-yl)ethyl]benzoic acid

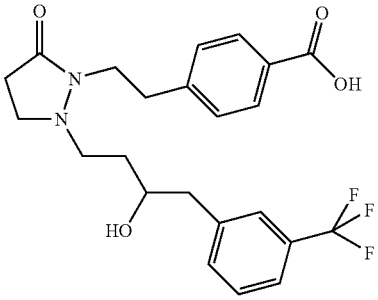

Example 26 was prepared using the procedures of Example 20 starting from [(3-trifluoromethyl)phenyl]acetic acid to give 26 as a white solid. $^1$H NMR (methanol-$d_4$) δ 1.50-1.80 (m, 2H), 2.20-2.75 (m, 2H), 2.75-3.00 (m, 6H), 3.10-3.20 (m, 2H), 3.40-3.90 (m, 2H), 3.90-3.98 (m, 1H), 7.20 (d, 2H), 7.45-7.63 (m, 4H), 7.86 (d, 2H); MS (m/z) 451 (M+1).

Example 27

4-(2-{2-[(4S)-3-hydroxy-4-phenylpentyl]-5-oxopyrazolidin-1-yl}ethyl)benzoic acid

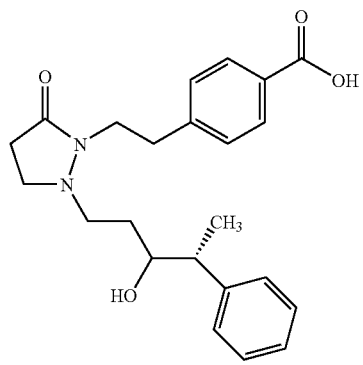

Example 27 was prepared using the procedures of Example 20 starting from (2S)-2-phenylpropanoic acid to give 27 as a white solid. MS (m/z) 397.5 (M+1).

Example 28

4-(2-{2-[4-(1,3-benzodioxol-5-yl)-3-hydroxybutyl]-5-oxopyrazolidin-1-yl}ethyl)benzoic acid

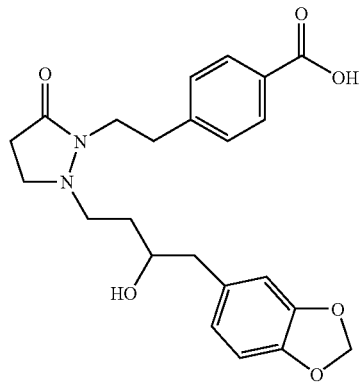

Example 28 was prepared using the procedures of Example 20 starting from 1,3-benzodioxol-5-ylacetic acid to give 28 as a white solid. $^1$H NMR (methanol-$d_4$) δ 1.45-1.75 (m, 2H), 2.20-2.65 (m, 2H), 2.65-3.80 (m, 2H), 2.80-3.05 (m, 4H), 3.10-3.25 (m, 2H), 3.40-3.80 (m, 2H), 3.85-3.95 (m, 1H), 5.90 (s, 2H), 6.65-7.80 (m, 3H), 7.20 (d, 2H), 7.85 (d, 2H); MS (m/z) 427 (M+1).

Example 29

4-(2-{2-[4-(3-chlorophenyl)-3-hydroxybutyl]-5-oxopyrazolidin-1-yl}ethyl)benzoic acid

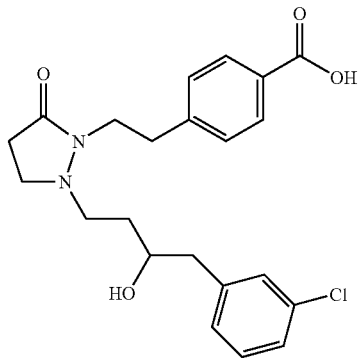

Example 29 was prepared using the procedures of example 20 starting from (3-chlorophenyl)acetic acid to give 29 as a white solid. $^1$H NMR (methanol-$d_4$) δ 1.48-1.75 (m, 2H), 2.20-2.65 (m, 2H), 2.75-3.00 (m, 6H), 3.10-3.25 (m, 2H), 3.40-3.85 (m, 2H), 3.90-4.05 (m, 1H), 7.15-7.38 (m, 6H), 7.85 (d, 2H); MS (m/z) 417.5 (M+1).

Example 30

4-(2-{2-[(4R)-3-hydroxy-4-phenylpentyl]-5-oxopyrazolidin-1-yl}ethyl)benzoic acid

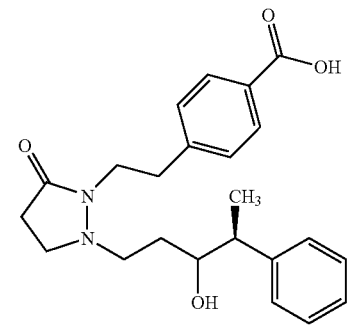

Example 30 was prepared using the procedures of Example 20 starting from (2R)-2-phenylpropanoic acid to give 30 as a white solid. $^1$H NMR (methanol-$d_4$) δ 1.25-1.70 (m, 6H), 2.10-2.70 (m, 2H), 2.75-3.05 (m, 6H), 3.10-3.20 (m, 2H), 3.80-3.90 (m, 1H), 7.15-7.40 (m, 7H), 7.92 (d, 2H); MS (m/z) 397.5 (M+1).

Example 31

EP2 Receptor Binding Assay

Compounds of the invention were tested in an EP2 receptor binding assay of the following protocol. As referred to herein, the term a "standard EP2 receptor binding assay" designates the following protocol.

A mixture containing 20 μg of EP2 receptor membranes, 0.5 mg of wheat germ agglutinin coated PVT-SPA beads, plus or minus a compound of the invention (25 μl per well) or 10 μM of cold PGE2 at 1% DMSO and 20 nM $^3$H-PGE2 in assay buffer containing 25 mM MES, 10 mM Mgcl2, 1 mM EDTA, pH 6.0 are incubated in Corning 3600 plates on a plate shaker for 2 hrs at room temperature. $^3$H-PGE2 binding is evaluated by counting the plates on the top count using the $^3$H SPA dpm2 program. % Binding and Ki value for inhibitors are calculated based on the one site competition parameter using the Graphpad prism program. Ki values are set forth in the Table I below.

Example 32

EP2 cAMP Assay

Compounds of the invention were tested in a total cAMP assay as follows. HEK293-EBNA cells transfected with pCEP4-hEP2 receptors were seeded in 96 well opaque plate (Costar #3917) at 4×10$^4$ cells per well in 100 μl of culture medium (D-MEM/F12 supplemented with 10% FBS, 2 nM L-glutamine, and 250 μg/ml of hygromycin; all from Gibco-BRL) and incubated at 37° C. After overnight incubation, the medium was removed from each well and replaced with 45 μl of assay medium consisted of phenol red free D-MEM/F-12, 0.1% BSA (GibcoBRL) and 0.1 mM3-isobutyl-1-methyl-xanthine (Sigma). After 15 minutes of incubation at 37° C., 16-16-dimethyl PGE-2 or compounds at desired concentrations in 20 μl of assay medium were added to cells and further incubated at 37° C. for 1 hour. Total cAMP (intra- and extra-cellular) was measured by using a cAMP-screen ELISA System (Tropix, #CS1000).

Results of the assays of Examples 31 and 32 are shown in the Table I below (EC50 (nM)).

TABLE I

| Example n° | Structure | h-EP2 Ki (nM) | h-EP2 EC$_{50}$ (nM) |
|---|---|---|---|
| 1 | 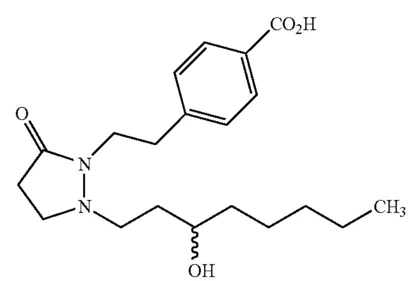 | 2 200 | 595 |
| 2 | 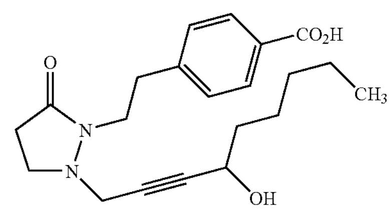 | >50 000 | >50 000 |
| 3 | 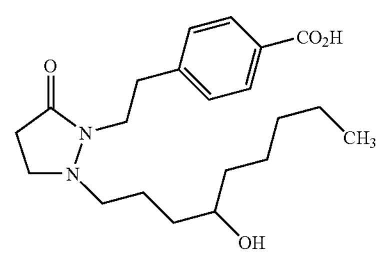 | 2 440 | 1 300 |
| 4 | 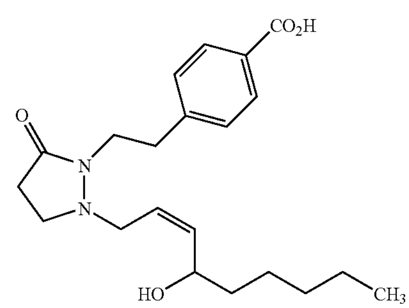 | 17 220 | 2 600 |

TABLE I-continued
| Example n° | Structure | h-EP2 Ki (nM) | h-EP2 EC$_{50}$ (nM) |
|---|---|---|---|
| 5 | 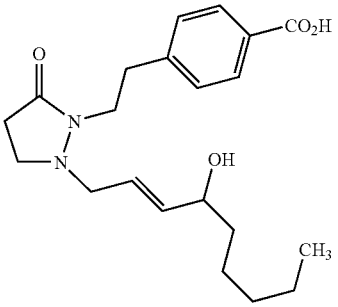 | 25 900 | 12 460 |
| 6 | 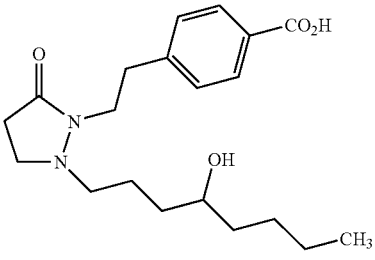 | 5 660 | 1 400 |
| 12 | 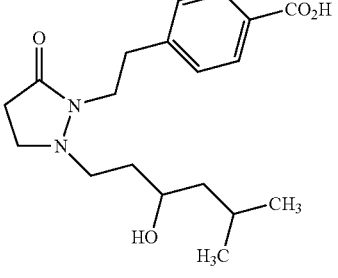 | 4 410 | 15 000 |
| 8 | 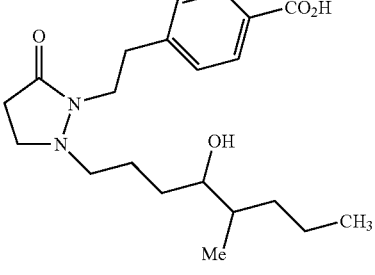 | 5 160 | 2 100 |
| 9 | 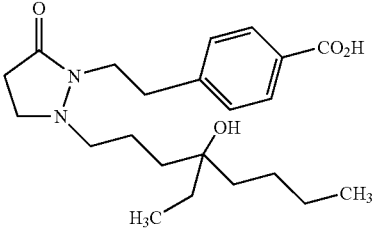 | 495 | 461 |

TABLE I-continued

| Example n° | Structure | h-EP2 Ki (nM) | h-EP2 EC$_{50}$ (nM) |
|---|---|---|---|
| 10 | 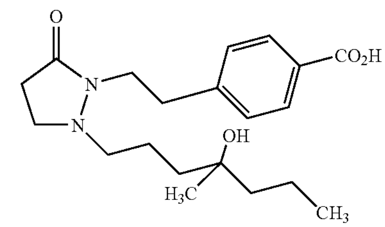 | 28 900 | 5300 |
| 11 | 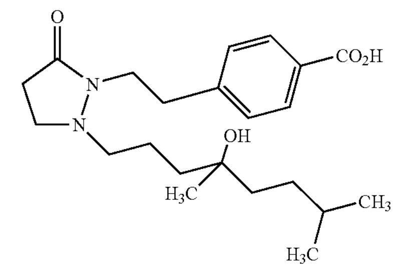 | 20 200 | 10 000 |
| 7 | 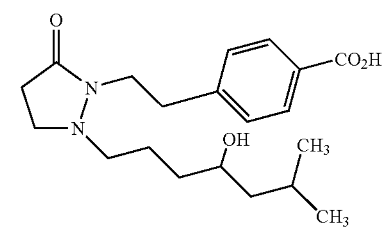 | 28 600 | 9 700 |
| 13 | 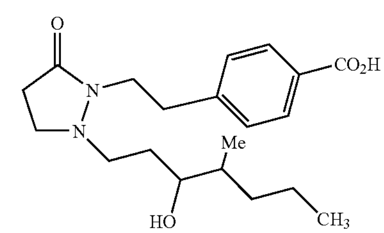 | 2 760 | 5 000 |
| 14 | 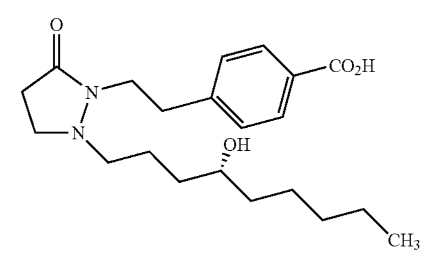 | 1 860 | 566 |
| 15 | 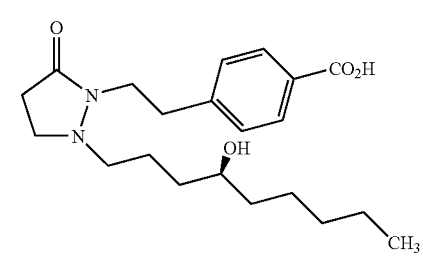 | 3 260 | 1 500 |

TABLE I-continued
| Example n° | Structure | h-EP2 Ki (nM) | h-EP2 EC$_{50}$ (nM) |
|---|---|---|---|
| 16 | 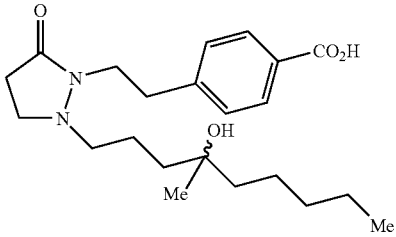 | 475 | 1 600 |
| 18 | 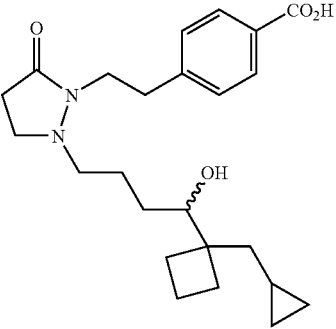 | 610 | 578 |
| 19 | 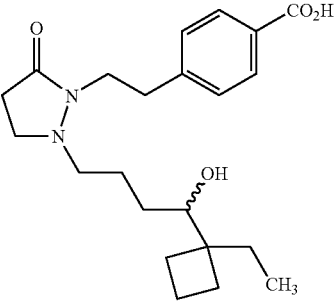 | 750 | 393 |
| 21 | 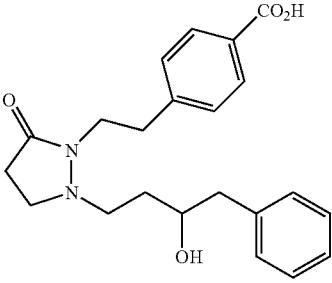 | 6 200 | |
| 22 | 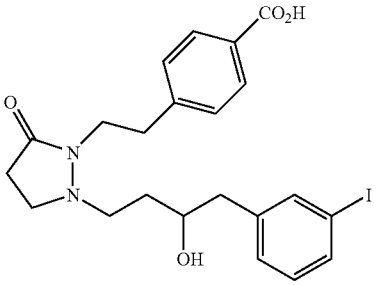 | 4 450 | |

TABLE I-continued

| Example n° | Structure | h-EP2 Ki (nM) | h-EP2 EC$_{50}$ (nM) |
| --- | --- | --- | --- |
| 23 | 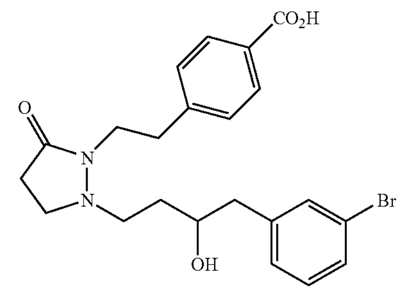 | 5 450 | |
| 24 | 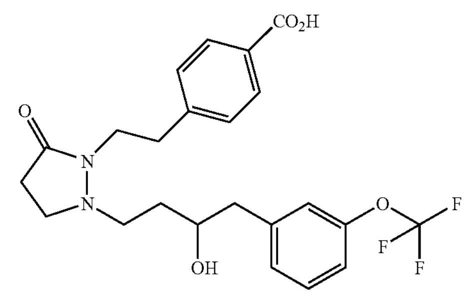 | 2 830 | |
| 25 | 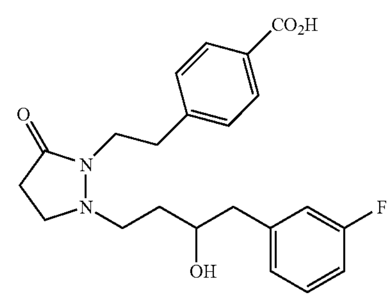 | 6 290 | |
| 26 | 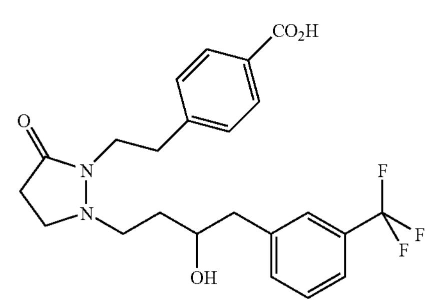 | 6 647 | 17 623 |

TABLE I-continued

| Example n° | Structure | h-EP2 Ki (nM) | h-EP2 EC$_{50}$ (nM) |
|---|---|---|---|
| 27 | 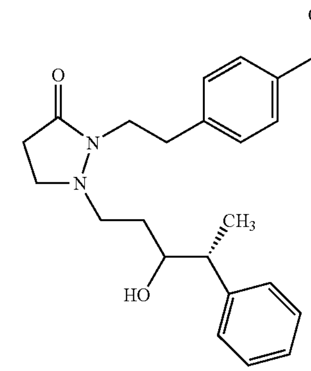 | 7 090 | |
| 29 | 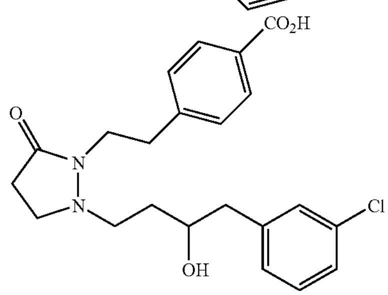 | 5 690 | |
| 30 | 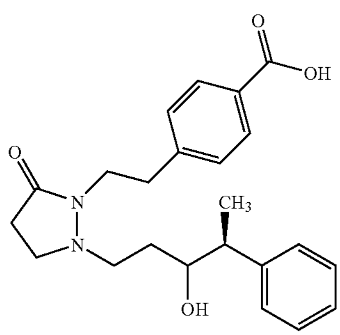 | 5 130 | |

Example 33

EP4 Binding Assay

Compounds of the invention were tested in an EP4 receptor binding assay of the following protocol.

A mixture containing 20 µg of EP4 receptor membranes, 0.5 mg of wheat germ agglutinin coated PVT-SPA beads, plus or minus a 1,2-substituted 5-pyrrolidinone compound of the invention (25 µl per well) or 10 µM of cold PGE2 at 1% DMSO and 20 nM $^3$H-PGE2 in assay buffer containing 25 mM MES, 10 mM MgCl$_2$, 1 mM EDTA, pH 6.0 are incubated in Corning 3600 plates on a plate shaker for 2 hrs at room temperature. $^3$H-PGE2 binding is evaluated by counting the plates on the top count using the $^3$H SPA dpm2 program. % Binding and Ki value for inhibitors are calculated based on the one site competition parameter using the Graphpad prism program. EP4 Ki values are set forth in the Table II below.

Example 34

EP4 cAMP Assay

Compounds of the invention were tested in a total cAMP assay as follows. HEK293-EBNA cells transfected with pCEP4-hEP4 receptors were seeded in 96 well opaque plate (Costar #3917) at 4×10$^4$ cells per well in 100 µl of culture medium (D-MEM/F12 supplemented with 10% FBS, 2 nM L-glutamine, and 250 µg/ml of hygromycin; all from Gibco-BRL) and incubated at 37° C. After overnight incubation, the medium was removed from each well and replaced with 45 µl of assay medium consisted of phenol red free D-MEM/F-12, 0.1% BSA (GibcoBRL) and 0.1 mM3-isobutyl-1-methyl-xanthine (Sigma). After 15 minutes of incubation at 37° C., 16-16-dimethyl PGE-2 or compounds of the invention at desired concentrations in 20 µl of assay medium were added to cells and further incubated at 37° C. for 1 hour. Total cAMP (intra- and extra-cellular) was measured by using a cAMP-screen ELISA System (Tropix, #CS1000). Results (EP4 EC$_{50}$ (nM)) are shown in the Table II immediately below.

Results of the assays of Examples 33 and 34 are set forth in the following Table II. In Table II, the tested compound is identified both by the corresponding synthetic Example number above as well as structure of the tested compound.

TABLE II

| Example n° | Structure | h-EP$_4$ Ki (nM) | h-EP$_4$ EC$_{50}$ (nM) |
|---|---|---|---|
| 30 | 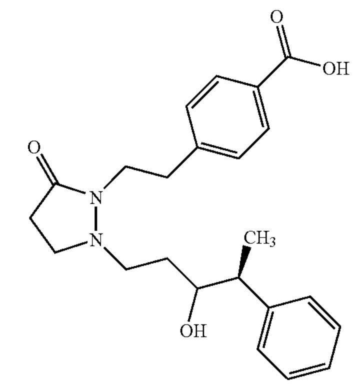 | | 93 |
| 29 | 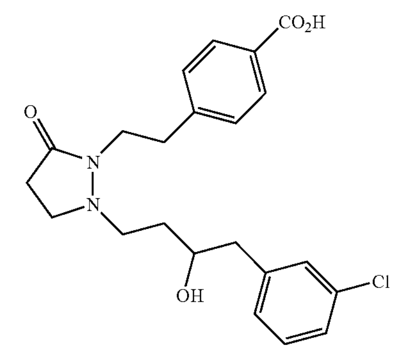 | | 18 |
| 28 | 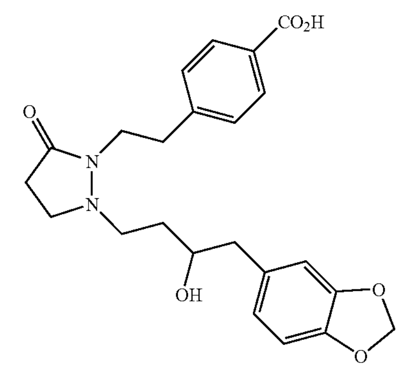 | | 376 |
| 27 | 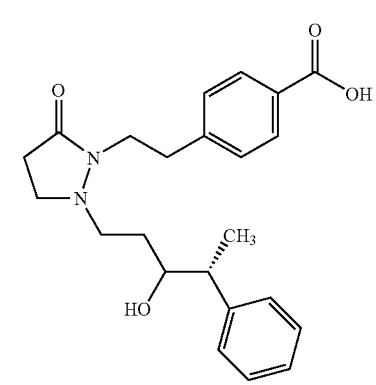 | | 95 |

TABLE II-continued
| Example n° | Structure | h-EP$_4$ Ki (nM) | h-EP$_4$ EC$_{50}$ (nM) |
|---|---|---|---|
| 26 | 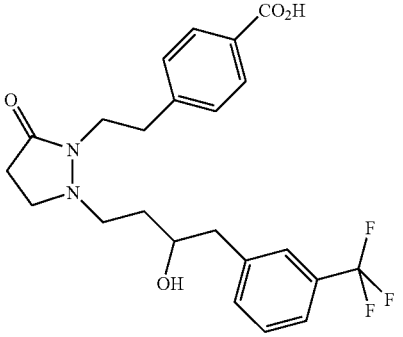 | 23 | 0.2 |
| 25 | 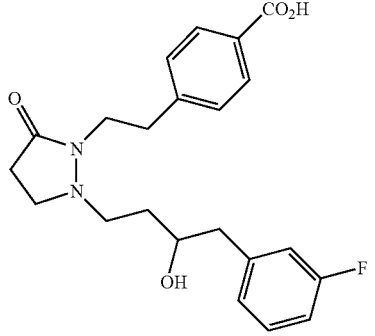 | 36 | |
| 24 | 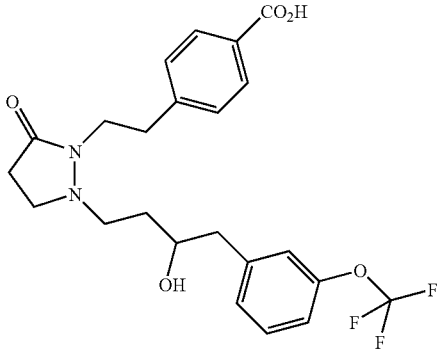 | 59 | |
| 23 | 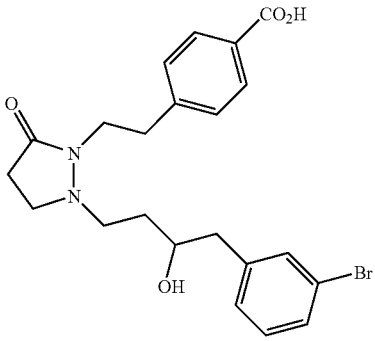 | 13 | |

TABLE II-continued

| Example n° | Structure | h-EP$_4$ Ki (nM) | h-EP$_4$ EC$_{50}$ (nM) |
|---|---|---|---|
| 22 | 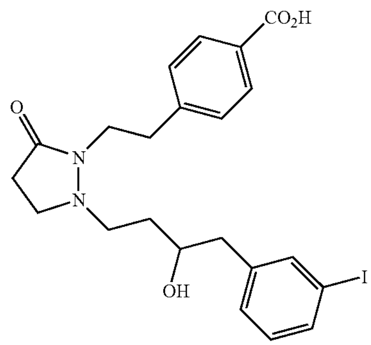 | 14 | |
| 21 | 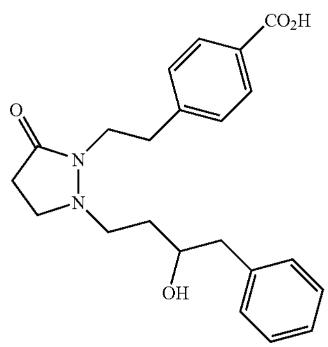 | 68 | |
| 14 | 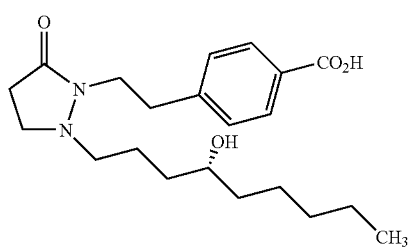 | 566 | 10 |
| 13 | 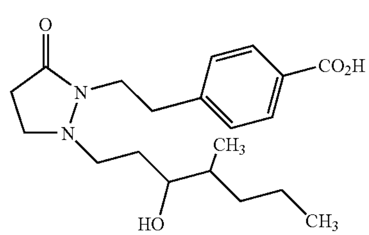 | 6 000 | |
| 12 | 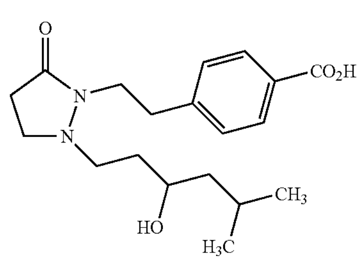 | 2 000 | 277 |

TABLE II-continued

| Example n° | Structure | h-EP$_4$ Ki (nM) | h-EP$_4$ EC$_{50}$ (nM) |
|---|---|---|---|
| 3 | 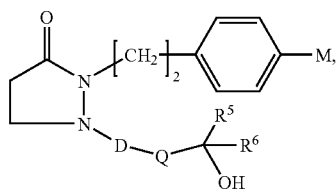 | 2 000 | |
| 1 | 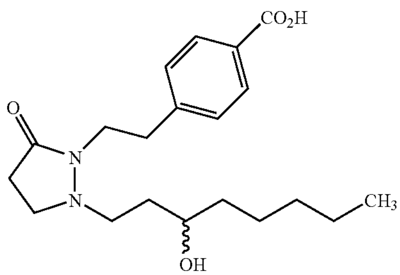 | 250 | 5 |

The invention has been described in detail with reference to preferred embodiments thereof. However, it will be appreciated that those skilled in the art, upon consideration of this disclosure, may make modifications and improvements within the spirit and scope of the invention.

The invention claimed is:

1. A method for treating a mammal from or susceptible to preterm labor, dysmenorrhea, asthma, hypertension, infertility or a fertility disorder, undesired blood clotting, preeclampsia or eclampsia, control of cervical ripening, sexual dysfunction, glaucoma, undesired bone loss, or an eosinophil disorder, comprising administering to the mammal an effective of amount of a compound of the following Formula VI:

VI wherein M is COX with X is OR' and R' is H;
D is $(CH_2)_{n''}$ wherein n'' is 2;
Q is $(CH_2)_{n'''}$ wherein n''' is 0 or 1;
$R^5$ is H or $C_1$-$C_6$ alkyl; and
$R^6$ is $C_1$-$C_6$ alkyl, aryl $C_1$-$C_6$ alkyl, heteroaryl $C_1$-$C_6$ alkyl, $C_3$-$C_6$ cylcoalkyl $C_1$-$C_6$ alkyl or $C_3$-$C_6$ cycloalkyl
and/or
pharmaceutically acceptable salts thereof.

2. The method of claim 1, wherein n''' is 1; $R^5$ is H, methyl or ethyl; $R^6$ is C1-C6 alkyl or $C_3$-$C_6$ cycloalkyl C1-C6 alkyl.

3. The method of claim 1, wherein n''' is 0; $R^5$ is H; $R^6$ is —CHR$^7$—W, wherein R$^7$ is H or $C_1$-$C_6$ alkyl; W is phenyl.

4. The method of claim 3, wherein R$^6$ is —CHR$^7$—W, wherein R$^7$ is H or methyl; W is unfused phenyl substituted with a group selected from the group consisting of H, halogen, —OCF3, and —CF3.

5. The method of claim 1, wherein the compound is selected from the group consisting of:
4-[2-(2-(3-hydroxyoctyl)-5-oxopyrazolidin-1-yl)ethyl]benzoic acid;
4-{2-[2-(4-hydroxynon-2-ynyl)-5-oxopyrazolidin-1-yl]ethyl}benzoic acid;
4-{2-[2-(4-hydroxynonyl)-5-oxopyrazolidin-1-yl]ethyl)benzoic acid;
4-(2-{2-[(2Z)-4-hydroxynon-2-enyl]-5-oxopyrazolidin-1-yl}ethyl)benzoic acid;
4-(2-{2-[(2E)-4-hydroxynon-2-enyl]-5-oxopyrazolidin-1-yl}ethyl)benzoic acid;
4-{2-[2-(4-hydroxyoctyl)-5-oxopyrazolidin-1-yl]ethyl}benzoic acid;
4-{2-[2-(4-hydroxy-6-methylheptyl)-5-oxopyrazolidin-1-yl]ethyl}benzoic acid;
4-{2-[2-(4-hydroxy-5-methyloctyl)-5-oxopyrazolidin-1-yl]ethyl)benzoic acid;
4-{2-[2-(4-ethyl-4-hydroxyoctyl)-5-oxopyrazolidin-1-yl]ethyl}benzoic acid;
4-{2-[2-(4-hydroxy-4-methylheptyl)-5-oxopyrazolidin-1-yl]ethyl}benzoic acid;
4-{2-[2-(4-hydroxy-4,7-dimethyloctyl)-5-oxopyrazolidin-1-yl]ethyl}benzoic acid;
4-{2-[2-(3-hydroxy-5-methylhexyl)-5-oxopyrazolidin-1-yl]ethyl)benzoic acid;
4-{2-[2-(3-cyclobutyl-3-hydroxypropyl)-5-oxopyrazolidin-1-yl]ethyl)benzoic acid;
4-{2-[2-((4S)-hydroxynonyl)-5-oxopyrazolidin-1-yl]ethyl)benzoic acid;
4-{2-[2-((4R)-hydroxynonyl)-5-oxopyrazolidin-1-yl]ethyl}benzoic acid;
4-[2-(2-{4-[1-(cyclopropylmethyl)cyclobutyl]-4-hydroxybutyl}-5-oxopyrazolidin-1-yl)ethyl]benzoic acid;

4-(2-{2-[4-(1-ethylcyclobutyl)-4-hydroxyoctyl]-5-oxopyrazolidin-1-yl}ethyl)benzoic acid;
4-[2-{2-[3-hydroxy-4-(3-methylphenyl)butyl]-5-oxopyrazolidin-1-yl}ethyl)benzoic acid;
4-{2-[2-(3-hydroxy-4-phenylbutyl)-5-oxopyrazolidin-1-yl]ethyl}benzoic acid;
4-(2-{2-[4-(3-iodophenyl)-3-hydroxyoctyl]-5-oxopyrazolidin-1-yl}ethyl)benzoic acid;
4-(2-{2-[4-(3-bromophenyl)-3-hydroxybutyl]-5-oxopyrazolidin-1-yl}ethyl)benzoic acid;
4-[2-(2-{3-hydroxy-4-[3-(trifluoromethoxy)phenyl]butyl}-5-oxopyrazolidin-1-yl)ethyl]benzoic acid;
4-(2-{2-[4-(3-fluorophenyl)-3-hydroxyoctyl]-5-oxopyrazolidin-1-yl}ethyl)benzoic acid;
4-[2-(2-{3-hydroxy-4-[3-(trifluoromethyl)phenyl]butyl})-5-oxopyrazolidin-1-yl)ethyl]benzoic acid;
4-(2-{2-[(3S,4S)-3-hydroxy-4-phenylpentyl]-5-oxopyrazolidin-1-yl}ethyl)benzoic acid;
4-(2-{2-[4-(1,3-benzodioxol-5-yl)-3-hydroxybutyl]-5-oxopyrazolidin-1-yl}ethyl)benzoic acid;
4-(2-{2-[4-(3-chlorophenyl)-3-hydroxybutyl]-5-oxopyrazolidin-1-yl}ethyl)benzoic acid;
4-(2-{2-[(4R)-3-hydroxy-4-phenylpentyl]-5-oxopyrazolidin-1-yl}ethyl)benzoic acid;
and pharmaceutically acceptable salts thereof.

6. The method as claimed in claim 1, wherein the mammal is suffering from or susceptible to preterm labor.

7. The method as claimed in claim 1, wherein the mammal is suffering from or susceptible to dysmenorrhea.

8. The method as claimed in claim 1, wherein the mammal is suffering from or susceptible to asthma.

9. The method as claimed in claim 1, wherein the mammal is suffering from or susceptible to hypertension.

10. The method as claimed in claim 1, wherein the mammal is suffering from or susceptible to infertility or a fertility disorder.

11. The method as claimed in claim 1, wherein the mammal is suffering from or susceptible to undesired blood clotting.

12. The method as claimed in claim 1, wherein the mammal is suffering from or susceptible to preeclampsia or eclampsia.

13. The method as claimed in claim 1, wherein the mammal is suffering from or susceptible to an eosinophil disorder.

14. The method as claimed in claim 1, wherein the mammal is suffering from or susceptible to undesired bone loss.

15. The method as claimed in claim 1, wherein the mammal is a female is late stage pregnancy and in need of control of cervical ripening.

16. The method as claimed in claim 1, wherein the mammal is suffering from sexual dysfunction.

17. The method as claimed in claim 1, wherein the mammal is suffering from or susceptible to glaucoma.

* * * * *